US006576443B2

(12) United States Patent
Hennecke et al.

(10) Patent No.: US 6,576,443 B2
(45) Date of Patent: Jun. 10, 2003

(54) REPLICON BASED ACTIVATION OF ENDOGENOUS GENES

(75) Inventors: Frank Hennecke, Zürich (CH); Wolfgang A. Renner, Zurich (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 79 days.

(21) Appl. No.: 09/733,042

(22) Filed: Dec. 11, 2000

(65) Prior Publication Data

US 2002/0168709 A1 Nov. 14, 2002

Related U.S. Application Data

(60) Provisional application No. 60/169,988, filed on Dec. 10, 1999.

(51) Int. Cl.[7] ............................. C12Q 1/68; C12P 21/06
(52) U.S. Cl. ........................................... 435/69.1; 435/6
(58) Field of Search .................. 435/6, 69.1, 320.1, 435/325; 530/350

(56) References Cited

U.S. PATENT DOCUMENTS

| | | | |
|---|---|---|---|
| 4,959,317 A | 9/1990 | Sauer | 435/172.3 |
| 5,091,309 A | 2/1992 | Schlesinger et al. | 435/69.1 |
| 5,217,879 A | 6/1993 | Huang et al. | 435/69.1 |
| 5,272,071 A | * 12/1993 | Chappel | 435/172.3 |
| 5,464,764 A | 11/1995 | Capecchi et al. | 435/172.3 |
| 5,532,154 A | 7/1996 | Brown | 435/235.1 |
| 5,578,473 A | 11/1996 | Palese et al. | 435/172.3 |
| 5,631,153 A | 5/1997 | Capecchi et al. | 435/172.3 |
| 5,641,670 A | 6/1997 | Treco et al. | 435/240.2 |
| 5,733,761 A | 3/1998 | Treco et al. | 435/172.3 |
| 5,756,349 A | 5/1998 | Lin | 435/325 |
| 5,789,215 A | 8/1998 | Berns et al. | 435/172.3 |
| 5,789,245 A | 8/1998 | Dubensky, Jr. et al. | 435/320.1 |
| 5,792,462 A | 8/1998 | Johnston et al. | 424/199.1 |

(List continued on next page.)

FOREIGN PATENT DOCUMENTS

| | | |
|---|---|---|
| EP | 0 716 148 | 6/1996 |
| WO | WO 93/09222 | 5/1993 |
| WO | WO 94/06908 | 3/1994 |
| WO | Wo 94/12650 | 6/1994 |
| WO | WO 94/17813 | 8/1994 |
| WO | WO 95/31560 | 11/1995 |
| WO | WO 96/17072 | 6/1996 |
| WO | WO 96/29411 | 9/1996 |
| WO | WO 97/38087 | 10/1997 |
| WO | WO 98/11206 | 3/1998 |
| WO | WO 98/36779 | 8/1998 |
| WO | WO 99/18226 | 4/1999 |
| WO | WO 99/50432 | 10/1999 |
| WO | WO 99/55866 | 11/1999 |
| WO | WO 99/57263 | 11/1999 |
| WO | WO 99/57291 | 11/1999 |
| WO | WO 99/57292 | 11/1999 |
| WO | WO 00/49162 | 8/2000 |

OTHER PUBLICATIONS

Schlesinger, S., and Dubensky, T.W. Jr., "Alphavirus vectors for gene expression and vaccines," *Curr Opin Biotechnol.* 10:434–439, Elsevier (1999).

(List continued on next page.)

*Primary Examiner*—Kenneth R. Horlick
(74) *Attorney, Agent, or Firm*—Sterne, Kessler, Goldstein & Fox, PLLC

(57) ABSTRACT

The present invention relates to methods for the modification of genomes of eukaryotic cells to alter the expression of endogenous genes. The invention also relates to recombinant eukaryotic host cells and polypeptides produced by the practice of the disclosed methods. The invention further relates to vector systems useful for modifying the genomes of eukaryotic cells to alter the expression of endogenous genes.

67 Claims, 17 Drawing Sheets

U.S. PATENT DOCUMENTS

| | | | |
|---|---|---|---|
| 5,814,482 A | 9/1998 | Dubensky, Jr. et al. | 435/69.3 |
| 5,821,093 A | 10/1998 | Ingram et al. | 435/161 |
| 5,843,723 A | 12/1998 | Dubensky, Jr. et al. | 435/69.3 |
| 5,968,502 A | 10/1999 | Treco et al. | 424/93.21 |
| 5,981,214 A | 11/1999 | Skoultchi | 435/69.1 |
| 5,994,127 A | 11/1999 | Selden et al. | 435/325 |
| 6,027,921 A | 2/2000 | Heartlein et al. | 435/69.7 |
| 6,048,524 A | 4/2000 | Selden et al. | 424/93.21 |
| 6,048,729 A | 4/2000 | Selden et al. | 435/455 |
| 6,054,288 A | 4/2000 | Selden et al. | 435/69.1 |
| 6,063,630 A | 5/2000 | Treco et al. | 435/463 |

OTHER PUBLICATIONS

International Search Report for International Application No. PCT/IB00/01841, mailed Jun. 7, 2001. (Not for Printing).

Agapov, E.V., et al., "Noncytopathic Sindbis virus RNA vectors for heterologous gene expression," *Proc. Natl. Acad. Sci. USA* 95:12989–12994, National Academy of Sciences of the USA (1988).

Altman–Hamamdzic, S., et al.,"Expression of β–galactosidase in mouse brain: utilization of a novel nonreplicative Sindbis virus vector as a neuronal gene delivery system," *Gene Ther.* 4:815–822, Stockton Press (1997).

Anderson, W.F., et al., "Human gene therapy," *Nature* 392:25–30, Macmillan Publishers Ltd (1997).

Arias, C., et al., "Sequence Analysis of Two Mutants of Sindbis Virus Defective in the Intracellular Transport of Their Glycoproteins," *J. Mol. Biol.* 168:87–102, Academic Press, Inc. (1983).

Artelt, P., et al., "Vectors for efficient expression in mammalian fibroblastoid, myeloid and lymphoid cells via transfection or infection," *Gene* 68:213–219, Elsevier Science Publishers B.V. (1988).

Ascensao, J.L., et al., "Erythropoietin Production by a Human Testicular Germ Cell Line," *Blood* 62:1132–1134, W. B. Saunders (1983).

Barton, D.J., et al., "Demonstration In Vitro of Temperature–Sensitive Elongation of RNA in Sindbis Virus Mutant ts6," *J. Virol.* 62:3597–3602, American Society for Microbiology (1988).

Berglund, P., et al, "Alphaviruses as vectors for gene delivery," *Trends Biotechnol.* 14:130–134, Elsevier Science Publishers B.V. (Biomedical Division) (1996).

Bredenbeek, P.J., et al., "Sindbis Virus Expression Vectors: Packaging of RNA Replicons by Using Defective Helper RNAs," *J. Virol.* 67:6439–6446, American Society for Microbiology (1993).

Bredenbeek, P.J., and Rice, C.M., "Animal RNA virus expression systems," *Semin. Virol.* 3:297–310, Academic Press (1992).

Burge, B.W., and Pfefferkorn, E.R., "Isolation and Characterization of Conditional–lethal Mutants of Sindbis Virus," *Virol.* 30:204–213, Academic Press (1966).

Burge, B.W., and Pfefferkorn, E.R., "Complementation Between Temperature–sensitive Mutants of Sindbis Virus," *Virol* 30:214–223, Academic Press (1966).

Caley, I.J., et al., "Humoral, Mucosal, and Cellular Immunity in Response to a Human Immunodeficiency Virus Type 1 Immunogen Expressed by a Venezuelan Equine Encephalitis Virus Vaccine Vector," *J. Virol.* 71:3031–3038, American Society for Microbiology (1997).

Carleton, M., and Brown, D.T., "Events in the Endoplasmic Reticulum Abrogate the Temperature Sensitivity of Sindbis Virus Mutant ts23," *J. Virol.* 70:952–959, American Society for Microbiology (1996).

Ciccarone, V., et al., "pSFV1 Eukaryotic Expression Vector: A Novel Protein Expression System," *Focus* 15:103–105, Life Technologies, Inc. (1993).

Clark, H.J., et al., "Comparative Characterization of a C–Type Virus–Producing Cell Line (VSW) and a Virus–Free Line (VH2) From *Vipera russelli*," *J. Natl. Cancer Inst.* 51:645–657, U.S. Department of Health, Education, and Welfare, Public Health Service, National Institutes of Health (1973).

Davis, N.L., et al., "In Vitro Synthesis of Infectious Venezuelan Equine Encephalitis Virus RNA from a cDNA Clone: Analysis of a Viable Deletion Mutant," *Virol.* 171:189–204, Academic Press (1989).

Davis, N.L., et al., "A Viral Vaccine Vector That Expresses Foreign Genes in Lymph Nodes and Protects against Mucosal Challenge," *J. Virol.* 70:3781–3787, American Society for Microbiology (1996).

De Groot, R.J., et al., "Sindbis virus RNA polymerase is degraded by the N–end rule pathway," *Proc. Natl. Acad. Sci. USA* 88:8967–8971, National Academy of Sciences of the USA (1991).

Dé, I., et al., "Sindbis Virus RNA–Negative Mutants That Fail to Convert from Minus–Strand to Plus–Strand Synthesis: Role of the nsP2 Protein," *J. Virol.* 70:2706–2719 (1996).

Deng, C., and Capecchi, M.R., "Reexamination of Gene Targeting Frequency as a Function of the Extent of Homology between the Targeting Vector and the Target Locus," *Mol. Cell. Biol.* 12:3365–3371, American Society for Microbiology (1992).

DiCiommo, D.P., and Bremner, R., "Rapid, High Level Protein Production Using DNA–based Semliki Forest Virus Vectors," *J. Biol. Chem.* 273:18060–18066, American Society for Biochemistry and Molecular Biology, Inc. (1998).

Doedens, J.R., et al., "Inhibition of Endoplasmic Reticulum– to–Golgi Traffic by Poliovirus Protein 3A: Genetic and Ultrastructural Analysis," *J. Virol.* 71:9054–9064, American Society for Microbiology (1997).

Dryga, S.A. et al., "Identification of Mutations in a Sindbis Virus Variant Able to Establish Persistent Infection in BHK Cells: The Importance of a Mutation in the nsP2 Gene," *Virol.* 228:74–83, Academic Press (1997).

Dubensky, Jr., T.W., et al., "Sindbis Virus DNA–Based Expression Vectors: Utility for In Vitro and In Vivo Gene Transfer," *J. Virol.* 70:508–519, American Society for Microbiology (1996).

Dubuisson, J., et al., "Formation and Intracellular Localization of Hepatitis C Virus Envelope Glycoprotein Complexes Expressed by Recombinant Vaccinia and Sindbis Viruses," *J. Virol.* 68:6147–6160, American Society for Microbiology (1994).

Frolov, I., et al., "Alphavirus–based expression vectors: Strategies and applications," *Proc. Natl. Acad. Sci. USA* 93:11371–11377, National Academy of Sciences of the USA (1996).

Furth, P.A., et al., "Temporal control of gene expression in transgenic mice by a tetracycline–responsive promoter," *Proc. Natl. Acad. Sci. USA* 91:9302–9306, National Academy of Sciences of the USA (1994).

Goldberg, M.A., et al., "The regulated expression of erythropoietin by two human hepatoma cell lines," *Proc. Natl. Acad. Sci. USA* 84:7972–7976, National Academy of Sciences of the USA (1987).

Grakoui, A., et al., "A cis–Acting Mutation in the Sindbis Virus Junction Region Which Affects Subgenomic RNA Synthesis," *J. Virol.* 63:5216–5227, American Society for Microbiology (1989).

Guan, H., et al., "RNA promoters located on (–)–strands of a subviral RNA associated with turnip crinkle virus," *RNA* 3:1401–1412, Cambridge University Press (1997).

Hahn, C.S., et al., "Infectious Sindbis virus transient expression vectors s for studying antigen processing and presentation," *Proc. Natl. Acad. Sci. USA* 89:2679–2683, National Academy of Sciences of the USA (1992).

Hakimi, J., and Atkinson, P.H., "Glycosylation of Intracellular Sindbis Virus Glycoproteins," *Biochem.* 21:2140–2145, American Chemical Society (1982).

Hariharan, M.J., et al., "DNA Immunization against Herpes Simplex Virus: Enhanced Efficacy Using a Sindbis Virus–Based Vector," *J. Virol.* 72:950–958, American Society for Microbiology (1998).

Hennighausen, L., et al., "Conditional Gene Expression in Secretory Tissues and Skin of Transgenic Mice Using the MMTV–LTR and the Tetracycline Responsive System," J. Cell. Biochem. 59:463–472, Wiley–Liss, Inc. (1995).

Herweijer, H., et al., "A Plasmid–Based Self–Amplifying Sindbis Virus Vector," *Hum. Gene Ther.* 6:1161–1167, Mary Ann Liebert, Inc. (1995).

Hoffmann, A., et al., "A novel tetracycline–dependent expression vector with low basal expression and potent regulatory properties in various mammalian cell lines," *Nucl. Acids Res.* 25:1078–1079, Oxford University Press (1997).

Huang, H.V., "Sindbis virus vectors for expression in animal cells," *Curr. Opin. Biotech.* 7:531–535, Current Biology, Ltd. (1996).

Invitrogen Manual, "Sindbis Expression System, Version C," from internet web page [retrievable from: http://www.invitrogen.com/manuals.html], Catalog No. K750–01, Invitrogen Corporation (1996).

Jeng, S.–Y., et al., "Characterization and Partial Purification of Bovine α–Lactalbumin and β–Casein Produced in Milk of Transgenic Mice," *J. Dairy Sci.* 80:3167–3175, American Dairy Science Association (1997).

Johanning, F.W., et al., "A sindbis virus mRNA polynucleotide vector achieves prolonged and high level heterologous gene expression in vivo," *Nucl. Acids Res.* 23:1495–1501, Oxford University Press (1995).

Keränen, S., and Kääriäinen, L., "Functional Defects of RNA–Negative Temperature–Sensitive Mutants of Sindbis and Semliki Forest Viruses," *J. Virol.* 32:19–29, American Society for Microbiology (1979).

Khromykh, A.A., et al., "Efficient trans–Complementation of the Flavivirus Kunjin NS5 Protein but Not of the NS1 Protein Requires Its Coexpression with Other Components of the Viral Replicase," *J. Virol.* 73:10272–10280, American Society for Microbiology (Dec. 1999).

Khromykh, A.A., and Westaway, E.G., "Subgenomic Replicons of the Flavivirus Kunjin: Construction and Applications," *J. Virol.* 71:1497–1505, American Society for Microbiology (1997).

Khromykh, A.A., et al., "trans–Complementation of Flavivirus RNA Polymerase Gene NS5 by Using Kunjin Virus Replicon–Expressing BHK Cells," *J. Virol.* 72:7270–7279, American Society for Microbiology (1998).

Kistner, A., et al., "Doxycycline–mediated quantitative and tissue–specific control of gene expression in transgenic mice," *Proc. Natl. Acad. Sci. USA* 93:10933–10938, National Academy of Sciences of the USA (1996).

Kohno, A., et al., "Semliki Forest virus–based DNA expression vector: transient protein production followed by cell death," *Gene Ther.* 5:415–418, Stockton Press (1998).

Kuhn, R.J., et al., "Mutagenesis of the 3' Nontranslated Region of Sindbis Virus RNA," *J. Virol.* 64:1465–1476, American Society for Microbiology (1990).

Kujala, P., et al., "Monoclonal antibodies specific for Semliki Forest virus replicase protein nsP2," *J. Gen. Virol.* 78:343–351, Society for General Microbiology (1997).

Laakkonen, P., et al., "Alphavirus Replicase Protein NSP1 Induces Filopodia and Rearrangement of Actin Filaments," *J. Virol.* 72:10265–10269, American Society for Microbiology (1998).

Lai, L.–W., et al., "Homologous Recombination Based Gene Therapy," *Exp. Nephrol.* 7:11–14, Karger A.G. (Jan.–Feb. 1999).

Lama, J., et al., "Genetic analysis of poliovirus protein 3A: characterization of a non–cytopathic mutant virus defective in killing Vero cells," *J. Gen. Virol.* 79:1911–1921, Society for General Microbiology (1998).

Landis, H., et al., "Human MxA Protein Confers Resistance to Semliki Forest Virus and Inhibits the Amplification of a Semliki Forest Virus–Based Replicon in the Absence of Viral Structural Proteins," *J. Virol.* 72:1516–1522, American Society for Microbiology (1998).

Lavrovsky, Y., et al., "Therapeutic Potential and Mechanism of Action of Oligonucleotides and Ribozymes," *Biochem. Mol. Med.* 62:11–22, Academic Press (1997).

Leake, C.J., et al., "Cytopathic Effect and Plaque Formation by Arboviruses in a Continuous Cell Line (XTC–2) from the Toad *Xenopus laevis,*" *J. Gen. Virol.* 35:335–339, Society for General Microbiology (1977).

Lee, K.H., et al., "Two–Dimensional Electrophoresis of Proteins as a Tool in the Metabolic Engineering of Cell Cycle Regulation," *Biotechnol. Bioengin.* 50:336–340, Wiley (1996).

Lemm, J.A. and Rice, C.M., "Assembly of Functional Sindbis Virus RNA Replication Complexes: Requirement for Coexpression of P123 and P34," *J. Virol.* 67:1905–1915, American Society for Microbiology (1993).

Lemm, J.A., et al., "Mutations Which Alter the Level or Structure of nsP4 Can Affect the Efficiency of Sindbis Virus Replication in a Host–Dependent Manner," *J. Virol.* 64:3001–3011, American Society for Microbiology (1990).

Levis, R., et al., "Promoter for Sindbis Virus RNA–Dependent Subgenomic RNA Transcription," *J. Virol.* 64:1726–1733, American Society for Microbiology (1990).

Liljeström, P. and Garoff, H., "A New Generation of Animal Cell Expression Vectors Based on the Semliki Forest Virus Replicon," *Bio/Technol.* 9:1356–1361, Nature Publishing Co. (1991).

Liljeström, P., "Alphavirus expression systems," *Curr. Opin. Biotechnol.* 5:495–500, Current Biology, Ltd. (1994).

Limonta, J., et al., "Production of active anti–CD6 mouse/human chimeric antibodies in the milk of transgenic mice," *Immunotech.* 1:107–113, Elsevier (1995).

Lindqvist, B.H., et al., "Sindbis Virus Mutant ts20 of Complementation Group E Contains a Lesion in Glycoprotein E2," *Virol. 151:*10–20, Academic Press (1986).

Lundstrom, K., "Alphaviruses as expression vectors," *Curr. Opin. Biotechnol. 8:*578–582, Current Biology, Ltd. (1997).

Máthé, E., et al., "The Tomaj mutant alleles of αTubulin67C reveal a requirement for the encoded maternal specific tubulin isoform in the sperm aster, the cleavage spindle apparatus and neurogenesis during embryonic development in Drosophila," *J. Cell Sci. 111:*887–896, The Company of Biologists Ltd. (1998).

Meade, H. and Ziomek, C., "Urine as a substitute for milk?" *Nature Biotechnol. 16:*21–22, Nature Publishing Co. (1998).

Miki, T., "Heterogeneity of Sindbis Virus Glycoprotein $E_1$ and its Modification by Host Cell Transformation," *J. Gen. Virol. 65:*343–354, Society for General Microbiology (1984).

Minch, S.L., et al., "Tissue Plasminogen Activator Coexpressed in Chinese Hamster Ovary Cells with α(2,6)–Sialytransferase Contains NeuAcα(2,6)Galβ(1,4)Glc–N–AcR Linkages," *Biotechnol. Prog. 11:*348–351, American Chemical Society and the American Institute of Chemical Engineers (1995).

Müller, U., "Ten years of gene targeting: targeted mouse mutants, from vector design to phenotype analysis," *Mech. Dev. 82:*3–21, Elsevier Science Ireland, Ltd. (Apr. 1999).

O'Reilly, E.K., et al., "Interactions between the Structural Domains of the RNA Replication Proteins of Plant–Infecting RNA Viruses," *J. Virol. 72:*7160–7169, American Society for Microbiology (1998).

Olkkonen, V.M., et al., "Expression of Exogenous Proteins in Mammalian Cells with the Semliki Forest Virus Vector," *Meth. Cell Biol. 43:*43–53, Academic Press (1994).

Palese, P., et al., "Negative–strand RNA viruses: Genetic engineering and applications," *Proc. Natl. Acad. Sci. USA 93:*11354–11358, National Academy of Sciences of the USA (1996).

Patterson, B., et al., "Cold–sensitive Mutants G680V and G691C of Dictyostelium Myosin II confer Dramatically Different Biochemical Defects," *J. Biol. Chem. 272:*27612–27617, American Society for Biochemistry and Molecular Biology, Inc. (1997).

Paul, N.L., et al., "Expression of HIV–1 Envelope Glycoproteins by Semliki Forest Virus Vectors," *AIDS Res. Hum. Retroviruses 9:*963–970, Mary Ann Leibert, Inc., Publishers (1993).

Pfeffer, M., et al., "The Alphavirus 3'–Nontranslated Region: Size Heterogeneity and Arrangement of Repeated Sequence Elements," *Virol. 240:*100–108, Academic Press (1998).

Piper, R.C., et al., "Recombinant Sindbis Virus as an Expression System for Cell Biology," *Meth. Cell Biol. 43:*55–78, Academic Press (1994).

Polo, J.M., et al., "Stable alphavirus packaging cell lines for Sindbis virus– and Semliki Forest virus–derived vectors," *Proc. Natl. Acad. Sci. USA 96:*4598–4603, National Academy of Sciences USA (Apr. 1999).

Pugachev, K.V. and Frey, T.K., "Effects of Defined Mutations in the 5' Nontranslated Region of Rubella Virus Genomic RNA on Virus Viability and Macromolecule Synthesis," *J. Virol. 72:*641–650, American Society for Microbiology (1998).

Pushko, P., et al., "Replicon–Helper Systems from Attenuated Venezuelan Equine Encephalitis Virus: Expression of Heterologous Genes in Vitro and Immunization against Heterologous Pathogens in Vivo," *Virol. 239:*389–401, Academic Press (1997).

Renner, W.A., et al., "Recombinant Cyclin E Expression Activates Proliferation and Obviates Surface Attachment of Chinese Hamster Ovary (CHO) Cells in Protein–Free Medium," *Biotechnol. Bioengin. 47:*476–482, Wiley (1995).

Rikkonen, M., "Functional Significance of the Nuclear–Targeting and NTP–Binding Motifs of Semliki Forest Virus Nonstructural Protein nsP2," *Virol. 218:*352–361, Academic Press (1996).

Roks, A.J.M., et al., "Vectors based on Semliki Forest virus for rapid and efficient gene transfer into non–endothelial cardiovascular cells: comparison to adenovirus," *Cardiovascular Res. 35:*498–504, Elsevier Science B.V. (1997).

Saez, E., et al., "Inducible gene expression in mammalian cells and transgenic mice," *Curr. Opin. Biotechnol. 8:*608–616, Current Biology, Ltd. (1997).

Scallan, M.F., et al., "bcl–2 Acts Early To Restrict Semliki Forest Virus Replication and Delays Virus–Induced Programmed Cell Death," *J. Virol. 71:*1583–1590, American Society for Microbiology (1997).

Schlesinger, S., "Alphaviruses—vectors for the expression of heterologous genes," *Trends Biotechnol. 11:*18–22, Elsevier Science Publishers B.V. (Biomedical Division) (1993).

Schlesinger, M.J., and Schlesinger, S., "Formation and Assembly of Alphavirus Glycoproteins," in *The Togaviridae and Flaviviridae,* Ch. 5, Plenum Press, New York, NY, pp. 121–148 (1986).

Schneider–Schaulies, S., et al., "Cell Type–Specific MxA–Mediated Inhibition of Measles Virus Transcription in Human Brain Cells," *J. Virol. 68:*6910–6917, American Society for Microbiology (1994).

Schnorr, J.–J., et al., "MxA–Dependent Inhibition of Measles Virus Glycoprotein Synthesis in a Stably Transfected Human Monocytic Cell Line," *J. Virol. 67:*4760–4768, American Society for Microbiology (1993).

Schwer, B., et al., "Effects of deletion mutations in the yeast Ces1 protein on cell growth and morphology and on high copy suppression of mutations in mRNA capping enzyme and translation initiation factor 4A," *Nucl. Acids Res. 26:*803–809, Oxford University Press (1998).

Sherwood, J.B., and Shouval, D., "Continuous production of erythropoietin by an established human renal carcinoma cell line: Development of the cell line," *Proc. Natl. Acad. Sci USA 83:*165–169, National Academy of Sciences of the USA (1986).

Shirako, Y., and Strauss, J.H., "Regulation of Sindbis Virus RNA Replication: Uncleaved P123 and nsP4 Function in Minus–Strand RNA Synthesis, whereas Cleaved Products from P123 Are Required for Efficient Plus–Strand RNA Synthesis," *J. Virol. 68:*1874–1885, American Society for Microbiology (1994).

Shockett, P.E., and Schatz, D.G., "Diverse strategies for tetracycline–regulated inducible gene expression," *Proc. Natl. Acad. Sci. USA 93:*5173–5176, National Academy of Sciences of the USA (1996).

Shockett, P., et al., "A modified tetracycline–regulated system provides autoregulatory, inducible gene expression in cultured cells and transgenic mice," *Proc. Natl. Acad. Sci. USA 92:*6522–6526, National Academy of Sciences of the USA (1995).

Siegel, R.W., et al., "Sequence–specific recognition of a subgenomic RNA promoter by a viral RNA polymerase," *Proc. Natl. Acad. Sci. USA 94:*11238–11243, National Academy of Sciences of the USA (1997).

Smith, S.M., et al., "Efficient Expression by an Alphavirus Replicon of a Functional Ribozyme Targeted to Human Immunodeficiency Virus Type 1," *J. Virol. 71:*9713–9721, American Society for Microbiology (1997).

Strauss, J.H., and Strauss, E.G., "The Alphaviruses: Gene Expression, Replication and Evolution," *Microbiol. Rev. 58:*491–562, American Society For Microbiology (1994).

Strauss, E.G. and Strauss, J.H., "Mutants of Alphaviruses: Genetics and Physiology," in *The Togaviruses,* Schlesinger, R. W., ed., Academic Press, New York, NY, pp. 393–426 (1980).

Suopanki, J., et al., "Regulation of alphavirus 26S mRNA transcription by replicase component nsP2," *J. Gen. Virol. 79:*309–319, Society for General Microbiology (1998).

Sytkowski, A.J., et al., "New Human Renal Carcinoma Cell Line Established from a Patient with Erythrocytosis," *Cancer Res. 43:*1415–1419, American Association For Cancer Research (1983).

Turina, M., et al., "Nucleotide Sequence and Infectivity of a Full–Length cDNA Clone of Panicum Mosaic Virus," *Virol. 241:*141–155, Academic Press (1998).

Urakami, S. et al., "Overexpression of Members of the AP–1 Transcriptional Factor Family from an Early Stage of Renal Carcinogenesis and Inhibition of Cell Growth by AP–1 Gene Antisense Oligonucleotides in the Tsc2 Gene Mutant (Eker) Rat Model," *Biochem. Biophys. Res. Commun. 241:*24–30, Academic Press, Inc. (1997).

van Dinten, L.C., et al., "An infectious arterivirus cDNA clone: Identification of a replicase point mutation that abolishes discontinuous mRNA transcription," *Proc. Natl. Acad. Sci. USA 94:*991–996, National Academy of Sciences of the USA (1997).

Verma, I.M., and Somia, N., "Gene therapy– promises, problems and prospects," *Nature 389:*239–242, Macmillan Publishers Ltd. (1997).

Wang, Y., et al., "A regulatory system for use in gene transfer," *Proc. Natl. Acad. Sci. USA 91:*8180–8184, National Academy of Sciences of the USA (1994).

Wang, Y., et al., "Ligand–inducible and liver–specific target gene expression in transgenic mice," *Nature Biotechnol. 15:*239–243, Nature Publishing Co. (1997).

Wang, J., and Simon, A.E., "Analysis of the Two Subgenomic RNA Promoters for Turnip Crinkle Virus in Vivo and in Vitro," *Virol. 232:*174–186, Academic Press (1997).

Watson, E., et al., "Structure determination of the intact major sialylated oligosaccharide chains of recombinant human erythropoietin expressed in Chinese hamster ovary cells," *Glycobiol. 4:*227–237, IRL Press at Oxford University Press (1994).

Weiss, B., et al., "Establishment and Maintenance of Persistent Infection by Sindbis Virus in BHK Cells," *J. Virol. 33:*463–474, American Society for Microbiology (1980).

Wengler, G., "Effects of Alphaviruses on Host Cell Macromolecular Synthesis," in *The Togaviruses, Biology Structure, Replication,* Chapter 16, R.W. Schlesinger, ed., Academic Press, New York, NY, pp. 459–472 (1980).

Wimmel, A., et al., "Inducible acceleration of $G_1$ progression through tetracycline–regulated expression of human cyclin E," *Oncogene 9:*995–997, McMillan Press (1994).

Xiong, C., et al., "Sindbis Virus: An Efficient, Broad Host Range Vector for Gene Expression in Animal Cells," *Science 243:*1188–1191, Association for the Advancement of Science (1988).

Younker, D.R. and Sawicki, S.G., "Negative Strand RNA Synthesis by Temperature–Sensitive Mutants of Mouse Hepatitis Virus," in *Coronaviruses and Arteriviruses,* Chapter 27, Enjuanes, L., et al., eds., Plenum Press, New York, pp. 221–226 (1998).

Yu, H., et al., "Inducible Human Immunodeficiency Virus Type 1 Packaging Cell Lines," *J. Virol. 70:*4530–4537, American Society for Microbiology (1996).

Zang, M., et al., "Production of Recombinant Proteins in Chinese Hamster Ovary Cells Using a Protein–Free Cell Culture Medium," *Bio/technol. 13:*389–392, Nature Publishing Co. (1995).

Zhang, J., et al., "Cloning of human IL–12 p40 and p35 DNA into the Semliki Forest virus vector: expression of IL–12 in human tumor cells," *Gene Ther. 4:*367–374, Stockton Press (1997).

Fiering, S., et al., "Analysis of Mammalian Cis–regulatory DNA Elements by Homologous Recombination," *Meth. Enzymol. 306:*42–66, Academic Press (1999).

Garoff, H., and Li, K.–J., "Recent advances in gene expression using alphavirus vectors," *Curr. Opin. Biotechnol. 9:*464–469, Current Biology Ltd. (1998).

Johnson, B.W., et al., "Inhibition of luciferase expression in transgenic *Aedes aegypti* mosquitos by Sindbis virus expression of antisense luciferase RNA," *Proc. Natl. Acad. Sci. USA 96:*13399–13403, National Academy of Sciences of the USA (1999).

Templeton, N.S., "Strategies for Improving the Frequency and Assessment of Homologous Recombination," *Meth. Mol. Biol. 133:*45–60, Humana Press, Inc. (1999).

\* cited by examiner

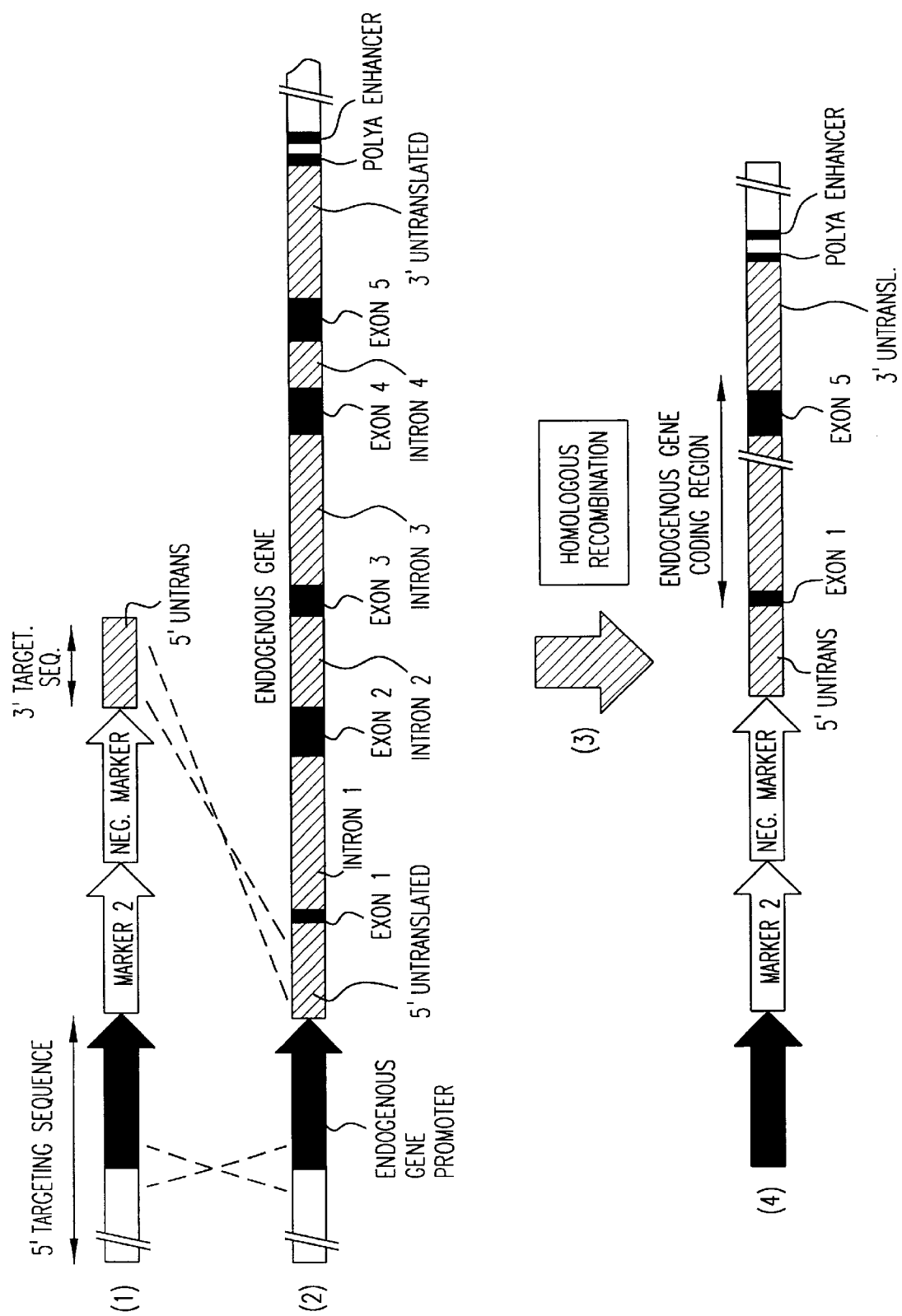

```
CTGACGCGCCCTGTAGCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATTAGGGTGATGGTTCACGTAGTG
GGCCATCGCCCTGATAGACGGTTTTTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGCTTACAATTTCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAgcgcgcaattaaccctcactaa
agggaacaaaagctggctagtgGATCCAGTCTTATGCAATACTCTTGTAGTCTTGCAACATGGTAACGATGAGTTAGCAA
CATGCCTTACAAGGAGAGAAAAAGCACCGTGCATGCCGATTGGTGGAAGTAAGGTGGTACGATCGTGCCTTATTAGGAAG
GCAACAGACGGGTCTGACATGGATTGGACGAACCACTGAATTCCGCATTGCAGAGATATTGTATTTAAGTGCCCTACCTc
gataccgTCGAGATTGACGGCGTAGTACACACTATTGAATCAAACAGCCGACCAATTGCACTACCATCACAATGGAGAAG
CCAGTAGTAAACGTAGACGTAGACCCCCAGAGTCCGTTTGTCGTGCAACTGCAAAAAAGCTTCCCGCAATTTGAGGTAGT
AGCACAGCAGGTCACTCCAAATGACCATGCTAATGCCAGAGCATTTTCGCATCTGGCCAGTAAACTAATCGAGCTGGAGG
TTCCTACCACAGCGACGATCTTGGACATAGGCAGCGCACCGGCTCGTAGAATGTTTTCCGAGCACCAGTATCATTGTGTC
TGCCCCATGCGTAGTCCAGAAGACCCGGACCGCATGATGAAATACGCCAGTAAACTGGCGGAAAAAGCGTGCAAGATTAC
AAACAAGAACTTGCATGAGAAGATTAAGGATCTCCGGACCGTACTTGATACGCCGGATGCTGAAACACCATCGCTCTGCT
TTCACAACGATGTTACCTGCAACATGCGTGCCGAATATTCCGTCATGCAGGACGTGTATATCAACGCTCCCGGAACTATC
TATCATCAGGCTATGAAAGGCGTGCGGACCCTGTACTGGATTGGCTTCGACACCACCCAGTTCATGTTCTCGGCTATGGC
AGGTTCGTACCCTGCGTACAACACCAACTGGGCCGACGAGAAAGTCCTTGAAGCGCGTAACATCGGACTTTGCAGCACAA
AGCTGAGTGAAGGTAGGACAGGAAAATTGTCGATAATGAGGAAGAAGGAGTTGAAGCCCGGGTCGCGGGTTTATTTCTCC
GTAGGATCGACACTTTATCCAGAACACAGAGCCAGCTTGCAGAGCTGGCATCTTCCATCGGTGTTCCACTTGAATGGAAA
GCAGTCGTACACTTGCCGCTGTGATACAGTGGTGAGTTGCGAAGGCTACGTAGTGAAGAAAATCACCATCAGTCCCGGGA
TCACGGGAGAAACCGTGGGATACGCGGTTACACACAATAGCGAGGGCTTCTTGCTATGCAAAGTTACTGACACAGTAAAA
GGAGAACGGGTATCGTTCCCTGTGTGCACGTACATCCCGGCCACCATATGCGATCAGATGACTGGTATAATGGCCACGGA
TATATCACCTGACGATGCACAAAAACTTCTGGTTGGGCTCAACCAGCGAATTGTCATTAACGGTAGGACTAACAGGAACA
CCAACACCATGCAAAATTACCTTCTGCCGATCATAGCACAAGGGTTCAGCAAATGGGCTAAGGAGCGCAAGGATGATCTT
GATAACGAGAAAATGCTGGGTACTAGAGAACGCAAGCTTACGTATGGCTGCTTGTGGGCGTTTCGCACTAAGAAAGTACA
TTCGTTTTATCGCCCACCTGGAACGCAGACCTGCGTAAAAGTCCCAGCCTCTTTTAGCGCTTTTCCCATGTCGTCCGTAT
GGACGACCTCTTTGCCCATGTCGCTGAGGCAGAAATTGAAACTGGCATTGCAACCAAAGAAGGAGGAAAAACTGCTGCAG
GTCTCGGAGGAATTAGTCATGGAGGCCAAGGCTGCTTTTGAGGATGCTCAGGAGGAAGCCAGAGCGGAGAAGCTCCGAGA
AGCACTTCCACCATTAGTGGCAGACAAAGGCATCGAGGCAGCCGCAGAAGTTGTCTGCGAAGTGGAGGGGCTCCAGGCGG
ACATCGGAGCAGCATTAGTTGAAACCCCGCGCGGTCACGTAAGGATAATACCTCAAGCAAATGACCGTATGATCGGACAG
TATATCGTTGTCTCGCCAAACTCTGTGCTGAAGAATGCCAAACTCGCACCAGCGCACCCGCTAGCAGATCAGGTTAAGAT
CATAACACACTCCGGAAGATCAGGAAGGTACGCGGTCGAACCATACGACGCTAAAGTACTGATGCCAGCAGGAGGTGCCG
TACCATGGCCAGAATTCCTAGCACTGAGTGAGAGCGCCACGTTAGTGTACAACGAAAGAGAGTTTGTGAACCGCAAACTA
TACCACATTGCCATGCATGGCCCCGCCAAGAATACAGAAGAGGAGCAGTACAAGGTTACAAAGGCAGAGCTTGCAGAAAC
AGAGTACGTGTTTGACGTGGACAAGAAGCGTTGCGTTAAGAAGGAAGAAGCCTCAGGTCTGGTCCTCTCGGGAGAACTGA
CCAACCCTCCCTATCATGAGCTAGCTCTGGAGGGACTGAAGACCCGACCTGCGGTCCCGTACAAGGTCGAAACAATAGGA
GTGATAGGCACACCGGGGTCGGGCAAGTCAGCTATTATCAAGTCAACTGTCACGGCACGAGATCTTGTTACCAGCGGAAA
GAAAGAAAATTGTCGCGAAATTGAGGCCGACGTGCTAAGACTGAGGGGTATGCAGATTACGTCGAAGACAGTAGATTCGG
TTATGCTCAACGGATGCCACAAAGCCGTAGAAGTGCTGTACGTTGACGAAGCGTTCGCGTGCCACGCAGGAGCACTACTT
GCCTTGATTGCTATCGTCAGGCCCCGCAAGAAGGTAGTACTATGCGGAGACCCCATGCAATGCGGATTCTTCAACATGAT
GCAACTAAAGGTACATTTCAATCACCCTGAAAAAGACATATGCACCAAGACATTCTACAAGTATATCTCCCGGCGTTGCA
```

FIG.8A

```
CACAGCCAGTTACAGCTATTGTATCGACACTGCATTACGATGGAAAGATGAAAACCACGAACCCGTGCAAGAAGAACATT
GAAATCGATATTACAGGGGCCACAAAGCCGAAGCCAGGGGATATCATCCTGACATGTTTCCGCGGGTGGGTTAAGCAATT
GCAAATCGACTATCCCGGACATGAAGTAATGACAGCCGCGGCCTCACAAGGGCTAACCAGAAAAGGAGTGTATGCCGTCC
GGCAAAAAGTCAATGAAAACCCACTGTACGCGATCACATCAGAGCATGTGAACGTGTTGCTCACCCGCACTGAGGACAGG
CTAGTGTGGAAAACCTTGCAGGGCGACCCATGGATTAAGCAGCCCACTAACATACCTAAAGGAAACTTTCAGGCTACTAT
AGAGGACTGGGAAGCTGAACACAAGGGAATAATTGCTGCAATAAACAGCCCCACTCCCCGTGCCAATCCGTTCAGCTGCA
AGACCAACGTTTGCTGGGCGAAAGCATTGGAACCGATACTAGCCACGGCCGGTATCGTACTTACCGGTTGCCAGTGGAGC
GAACTGTTCCCACAGTTTGCGGATGACAAACCACATTCGGCCATTTACGCCTTAGACGTAATTTGCATTAAGTTTTTCGG
CATGGACTTGACAAGCGGACTGTTTTCTAAACAGAGCATCCCACTAACGTACCATCCCGCCGATTCAGCGAGGCCGGTAG
CTCATTGGGACAACAGCCCAGGAACCCGCAAGTATGGGTACGATCACGCCATTGCCGCCGAACTCTCCCGTAGATTTCCG
GTGTTCCAGCTAGCTGGGAAGGGCACACAACTTGATTTGCAGACGGGGAGAACCAGAGTTATCTCTGCACAGCATAACCT
GGTCCCGGTGAACCGCAATCTTCCTCACGCCTTAGTCCCCGAGTACAAGGAGAAGCAACCCGGCCCGGTCAAAAAATTCT
TGAACCAGTTCAAACACCACTCAGTACTTGTGGTATCAGAGGAAAAAATTGAAGCTCCCCGTAAGAGAATCGAATGGATC
GCCCCGATTGGCATAGCCGGTGCAGATAAGAACTACAACCTGGCTTTCGGGTTTCCGCCGCAGGCACGGTACGACCTGGT
GTTCATCAACATTGGAACTAAATACAGAAACCACCACTTTCAGCAGTGCGAAGACCATGCGGCGACCTTAAAAACCCTTT
CGCGTTCGGCCCTgaattgTTtAaacTcaggaggcacCCTCGTGGTGAAGTCCTATGGCTACGCCGACCGCAACAGTGAG
GACGTAGTCACCGCTCTTGCCAGAAAGTTTGTCAGGGTGTCTGCAGCGAGACCAGATTGTGTCTCAAGCAATACAGAAAT
GTACCTGATTTTTCCGACAACTAGACAACAGCCGTACACGGCAATTCACCCCGCACCATCTGAATTGCGTGATTTCGTCCG
TGTATGAGGGTACAAGAGATGGAGTTGGAGCCGCGCCGTCATACCGCACCAAAAGGGAGAATATTGCTGACTGTCAAGAG
GAAGCAGTTGTCAACGCAGCCAATCCGCTGGGTAGACCAGGCGAAGGAGTCTGCCGTGCCATCTATAAACGTTGGCCGAC
CAGTTTTACCGATTCAGCCACGGAGACAGGCACCGCAAGAATGACTGTGTGCCTAGGAAAGAAAGTGATCCACGCGGTCG
GCCCTGATTTCCGGAAGCACCCAGAAGCAGAAGCCTTGAAATTGCTACAAAACGCCTACCATGCAGTGGCAGACTTAGTA
AATGAACATAACATCAAGTCTGTCGCCATTCCACTGCTATCTACAGGCATTTACGCAGCCGGAAAAGACGCCTTGAAGT
ATCACTTAACTGCTTGACAACCGCGCTAGACAGAACTGACGCGGACGTAACCATCTATTGCCTGGATAAGAAGTGGAAGG
AAAGAATCGACGCGGCACTCCAACTTAAGGAGTCTGTAACAGAGCTGAAGGATGAAGATATGGAGATCGACGATGAGTTA
GTATGGATtCATCCAGACAGTTGCTTGAAGGGAAGAAAGGGATTCAGTACTACAAAAGGAAAATTGTATTCGTACTTCGA
AGGCACCAAATTCCATCAAGCAGCAAAAGACATGGCGGAGATAAAGGTCCTGTTCCCTAATGACCAGGAAAGTAATGAAC
AACTGTGTGCCTACATATTGGGTGAGACCATGGAAGCAATCCGCGAAAAGTGCCCGGTCGACCATAACCCGTCGTCTAGC
CCGCCCAAAACGTTGCCGTGCCTTTGCATGTATGCCATGACGCCAGAAAGGGTCCACAGACTTAGAAGCAATAACGTCAA
AGAAGTTACAGTATGCTCCTCCACCCCCCTTCCTAAGCACAAAATTAAGAATGTTCAGAAGGTTCAGTGCACGAAAGTAG
TCCTGTTTAATCCGCACACTCCCGCATTCGTTCCCGCCCGTAAGTACATAGAAGTGCCAGAACAGCCTACCGCTCCTCCT
GCACAGGCCGAGGAGGCCCCCGAAGTTGTAGCGACACCGTCACCATCTACAGCTGATAACACCTCGCTTGATGTCACAGA
CATCTCACTGGATATGGATGACAGTAGCGAAGGCTCACTTTTTTTCGAGCTTTAGCGGATCGGACAACTCTATTACTAGTA
TGGACAGTTGGTCGTCAGGACCTAGTTCACTAGAGATAGTAGACCGAAGGCAGGTGGTGGTGGCTGACGTTCATGCCGTC
CAAGAGCCTGCCCCTATTCCACCGCCAAGGCTAAAGAAGATGGCCCGCCTGGCAGCGGCAAGAAAAGAGCCCACTCCACC
GGCAAGCAATAGCTCTGAGTCCCTCCACCTCTCTTTTGGTGGGGTATCCATGTCCCTCGGATCAATTTTCGACGGAGAGA
CGGCCCGCCAGGCAGCGGTACAACCCCTGGCAACAGGCCCCACGGATGTGCCTATGTCTTTCGGATCGTTTTCCGACGGA
GAGATTGATGAGCTGAGCCGCAGAGTAACTGAGTCCGAACCCGTCCTGTTTGGATCATTTGAACCGGGCGAAGTGAACTC
AATTATATCGTCCCGATCAGCCGTATCTTTTCCACTACGCAAGCAGAGACGTAGACGCAGGAGCAGGAGGACTGAATACT
GACTAACCGGGGTAGGTGGGTACATATTTTCGACGGACACAGGCCCTGGGCACTTGCAAAAGAAGTCCGTTCTGCAGAAC
CAGCTTACAGAACCGACCTTGGAGCGCAATGTCCTGGAAAGAATTCATGCCCCGGTGCTCGACACGTCGAAAGAGGAACA
ACTCAAACTCAGGTACCAGATGATGCCCACCGAAGCCAACAAAAGTAGGTACCAGTCTCGTAAAGTAGAAAATCAGAAAG
CCATAACCACTGAGCGACTACTGTCAGGACTACGACTGTATAACTCTGCCACAGATCAGCCAGAATGCTATAAGATCACC
TATCCGAAACCATTGTACTCCAGTAGCGTACCGGCGAACTACTCCGATCCACAGTTCGCTGTAGCTGTCTGTAACAACTA
```

FIG.8B

```
TCTGCATGAGAACTATCCGACAGTAGCATCTTATCAGATTACTGACGAGTACGATGCTTACTTGGATATGGTAGACGaGA
CAGTCGCaTGCCTGGATACTGCAACCTTCTGCCCCGCTAAGCTTAGAAGTTACCCGAAAAAACATGAGTATAGAGCCCCG
AATATCCGCAGTGCGGTTCCATCAGCGATGCAGAACACGCTACAAAATGTGCTCATTGCCGCAACTAAAAGAAATTGCAA
CGTCACGCAGATGCGTGAACTGCCAACACTGGACTCAGCGACATTCAATGTCGAATGCTTTCGAAAATATGCATGTAATG
ACGAGTATTGGGAGGAGTTCGCTCGGAAGCCAATTAGGATTACCACTGAGTTTGTCACCGCATATGTAGCTAGACTGAAA
GGCCCTAAGGCCGCCGCACTATTTGCAAAGACGTATAATTTGGTCCCATTGCAAGAAGTGCCTATGGATAGATTCGTCAT
GGACATGAAAAGAGACGTGAAAGTTACACCAGGCACGAAACACACAGAAGAAAGACCGAAAGTACAAGTGATACAAGCCG
CAGAACCCCTGGCGACTGCTTACTTATGCGGGATTCACCGGGAATTAGTGCGTAGGCTTACGGCCGTCTTGCTTCCAAAC
ATTCACACGCTTTTTGACATGTCGGCGGAGGATTTTGATGCAATCATAGCAGAACACTTCAAGCAAGGCGACCCGGTACT
GGAGACGGATATCGCATCATTCGACAAAAGCCAAGACGACGCTATGGCGTTAACCGGTCTGATGATCTTGGAGGACCTGG
GTGTGGATCAACCACTACTCGACTTGATCGAGTGCGCCTTTGGAGAAATATCATCCACCCATCTACCTACGGGTACTCGT
TTTAAATTCGGGGCGATGATGAAATCCGGAATGTTCCTCACACTTTTTGTCAACACAGTTTTGAATGTCGTTATCGCCAG
CAGAGTACTAGAAGAGCGGCTTAAAACGTCCAGATGTGCAGCGTTCATTGGCGACGACAACATCATACATGGAGTAGTAT
CTGACAAAGAAATGGCTGAGAGGTGCGCCACCTGGCTCAACATGGAGGTTAAGATCATCGACGCAGTCATCGGTGAGAGA
CCACCTTACTTCTGCGGCGGATTTATCTTGCAAGATTCGGTTACTTCCACAGCGTGCCGCGTGGCGGATCCCCTGAAAAG
GCTGTTTAAGTTGGGTAAACCGCTCCCAGCCGACGACGAGCAAGACGAAGACAGAAGACGCGCTCTGCTAGATGAAACAA
AGGCGTGGTTTAGAGTAGGTATAACAGGCACTTTAGCAGTGGCCGTGACGACCCGGTATGAGGTAGACAATATTACACCT
GTCCTACTGGCATTGAGAACTTTTGCCCAGAGCAAAAGAGCATTCCAAGCCATCAGAGGGGAAATAAAGCATCTCTACGG
TGGTCCTAAATAGTCAGCATAGTACATTTCATCTGACTAATACTACAACACCACCACCTctagaCGCGTAGAtctcacgt
gagcatgcaggccttgggCCCAATGATCCGACCAGCAAAACTCGATGTACTTCCGAGGAACTGATGTGCATAATGCATCA
GGCTGGTACATTAGATCCCCGCTTACCGCGGGCAATATAGCAACACTAAAAACTCGATGTACTTCCGAGGAAGCGCAGTG
CATAATGCTGCGCAGTGTTGCCACATAACCACTATATTAACCATTTATCTAGCGGACGCCAAAAACTCAATGTATTTCTG
AGGAAGCGTGGTGCATAATGCCACGCAGCGTCTGCATAACTTTTATTATTTCTTTTATTAATCAACAAAATTTTGTTTTT
AACATTTCAAAAAAAAAAAAAAAAAAAAAAAAAAAAAAAAAAAAAAAAAGGGAATTCCCAACTTGTTTATTGCAGCTTATAATG
GTTACAAATAAAGCAATAGCATCACAAATTTCACAAATAAAGCATTTTTTTCACTGCATTCTAGTTGTGGTTTGTCCAAA
CTCATCAATGTATCTTATCATGTCTGGATCCGTCGAGACGCGTccaattcgccctatagtgagtcgtattacgcgcgcTT
GGCGTAATCATGGTCATAGCTGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAATGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTGCCGGGAAGCTAG
```

FIG.8C

```
AGTAAGTAGTTCGCCAGTTAATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCGCGCACATTTCCCCGAAAAGTGCC
AC
```

FIG.8D

SEQUENCE LISTING

```
<160> NUMBER OF SEQ ID NOS:   49

<210> SEQ ID NO 1
<211> LENGTH: 11282
```

<212> TYPE: DNA
<213> ORGANISM: pCYTts

<400> SEQUENCE: 1

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg ctcccttta gggttccgat      180
ttagtgcttt acggcacctc gaccccaaaa aacttgatta gggtgatggt tcacgtagtg     240
ggccatcgcc ctgatagacg gttttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt aacaaaaat     420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcaattaa ccctcactaa agggaacaaa agctggctag    660
tggatccagt cttatgcaat actcttgtag tcttgcaaca tggtaacgat gagttagcaa    720
catgccttac aaggagagaa aaagcaccgt gcatgccgat tggtggaagt aaggtggtac    780
gatcgtgcct tattaggaag gcaacagacg ggtctgacat ggattggacg aaccactgaa    840
ttccgcattg cagagatatt gtatttaagt gccctacctc gataccgtcg agattgacgg    900
cgtagtacac actattgaat caaacagccg accaattgca ctaccatcac aatggagaag    960
ccagtagtaa acgtagacgt agaccccag agtccgtttg tcgtgcaact gcaaaaaagc    1020
ttcccgcaat ttgaggtagt agcacagcag gtcactccaa atgaccatgc taatgccaga   1080
gcattttcgc atctggccag taaactaatc gagctggagg ttcctaccac agcgacgatc   1140
ttggacatag gcagcgcacc ggctcgtaga atgttttccg agcaccagta tcattgtgtc   1200
tgccccatgc gtagtccaga agacccggac cgcatgatga aatacgccag taaactggcg   1260
gaaaaagcgt gcaagattac aaacaagaac ttgcatgaga agattaagga tctccggacc   1320
gtacttgata cgccggatgc tgaaacacca tcgctctgct ttcacaacga tgttacctgc   1380
aacatgcgtg ccgaatattc cgtcatgcag gacgtgtata tcaacgctcc cggaactatc   1440
tatcatcagg ctatgaaagg cgtgcggacc ctgtactgga ttggcttcga caccacccag   1500
ttcatgttct cggctatggc aggttcgtac cctgcgtaca acaccaactg ggccgacgag   1560
aaagtccttg aagcgcgtaa catcggactt tgcagcacaa agctgagtga aggtaggaca   1620
ggaaaattgt cgataatgag gaagaaggag ttgaagcccg ggtcgcgggt ttatttctcc   1680
gtaggatcga cactttatcc agaacacaga gccagcttgc agagctggca tcttccatcg   1740
gtgttccact tgaatggaaa gcagtcgtac acttgccgct gtgatacagt ggtgagttgc   1800
gaaggctacg tagtgaagaa aatcaccatc agtcccggga tcacgggaga accgtggga    1860
tacgcggtta cacacaatag cgagggcttc ttgctatgca aagttactga cacagtaaaa   1920
ggagaacggg tatcgttccc tgtgtgcacg tacatcccgg ccaccatatg cgatcagatg   1980
actggtataa tggccacgga tatatcacct gacgatgcac aaaaacttct ggttgggctc   2040
aaccagcgaa ttgtcattaa cggtaggact aacaggaaca ccaacaccat gcaaaattac   2100
cttctgccga tcatagcaca agggttcagc aaatgggcta aggagcgcaa ggatgatctt   2160
gataacgaga aaatgctggg tactagagaa cgcaagctta cgtatggctg cttgtgggcg   2220
```

-continued

```
tttcgcacta agaaagtaca ttcgttttat cgcccacctg gaacgcagac ctgcgtaaaa    2280
gtcccagcct cttttagcgc ttttcccatg tcgtccgtat ggacgacctc tttgcccatg    2340
tcgctgaggc agaaattgaa actggcattg caaccaaaga aggaggaaaa actgctgcag    2400
gtctcggagg aattagtcat ggaggccaag gctgcttttg aggatgctca ggaggaagcc    2460
agagcggaga agctccgaga agcacttcca ccattagtgg cagacaaagg catcgaggca    2520
gccgcagaag ttgtctgcga agtggagggg ctccaggcgg acatcggagc agcattagtt    2580
gaaaccccgc gcggtcacgt aaggataata cctcaagcaa atgaccgtat gatcggacag    2640
tatatcgttg tctcgccaaa ctctgtgctg aagaatgcca aactcgcacc agcgcacccg    2700
ctagcagatc aggttaagat cataacacac tccggaagat caggaaggta cgcggtcgaa    2760
ccatacgacg ctaaagtact gatgccagca ggaggtgccg taccatggcc agaattccta    2820
gcactgagtg agagcgccac gttagtgtac aacgaaagag agtttgtgaa ccgcaaacta    2880
taccacattg ccatgcatgg ccccgccaag aatacagaag aggagcagta caaggttaca    2940
aaggcagagc ttgcagaaac agagtacgtg tttgacgtgg acaagaagcg ttgcgttaag    3000
aaggaagaag cctcaggtct ggtcctctcg ggagaactga ccaaccctcc ctatcatgag    3060
ctagctctgg agggactgaa gacccgacct gcggtcccgt acaaggtcga acaatagga    3120
gtgataggca caccggggtc gggcaagtca gctattatca agtcaactgt cacggcacga    3180
gatcttgtta ccagcggaaa gaagaaaaat tgtcgcgaaa ttgaggccga cgtgctaaga    3240
ctgagggggta tgcagattac gtcgaagaca gtagattcgg ttatgctcaa cggatgccac    3300
aaagccgtag aagtgctgta cgttgacgaa gcgttcgcgt gccacgcagg agcactactt    3360
gccttgattg ctatcgtcag gccccgcaag aaggtagtac tatgcggaga ccccatgcaa    3420
tgcggattct tcaacatgat gcaactaaag gtacatttca atcaccctga aaaagacata    3480
tgcaccaaga cattctacaa gtatatctcc cggcgttgca cacagccagt tacagctatt    3540
gtatcgacac tgcattacga tggaaagatg aaaaccacga acccgtgcaa gaagaacatt    3600
gaaatcgata ttcaggggc cacaaagccg aagcagggg atatcatcct gacatgtttc    3660
cgcgggtggg ttaagcaatt gcaaatcgac tatcccggac atgaagtaat gacagccgcg    3720
gcctcacaag ggctaaccag aaaaggagtg tatgccgtcc ggcaaaaagt caatgaaaac    3780
ccactgtacg cgatcacatc agagcatgtg aacgtgttgc tcacccgcac tgaggacagg    3840
ctagtgtgga aaaccttgca gggcgaccca tggattaagc agcccactaa catacctaaa    3900
ggaaactttc aggctactat agaggactgg gaagctgaac aagggaat aattgctgca    3960
ataaacagcc ccactccccg tgccaatccg ttcagctgca gaccaacgt ttgctgggcg    4020
aaagcattgg aaccgatact agccacggcc ggtatcgtac ttaccggttg ccagtggagc    4080
gaactgttcc cacagtttgc ggatgacaaa ccacattcgg ccatttacgc cttagacgta    4140
atttgcatta agttttcgg catggacttg acaagcggac tgttttctaa acagagcatc    4200
ccactaacgt accatcccgc cgattcagcg aggccggtag ctcattggga caacagccca    4260
ggaacccgca gtatgggta cgatcacgcc attgccgccg aactctcccg tagatttccg    4320
gtgttccagc tagctgggaa gggcacacaa cttgatttgc agacggggag aaccagagtt    4380
atctctgcac agcataacct ggtcccggtg aaccgcaatc ttcctcacgc cttagtcccc    4440
gagtacaagg agaagcaacc cggcccggtc aaaaaattct tgaaccagtt caaacaccac    4500
tcagtacttg tggtatcaga ggaaaaaatt gaagctcccc gtaagagaat cgaatggatc    4560
gccccgattg gcatagccgg tgcagataag aactacaacc tggctttcgg gtttccgccg    4620
```

```
caggcacggt acgacctggt gttcatcaac attggaacta aatacagaaa ccaccacttt    4680
cagcagtgcg aagaccatgc ggcgaccttc aaaacccttt cgcgttcggc cctgaattgt    4740
ttaaactcag gaggcaccct cgtggtgaag tcctatggct acgccgaccg caacagtgag    4800
gacgtagtca ccgctcttgc cagaaagttt gtcagggtgt ctgcagcgag accagattgt    4860
gtctcaagca atacagaaat gtacctgatt ttccgacaac tagacaacag ccgtacacgg    4920
caattcaccc cgcaccatct gaattgcgtg atttcgtccg tgtatgaggg tacaagagat    4980
ggagttggag ccgcgccgtc ataccgcacc aaaagggaga atattgctga ctgtcaagag    5040
gaagcagttg tcaacgcagc caatccgctg ggtagaccag gcgaaggagt ctgccgtgcc    5100
atctataaac gttggccgac cagttttacc gattcagcca cggagacagg caccgcaaga    5160
atgactgtgt gcctaggaaa gaaagtgatc cacgcggtcg ccctgatttt ccggaagcac    5220
ccagaagcag aagccttgaa attgctacaa aacgcctacc atgcagtggc agacttagta    5280
aatgaacata acatcaagtc tgtcgccatt ccactgctat ctacaggcat ttacgcagcc    5340
ggaaaagacc gccttgaagt atcacttaac tgcttgacaa ccgcgctaga cagaactgac    5400
gcggacgtaa ccatctattg cctggataag aagtggaagg aaagaatcga cgcggcactc    5460
caacttaagg agtctgtaac agagctgaag gatgaagata tggagatcga cgatgagtta    5520
gtatggattc atccagacag ttgcttgaag ggaagaaagg gattcagtac tacaaaagga    5580
aaattgtatt cgtacttcga aggcaccaaa ttccatcaag cagcaaaaga catggcggag    5640
ataaaggtcc tgttccctaa tgaccaggaa agtaatgaac aactgtgtgc ctacatattg    5700
ggtgagacca tggaagcaat ccgcgaaaag tgcccggtcg accataaccc gtcgtctagc    5760
ccgcccaaaa cgttgccgtg cctttgcatg tatgccatga cgccagaaag ggtccacaga    5820
cttagaagca ataacgtcaa agaagttaca gtatgctcct ccaccccct tcctaagcac    5880 aaaattaaga atgttcagaa ggttcagtgc acgaaagtag tcctgtttaa tccgcacact    5940
cccgcattcg ttcccgcccg taagtacata gaagtgccag aacagcctac cgctcctcct    6000
gcacaggccg aggaggcccc cgaagttgta gcgacaccgt caccatctac agctgataac    6060
acctcgcttg atgtcacaga catctcactg gatatggatg acagtagcga aggctcactt    6120
ttttcgagct ttagcggatc ggacaactct attactagta tggacagttg gtcgtcagga    6180
cctagttcac tagagatagt agaccgaagg caggtggtgg tggctgacgt tcatgccgtc    6240
caagagcctg cccctattcc accgccaagg ctaaagaaga tggcccgcct ggcagcggca    6300
agaaaagagc ccactccacc ggcaagcaat agctctgagt ccctccacct ctcttttggt    6360
ggggtatcca tgtccctcgg atcaattttc gacggagaga cggcccgcca ggcagcggta    6420
caacccctgg caacaggccc cacggatgtg cctatgtctt tcggatcgtt ttccgacgga    6480
gagattgatg agctgagccg cagagtaact gagtccgaac ccgtcctgtt tggatcattt    6540
gaaccgggcg aagtgaactc aattatatcg tcccgatcag ccgtatcttt tccactacgc    6600
aagcagagac gtagacgcag gagcaggagg actgaatact gactaaccgg ggtaggtggg    6660
tacatatttt cgacggacac aggccctggg cacttgcaaa agaagtccgt tctgcagaac    6720
cagcttacag aaccgacctt ggagcgcaat gtcctggaaa gaattcatgc cccggtgctc    6780
gacacgtcga agaggaaca actcaaactc aggtaccaga tgatgcccac cgaagccaac    6840
aaaagtaggt accagtctcg taagtagaaa atcagaaaag ccataaccac tgagcgacta    6900
ctgtcaggac tacgactgta taactctgcc acagatcagc cagaatgcta aagatcacc    6960
```

-continued

```
tatccgaaac cattgtactc cagtagcgta ccggcgaact actccgatcc acagttcgct    7020
gtagctgtct gtaacaacta tctgcatgag aactatccga cagtagcatc ttatcagatt    7080
actgacgagt acgatgctta cttggatatg gtagacgaga cagtcgcatg cctggatact    7140
gcaaccttct gccccgctaa gcttagaagt tacccgaaaa acatgagtaa tagagccccg    7200
aatatccgca gtgcggttcc atcagcgatg cagaacacgc tacaaaatgt gctcattgcc    7260
gcaactaaaa gaaattgcaa cgtcacgcag atgcgtgaac tgccaacact ggactcagcg    7320
acattcaatg tcgaatgctt tcgaaaatat gcatgtaatg acgagtattg ggaggagttc    7380
gctcggaagc caattaggat taccactgag tttgtcaccg catatgtagc tagactgaaa    7440
ggccctaagg ccgccgcact atttgcaaag acgtataatt tggtcccatt gcaagaagtg    7500
cctatggata gattcgtcat ggacatgaaa agagacgtga agttacacc aggcacgaaa    7560 cacacagaag aaagaccgaa agtacaagtg atacaagccg cagaacccct ggcgactgct    7620
tacttatgcg ggattcaccg ggaattagtg cgtaggctta cggccgtctt gcttccaaac    7680
attcacacgc tttttgacat gtcggcggag gattttgatg caatcatagc agaacacttc    7740
aagcaaggcg acccggtact ggagacggat atcgcatcat tcgacaaaag ccaagacgac    7800 gctatgcgt taaccggtct gatgatcttg gaggacctgg gtgtggatca accactactc    7860
gacttgatcg agtgcgcctt tggagaaata tcatccaccc atctacctac gggtactcgt    7920
tttaaattcg gggcgatgat gaaatccgga atgttcctca cttttttgt caacacagtt    7980 ttgaatgtcg ttatcgccag cagagtacta gaagagcggc ttaaaacgtc cagatgtgca    8040
gcgttcattg gcgacgacaa catcatacat ggagtagtat ctgacaaaga aatggctgag    8100
aggtgcgcca cctggctcaa catggaggtt aagatcatcg acgcagtcat cggtgagaga    8160
ccaccttact tctgcggcgg atttatcttg caagattcgg ttacttccac agcgtgccgc    8220
gtggcggatc ccctgaaaag gctgtttaag ttgggtaaac cgctcccagc cgacgacgag    8280
caagacgaag acagaagacg cgctctgcta gatgaaacaa aggcgtggtt tagagtaggt    8340
ataacaggca ctttagcagt ggccgtgacg acccggtatg aggtagacaa tattacacct    8400
gtcctactgg cattgagaac ttttgcccag agcaaaagag cattccaagc catcagaggg    8460
gaaataaagc atctctacgg tggtcctaaa tagtcagcat agtacatttc atctgactaa    8520
tactacaaca ccaccacctc tagacgcgta gatctcacgt gagcatgcag gccttgggcc    8580
caatgatccg accagcaaaa ctcgatgtac ttccgaggaa ctgatgtgca taatgcatca    8640
ggctggtaca ttagatcccc gcttaccgcg ggcaatatag caacactaaa aactcgatgt    8700
acttccgagg aagcgcagtg cataatgctg cgcagtgttg ccacataacc actatattaa    8760
ccatttatct agcggacgcc aaaaactcaa tgtatttctg aggaagcgtg gtgcataatg    8820
ccacgcagcg tctgcataac ttttattatt tcttttatta atcaacaaaa ttttgttttt    8880
aacatttcaa aaaaaaaaaa aaaaaaaaa aaaaaaaaa aaaaagggaa ttcccaactt    8940
gtttattgca gcttataatg gttacaaata aagcaatagc atcacaaatt tcacaaataa    9000 agcattttt tcactgcatt ctagttgtgg tttgtccaaa ctcatcaatg tatcttatca    9060
tgtctggatc cgtcgagacg cgtccaattc gccctatagt gagtcgtatt acgcgcgctt    9120
ggcgtaatca tggtcatagc tgtttcctgt gtgaaattgt tatccgctca caattccaca    9180
caacatacga gccggaagca taaagtgtaa agcctgggt gcctaatgag tgagctaact    9240
cacattaatt gcgttcgct cactgcccgc tttccagtcg ggaaacctgt cgtgccagct    9300
gcattaatga atcggccaac gcgcggggag aggcggtttg cgtattgggc gctcttccgc    9360
```

```
ttcctcgctc actgactcgc tgcgctcggt cgttcggctg cggcgagcgg tatcagctca   9420
ctcaaaggcg gtaatacggt tatccacaga atcaggggat aacgcaggaa agaacatgtg   9480
agcaaaaggc cagcaaaagg ccaggaaccg taaaaaggcc gcgttgctgg cgttttttcca  9540 taggctccgc ccccctgacg agcatcacaa aaatcgacgc tcaagtcaga ggtggcgaaa   9600
cccgacagga ctataaagat accaggcgtt tccccctgga agctccctcg tgcgctctcc   9660
tgttccgacc ctgccgctta ccggatacct gtccgccttt ctcccttcgg aagcgtggc    9720 gctttctcaa tgctcacgct gtaggtatct cagttcggtg taggtcgttc gctccaagct   9780
gggctgtgtg cacgaacccc ccgttcagcc cgaccgctgc gccttatccg gtaactatcg   9840
tcttgagtcc aacccggtaa gacacgactt atcgccactg gcagcagcca ctggtaacag   9900
gattagcaga gcgaggtatg taggcggtgc tacagagttc ttgaagtggt ggcctaacta   9960
cggctacact agaaggacag tatttggtat ctgcgctctg ctgaagccag ttaccttcgg  10020
aaaaagagtt ggtagctctt gatccggcaa acaaaccacc gctggtagcg gtggtttttt  10080
tgtttgcaag cagcagatta cgcgcagaaa aaaggatct caagaagatc ctttgatctt   10140
ttctacgggg tctgacgctc agtggaacga aaactcacgt taagggattt tggtcatgag  10200
attatcaaaa aggatcttca cctagatcct tttaaattaa aaatgaagtt ttaaatcaat  10260
ctaaagtata tatgagtaaa cttggtctga cagttaccaa tgcttaatca gtgaggcacc  10320
tatctcagcg atctgtctat ttcgttcatc catagttgcc tgactccccg tcgtgtagat  10380
aactacgata cgggagggct taccatctgg ccccagtgct gcaatgatac cgcgagaccc  10440
acgctcaccg gctccagatt tatcagcaat aaaccagcca gccggaaggg ccgagcgcag  10500
aagtggtcct gcaactttat ccgcctccat ccagtctatt aattgttgcc gggaagctag  10560
agtaagtagt tcgccagtta atagtttgcg caacgttgtt gccattgcta caggcatcgt  10620
ggtgtcacgc tcgtcgtttg gtatggcttc attcagctcc ggttcccaac gatcaaggcg  10680
agttacatga tcccccatgt tgtgcaaaaa agcggttagc tccttcggtc ctccgatcgt  10740
tgtcagaagt aagttggccg cagtgttatc actcatggtt atggcagcac tgcataattc  10800
tcttactgtc atgccatccg taagatgctt ttctgtgact ggtgagtact caaccaagtc  10860
attctgagaa tagtgtatgc ggcgaccgag ttgctcttgc ccggcgtcaa tacgggataa  10920
taccgcgcca catagcagaa ctttaaaagt gctcatcatt ggaaaacgtt cttcggggcg  10980
aaaactctca aggatcttac cgctgttgag atccagttcg atgtaaccca ctcgtgcacc  11040
caactgatct tcagcatctt ttactttcac cagcgtttct gggtgagcaa aaacaggaag  11100
gcaaaatgcc gcaaaaaagg gaataagggc gacacggaaa tgttgaatac tcatactctt  11160
cctttttcaa tattattgaa gcatttatca gggttattgt ctcatgagcg gatacatatt  11220
tgaatgtatt tagaaaaata aacaaatagg ggttccgcgc acatttcccc gaaaagtgcc  11280
ac                                                                 11282

<210> SEQ ID NO 2
<211> LENGTH: 30
<212> TYPE: DNA
<213> ORGANISM: Enh-FOR

<400> SEQUENCE: 2
gttttctcga gcctccaaat cccctggctc                                      30

<210> SEQ ID NO 3
```

-continued

<210> SEQ ID NO 3
<211> LENGTH: 38
<212> TYPE: DNA
<213> ORGANISM: Enh-FOR2

<400> SEQUENCE: 3
cctccggatc cgtcgagcct ccaaatcccc tggctctg                              38

<210> SEQ ID NO 4
<211> LENGTH: 25
<212> TYPE: DNA
<213> ORGANISM: Enh-REV

<400> SEQUENCE: 4
agaggtacct ccaaccgcac ctgtg                                            25

<210> SEQ ID NO 5
<211> LENGTH: 41
<212> TYPE: DNA
<213> ORGANISM: Enh-REV2

<400> SEQUENCE: 5
ggtggggtac cgcggccgca tcctctgagc tcaggagttt g                          41

<210> SEQ ID NO 6
<211> LENGTH: 30
<212> TYPE: DNA
<213> ORGANISM: Epo3'-FOR

<400> SEQUENCE: 6
gctgtctaga gagcaactct gagatctaag                                       30

<210> SEQ ID NO 7
<211> LENGTH: 52
<212> TYPE: DNA
<213> ORGANISM: EPO3'-FOR2

<400> SEQUENCE: 7
ggggagctcg cggccgcaag cttggtgggt cgaccaggtg tgtccacctg gg              52

<210> SEQ ID NO 8
<211> LENGTH: 30
<212> TYPE: DNA
<213> ORGANISM: EPO3'-REV

<400> SEQUENCE: 8
ccaaccctcg aggccagccc ccatcctgtc                                       30

<210> SEQ ID NO 9
<211> LENGTH: 31
<212> TYPE: DNA
<213> ORGANISM: EPO5'-FOR

<400> SEQUENCE: 9
caacaccacc accagagtcc ctgggccacc c                                     31

<210> SEQ ID NO 10
<211> LENGTH: 22
<212> TYPE: DNA
<213> ORGANISM: EPO5'-REV

<400> SEQUENCE: 10
ggacattcta gaacagatag cc                                               22

-continued

```
<210> SEQ ID NO 11
<211> LENGTH: 55
<212> TYPE: DNA
<213> ORGANISM: EPO5'-REV2

<400> SEQUENCE: 11
ggtgggtacc gcggccgcaa gcttggttgg ctcgaggctc cgcgcctggc cgggg        55

<210> SEQ ID NO 12
<211> LENGTH: 90
<212> TYPE: DNA
<213> ORGANISM: HDV-FOR

<400> SEQUENCE: 12
aattcgggtc ggcatggcat ctccacctcc tcgcggtccg acctgggcat ccgaaggagg    60
acgcacgtcc actcggatgg ctaagggagc                                     90

<210> SEQ ID NO 13
<211> LENGTH: 90
<212> TYPE: DNA
<213> ORGANISM: HDV-REV

<400> SEQUENCE: 13
aattgctccc ttagccatcc gagtggacgt gcgtcctcct tcggatgccc aggtcggacc    60
gcgaggaggt ggagatgcca tgccgacccg                                     90

<210> SEQ ID NO 14
<211> LENGTH: 35
<212> TYPE: DNA
<213> ORGANISM: Pepo-FOR

<400> SEQUENCE: 14
cccgagctcg cggccgctgg gcttccagac ccagc                               35

<210> SEQ ID NO 15
<211> LENGTH: 43
<212> TYPE: DNA
<213> ORGANISM: Pepo-FOR2

<400> SEQUENCE: 15
ggttgggagc tcgcggccgc gttactgctg attagtatct tgc                      43

<210> SEQ ID NO 16
<211> LENGTH: 83
<212> TYPE: DNA
<213> ORGANISM: Pepo-REV

<400> SEQUENCE: 16
cccggatccc ctcccaattg gtcggctgtt tgattcaata gtgtgtacta cgccgtcaat    60
gcggctctgg ccggggtcg ggg                                             83

<210> SEQ ID NO 17
<211> LENGTH: 49
<212> TYPE: DNA
<213> ORGANISM: Psub-FOR

<400> SEQUENCE: 17
ggggagctcg cggccgcgga ggagcgctga ttcggttact tccacagcg                49

<210> SEQ ID NO 18
<211> LENGTH: 42
<212> TYPE: DNA
```

-continued

<213> ORGANISM: Psub-REV

<400> SEQUENCE: 18
cggggtggcc cagggactct ggtggtggtg ttgtagtatt ag          42

<210> SEQ ID NO 19
<211> LENGTH: 38
<212> TYPE: DNA
<213> ORGANISM: SIN3'-FOR

<400> SEQUENCE: 19
ccaaccaagc ttgtcgacgc cccaatgatc cgaccagc               38

<210> SEQ ID NO 20
<211> LENGTH: 30
<212> TYPE: DNA
<213> ORGANISM: SV40-REV

<400> SEQUENCE: 20
ctcgacggct cgagacatga taagatacat                        30

<210> SEQ ID NO 21
<211> LENGTH: 41
<212> TYPE: DNA
<213> ORGANISM: Enh-FOR2

<400> SEQUENCE: 21
cctccggatc cgtcgagcct ccaaatcccc tggctctgtc c           41

<210> SEQ ID NO 22
<211> LENGTH: 46
<212> TYPE: DNA
<213> ORGANISM: Enh-REV2

<400> SEQUENCE: 22
ggtggggtac cgcggccgca tcctctgagc tcaggagttt gagacc      46

<210> SEQ ID NO 23
<211> LENGTH: 41
<212> TYPE: DNA
<213> ORGANISM: EPO3'-FOR3

<400> SEQUENCE: 23
ggggagctcg cggccgccag gtgtgtccac ctgggcatat c           41

<210> SEQ ID NO 24
<211> LENGTH: 36
<212> TYPE: DNA
<213> ORGANISM: EPO5'-REV3

<400> SEQUENCE: 24
ggtgggtacc gcggccgcct ccgcgcctgg ccgggg                 36

<210> SEQ ID NO 25
<211> LENGTH: 27
<212> TYPE: DNA
<213> ORGANISM: EPO5'un-FOR

<400> SEQUENCE: 25
cgcaagctta gagtccctgg gccaccc                           27

<210> SEQ ID NO 26
<211> LENGTH: 30

-continued

```
<212> TYPE: DNA
<213> ORGANISM: -HDV

<400> SEQUENCE: 26
ctaagggagg aattcccaac ttgtttattg                              30

<210> SEQ ID NO 27
<211> LENGTH: 26
<212> TYPE: DNA
<213> ORGANISM: nhnsPEco-REV

<400> SEQUENCE: 27
ggaaaagcgc taaaagaggc tgggac                                  26

<210> SEQ ID NO 28
<211> LENGTH: 25
<212> TYPE: DNA
<213> ORGANISM: nhPEPOnot-FOR

<400> SEQUENCE: 28
ccgcggtggc ggccgctggg cttcc                                   25

<210> SEQ ID NO 29
<211> LENGTH: 31
<212> TYPE: DNA
<213> ORGANISM: nhPEPOtRNA-FOR

<400> SEQUENCE: 29
ccagagccgc atatagtggt gagtatcccc g                            31

<210> SEQ ID NO 30
<211> LENGTH: 31
<212> TYPE: DNA
<213> ORGANISM: nhPEPOtRNA-REV

<400> SEQUENCE: 30
caccactata tgcggctctg gccgggggtc g                            31

<210> SEQ ID NO 31
<211> LENGTH: 39
<212> TYPE: DNA
<213> ORGANISM: notsin5'-FOR

<400> SEQUENCE: 31
gcgcgcgcgg ccgcattgac ggcgtagtac acactattg                    39

<210> SEQ ID NO 32
<211> LENGTH: 29
<212> TYPE: DNA
<213> ORGANISM: Pepo-FORX

<400> SEQUENCE: 32
caacccaggc gtcctgcccc tgctctgac                               29

<210> SEQ ID NO 33
<211> LENGTH: 29
<212> TYPE: DNA
<213> ORGANISM: PEPOHIIIFOR

<400> SEQUENCE: 33
cctaaagctt ctgggcttcc agacccagc                               29

<210> SEQ ID NO 34
```

```
<211> LENGTH: 26
<212> TYPE: DNA
<213> ORGANISM: PEPOHIIIREV

<400> SEQUENCE: 34
gggtctggaa gcccagaagc tttagg                                         26

<210> SEQ ID NO 35
<211> LENGTH: 52
<212> TYPE: DNA
<213> ORGANISM: PEPOlongFOR3

<400> SEQUENCE: 35
cgcggtacca tgcggccgcg ttactgctga ttagtatctt gctaatcata gg            52

<210> SEQ ID NO 36
<211> LENGTH: 53
<212> TYPE: DNA
<213> ORGANISM: PEPOlongFOR4

<400> SEQUENCE: 36
ggttgggagc tcgcggccgc gttactgctg attagtatct tgctaatcat agg           53

<210> SEQ ID NO 37
<211> LENGTH: 31
<212> TYPE: DNA
<213> ORGANISM: PEPOlongREV

<400> SEQUENCE: 37
cggctcgagg cggctctggc cggggggtcgg g                                   31

<210> SEQ ID NO 38
<211> LENGTH: 28
<212> TYPE: DNA
<213> ORGANISM: PEPOlongREV3

<400> SEQUENCE: 38
cggctcgagg cggctctggc cggggtc                                        28

<210> SEQ ID NO 39
<211> LENGTH: 27
<212> TYPE: DNA
<213> ORGANISM: Pepo-REV3

<400> SEQUENCE: 39
cacccggggt cagagcaggg gcaggac                                        27

<210> SEQ ID NO 40
<211> LENGTH: 35
<212> TYPE: DNA
<213> ORGANISM: Pepo-REVY

<400> SEQUENCE: 40
ctgtacaagg atccgtgcaa ttggtcggct gtttg                               35

<210> SEQ ID NO 41
<211> LENGTH: 30
<212> TYPE: DNA
<213> ORGANISM: rrEPO5'-FOR

<400> SEQUENCE: 41
ggcgcggaga tgggggtgca cggtgagtac                                     30
```

-continued

<210> SEQ ID NO 42
<211> LENGTH: 23
<212> TYPE: DNA
<213> ORGANISM: rrEPO5'-REV

<400> SEQUENCE: 42
gacattctag aacagatagc cag                                               23

<210> SEQ ID NO 43
<211> LENGTH: 22
<212> TYPE: DNA
<213> ORGANISM: rrNSPHPA-FOR

<400> SEQUENCE: 43
tatggcgtta accggtctga tg                                                22

<210> SEQ ID NO 44
<211> LENGTH: 44
<212> TYPE: DNA
<213> ORGANISM: rrNSPSOE

<400> SEQUENCE: 44
cgtgcacccc catctccgcg ccggtggtgg tgttgtagta ttag                         44

<210> SEQ ID NO 45
<211> LENGTH: 21
<212> TYPE: DNA
<213> ORGANISM: 3'sineco47

<400> SEQUENCE: 45
gcaaagaggt cgtccatacg g                                                 21

<210> SEQ ID NO 46
<211> LENGTH: 32
<212> TYPE: DNA
<213> ORGANISM: subfor

<400> SEQUENCE: 46
gcgcggagct ctgaggtaga caatattaca cc                                     32

<210> SEQ ID NO 47
<211> LENGTH: 32
<212> TYPE: DNA
<213> ORGANISM: subrev

<400> SEQUENCE: 47
gcgcggagct ctcaggcacc gggcttgcgg gt                                     32

<210> SEQ ID NO 48
<211> LENGTH: 39
<212> TYPE: DNA
<213> ORGANISM: 5'SV40 PUR

<400> SEQUENCE: 48
acgtacgcgt gcggccgcgt tagggtgtgg aaagtcccc                              39

<210> SEQ ID NO 49
<211> LENGTH: 43
<212> TYPE: DNA
<213> ORGANISM: SV40puro-REV

<400> SEQUENCE: 49
gcgcgcggcc gcttaattaa tggacaaacc acaactagaa tgc                         43

REPLICON BASED ACTIVATION OF ENDOGENOUS GENES

CROSS-REFERENCE TO RELATED APPLICATIONS

This application claims the benefit of the filing date of provisional application 60/169,988, filed on Dec. 10, 1999, the entire disclosure of which is incorporated herein by reference.

BACKGROUND OF THE INVENTION

1. Field of the Invention

The present invention relates to methods for modifying the genomes of eukaryotic cells to alter the expression of selected endogenous genes. The invention also relates to polypeptides and recombinant eukaryotic host cells produced by the practice of the disclosed methods. The invention further relates to vector systems useful for modifying the genomes of eukaryotic cells to alter the expression of selected endogenous genes.

2. Related Art

A considerable number of diseases are based on impaired gene regulation leading to the loss of appropriate responses to certain physiological conditions due to lack of production of appropriate factors (e.g., hormones, blood clotting factors). A number of factors have been isolated in the past from organs and bodily fluids, such as urine, for use in the treatment of such diseases. Several disadvantages are implicit to such isolation regimens. First, relatively large amounts of raw material are required to obtain relatively small amounts of purified substance. Secondly, when the factors are derived from non-human organisms, they often elicited undesired side-reactions upon administration to humans.

Progress in gene technology has allowed for the cloning of genes and the in vitro production of encoded proteins. These production processes are generally performed by cloning the gene of interest into an appropriate expression vector and introducing the latter into suitable cells.

An alternative approach to producing gene products is to directly increase expression of the endogenous gene in an appropriate cell line. This approach obviates the necessity of isolating the endogenous gene from the cell in which it resides.

Gene expression can be modified at several levels, e.g., by manipulating the efficiencies of transcription, translation, protein folding or secretion. We present methods for increasing expression of endogenous genes by keeping transcription efficiency constant but increasing the amount of mRNA within the cell using RNA replication.

SUMMARY OF THE INVENTION

The present invention provides both methods and nucleic acid constructs for altering the expression characteristics of endogenous target genes in eukaryotic cells. Further provided are recombinant eukaryotic host cells which are produced by the methods of the invention and gene expression products produced using the recombinant eukaryotic host cells.

In particular, the invention provides methods for modifying the expression characteristics of endogenous target genes within the genomes of eukaryotic cells comprising inserting into these genomes exogenous nucleic acid which encodes genetic elements required for RNA replication and amplifying RNA corresponding to the coding region of the endogenous target genes.

In one general aspect, the invention provides methods for modifying the expression characteristics of endogenous target genes within the genome of eukaryotic cells comprising inserting exogenous polynucleotides in the 5' and 3' regions flanking the endogenous target genes to produce recombinant eukaryotic host cells, and culturing the recombinant eukaryotic host cell under conditions which allow for transcription and replication of RNA corresponding to the endogenous target genes, wherein the exogenous polynucleotides encode genetic elements required for RNA replication.

In another general aspect, the invention provides methods for producing polypeptides encoded by endogenous target genes of eukaryotic cells comprising inserting exogenous polynucleotides in the 5' and 3' regions flanking the endogenous target genes to produce recombinant eukaryotic host cells, and culturing the recombinant eukaryotic host cells under conditions which allow for transcription, replication, and translation of RNA corresponding to the endogenous target genes, wherein the exogenous polynucleotides encode genetic elements required for RNA replication which alter the expression characteristics of the endogenous target genes.

In a related aspect, the exogenous polynucleotides used in the methods of the invention contain one or more positive or negative selection markers (e.g., neomycin phosphotransferase, metallothionein I, metallothionein II, dihydrofolate reductase, hygromycin B phosphotransferase, puromycin-N-acetyl-transferase, xanthine/guanine phosphoribosyl transferase, histidinol dehydrogenase, Herpes simplex thymidine kinase, cytosine deaminase, Diptheria toxin, and hypoxanthine phosphoribosyl transferase).

Further, these selection markers may be operably linked to a viral subgenomic promoter or an RNA polymerase II promoter.

In addition, when the selection marker is a positive selection marker, this marker may be co-transcribed with the coding region of the endogenous target gene as part of the same RNA molecule and translated from an internal ribosome entry site.

Further, when negative selection markers are used, these markers will generally be positioned in the exogenous polynucleotides such that they are excised when integration occurs by homologous recombination.

In another related aspect, the exogenous polynucleotides which encode genetic elements required for RNA replication are derived from an Alphavirus.

In yet another related aspect, the methods of the invention result in the production of recombinant eukaryotic host cells wherein the endogenous target genes with modified expression characteristics are operably linked to an Alphavirus subgenomic promoter.

In further related aspects the recombinant eukaryotic host cells generated by the methods of the invention are animal cells, vertebrate cells, mammalian cells, and/or human cells. Further, when the recombinant eukaryotic host cells are human cells, these cells may be derived from organs such as the kidney, liver, or testes. In addition, when the recombinant eukaryotic host cells are human liver cells, these cells may be Hep G2 cells, Hep 3B cells, or a cell type which is a derivative thereof. In addition, when the recombinant eukaryotic host cells are human kidney cells, these cells may be 293 cells, or a cell type which is a derivative thereof.

The invention further relates to methods for modifying the expression characteristics of selected endogenous genes, referred to herein as endogenous target genes, which encode ribozymes and polypeptides. When the expression of an endogenous target gene is modified by the methods of the invention, this gene may encode a human polypeptide such as erythropoietin, antithrombin III. α-galactosidase, granulocyte-macrophage colony-stimulating factor. megakaryocyte-growth factor (M-GF), blood clotting factor VII, blood clotting factor VIII, blood clotting factor IX, α-interferon, β-interferon, γ-interferon, interleukin-2, tissue plasminogen activator, thrombopoietin, α I-antitrypsin, LDL-receptor, insulin, or growth hormone.

The invention also relates to recombinant eukaryotic host cells produced by the methods of the invention.

In another general aspect, the invention provides DNA vector systems for modifying the expression characteristics of selected endogenous genes within the genomes of eukaryotic cells. These vector systems comprise 5' targeting constructs and 3' targeting constructs which contain genetic elements required for RNA replication.

In a related aspect, the 5' and 3' targeting constructs of the vector systems of the invention contain genetic elements of an Alphavirus. Further, these genetic elements may be derived from Semliki Forest Virus, Sindbis virus, Venezuelan equine encephalomyelitis virus, or Ross River Virus.

In another related aspect, the 5' and 3' targeting constructs of the vector systems of the invention may contain one or more positive or negative selection markers (e.g., neomycin phosphotransferase, metallothionein I, metallothionein II, dihydrofolate reductase, hygromycin B phosphotransferase. puromycin-N-acetyl-transferase, xanthine/guanine phosphoribosyl transferase, histidinol dehydrogenase, Herpes simplex thymidine kinase, cytosine deaminase, Diptheria toxin, and hypoxanthine phosphoribosyl transferase). Further, these selection markers may be operably linked to a viral subgenomic promoter or to an internal ribosome entry site (IRES).

The 3' targeting construct (2) contains the following subcomponents: (a) a 5' targeting sequence (3' untransl.), (b) a 3' cis-acting replication element, (c) nucleic acid encoding a polyA stretch ($A_n$), (d) nucleic acid encoding a Hepatitis delta virus antigenomic ribozyme (HDV), (e) a transcription terminator and polyadenylation signal (T/pA), (f) a resistance marker (resistance) operably linked to an RNA polymerase II promoter (not shown), and (g) a 3' targeting sequence.

Integration of the 5' and 3' constructs by homologous recombination events (4) at a specified chromosomal locus (3) results in the alteration of this chromosomal locus (5).

Figure 1:
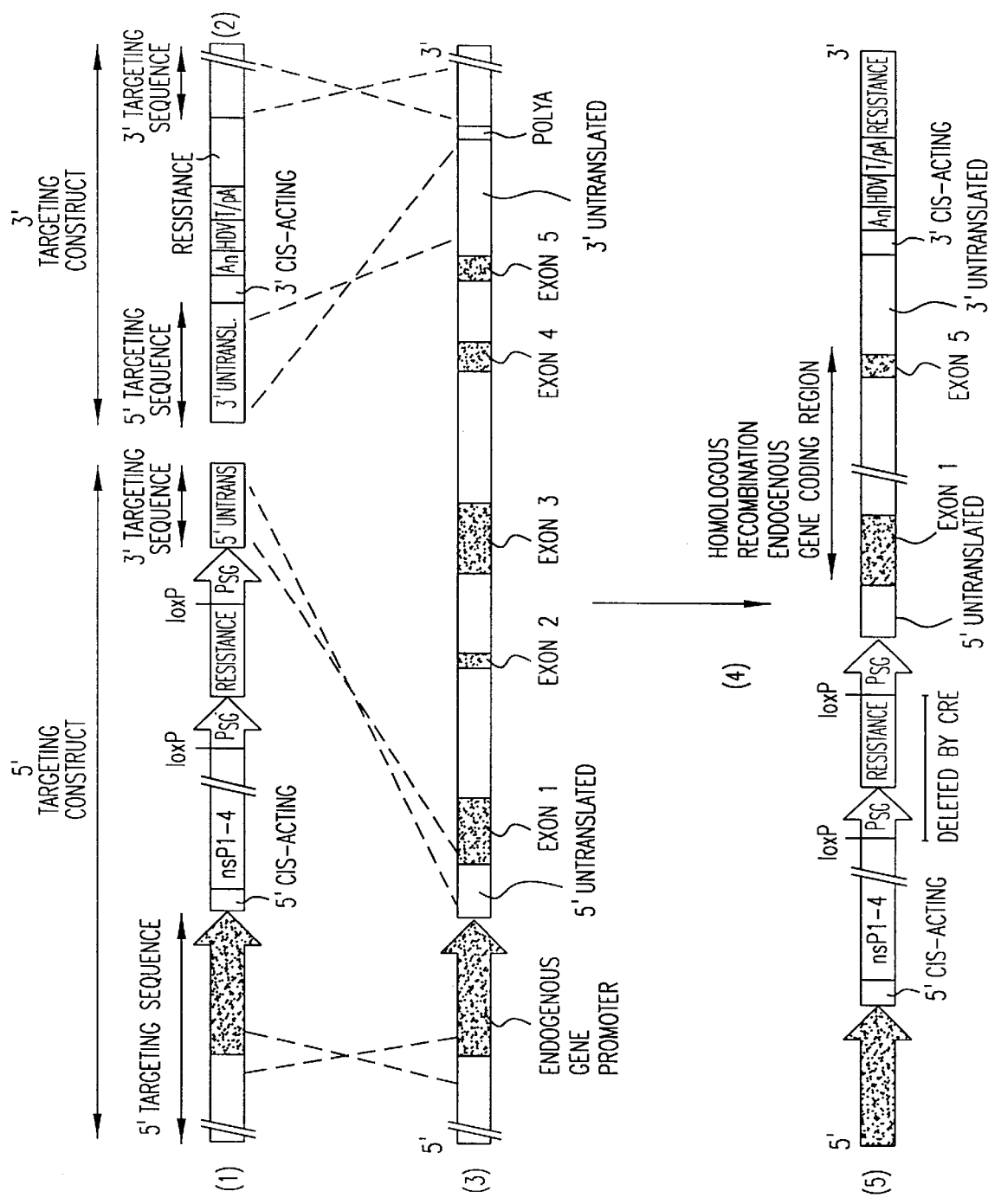
FIG. 1 shows a general overview of specific embodiments of the invention. In this embodiment, homologous recombination is performed using a two component vector system. This two component vector system consists of a 5' targeting construct (1) and a 3' targeting construct (2). The 5' targeting construct (1) contains the following subcomponents: (a) a 5' targeting sequence, (b) a 5' cis-acting replication element which, in conjunction with a 3' cis-acting replication element, allows for multiple rounds of RNA amplification, (c) nucleic acid encoding Alphaviral non-structural proteins 1–4 (nsP1–4), (d) a resistance marker cassette, consisting of a resistance marker operably linked to a first Alphaviral subgenomic promoter ($P_{SG}$), both of which are located between two loxP recombination sites, (e) a second subgenomic promoter ($P_{SG}$), and (f) a 3' targeting sequence (5' untrans).
Figure 2:
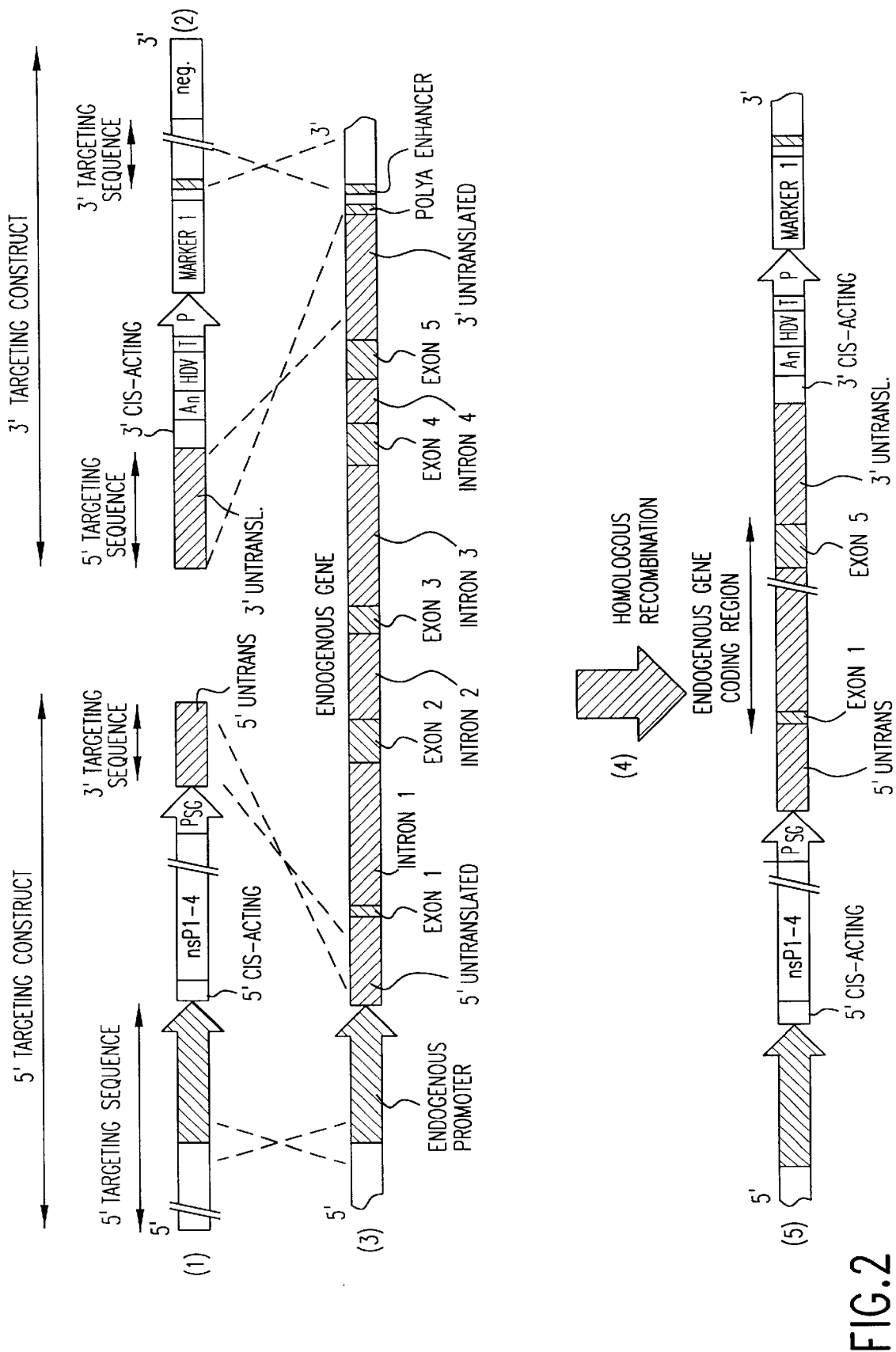

FIG. 2 shows a general overview of other embodiments of the invention which are similar to those shown in FIG. 1. One difference between the embodiments shown in FIG. 1 and FIG. 2 is that the 3' targeting construct of FIG. 2 contains a negative selection marker (neg.) located 3' to the 3' targeting sequence. As explained below, this negative selection marker can be used to distinguish cells in which the 3' targeting construct has integrated by homologous recombination from cells in which this construct has integrated by non-homologous recombination.

Abbreviations in FIG. 2 are as follows: 5' cis-acting replication element (5'), 3' cis-acting replication element (3'), 5' untranslated region of the endogenous target gene (5' untrans), 3' untranslated region of the endogenous target gene (3' untransl.), positive selection marker (marker 1), negative selection marker (neg.), nucleic acid encoding non-structural proteins 1–4 (nsP 1–4), nucleic acid encoding and corresponding to a 37 nucleotide stretch of adenine residues ($A_n$), nucleic acid encoding the Hepatitis delta virus antigenomic ribozyme (HDV), subgenomic promoter ($P_{SG}$), transcriptional terminator and polyadenylation signal (T), and an RNA polymerase II promoter (P).

Figure 3:
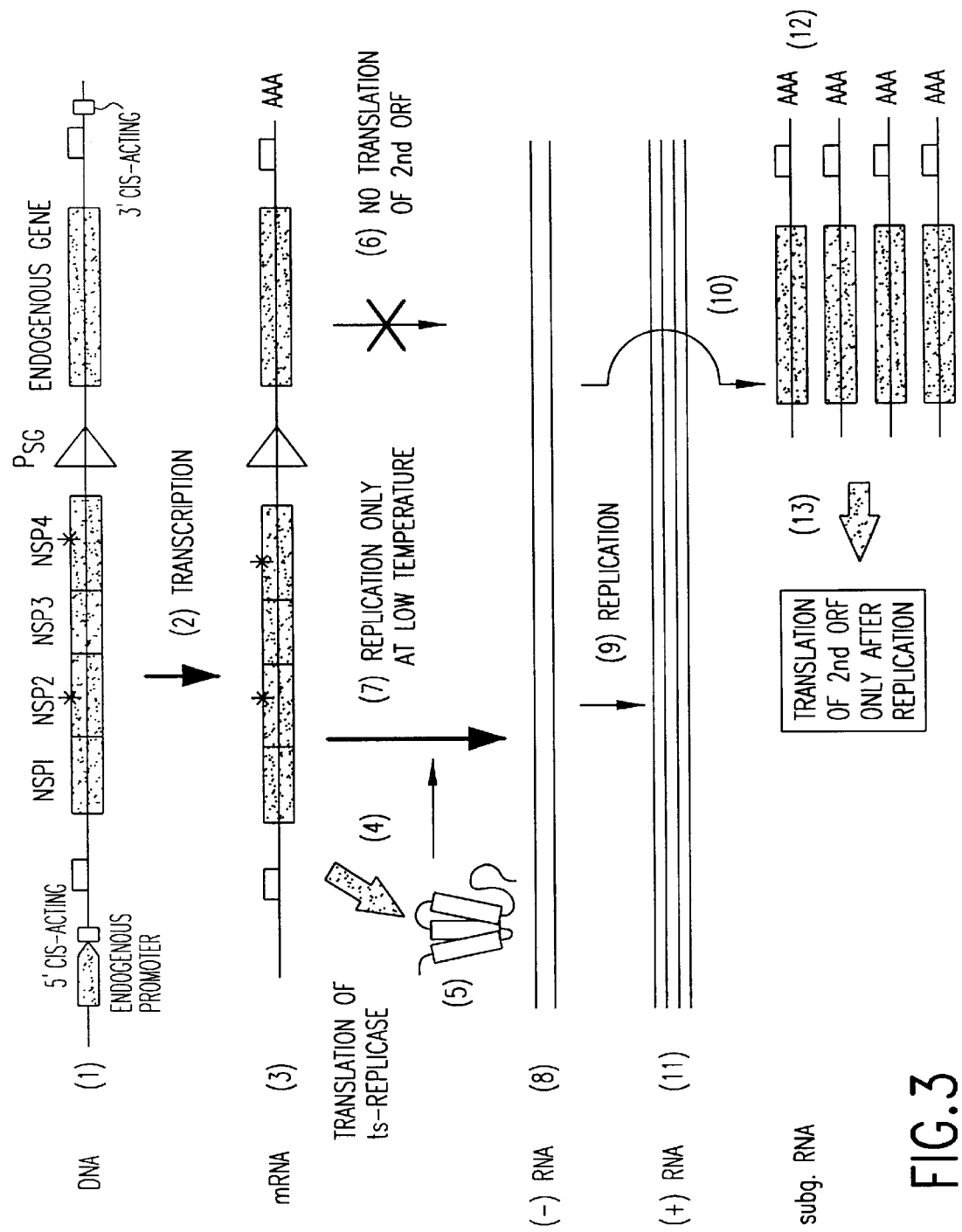

FIG. 3 provides a schematic representation of the expression of an endogenous target gene from a chromosomal locus (1) which contains components of an RNA vector system of the invention. The endogenous promoter (solid horizontal arrow) drives transcription (2) into mRNA (3). Translation (4) of the first open reading frame (ORF) of the mRNA results in the production of a temperature-sensitive replicase (ts-replicase protein) (5). However, the RNA of the second ORF, containing RNA corresponding to the endogenous target gene, is not accessible to ribosomes. Thus, no translation (6) of this RNA occurs. At low temperature the ts-replicase catalyzes replication (7) of the mRNA (3) into full-length (–) strand RNA (8). The ts-replicase also catalyzes subsequent replications (9, 10) into full-length (+) strand RNA (11) and subgenomic RNA (12). Subgenomic RNA (12) is then translated (13) into the protein encoded by the endogenous target gene.

Abbreviations in FIG. 3 are as follows: cis-acting replication elements (cis-acting), non-structural proteins 1–4 (nsP1, nsP2, nsP3, nsP4), and subgenomic promoter ($P_{SG}$). Nucleic acid encoding packaging signals is present but not specifically identified in FIG. 3.

Figure 4:
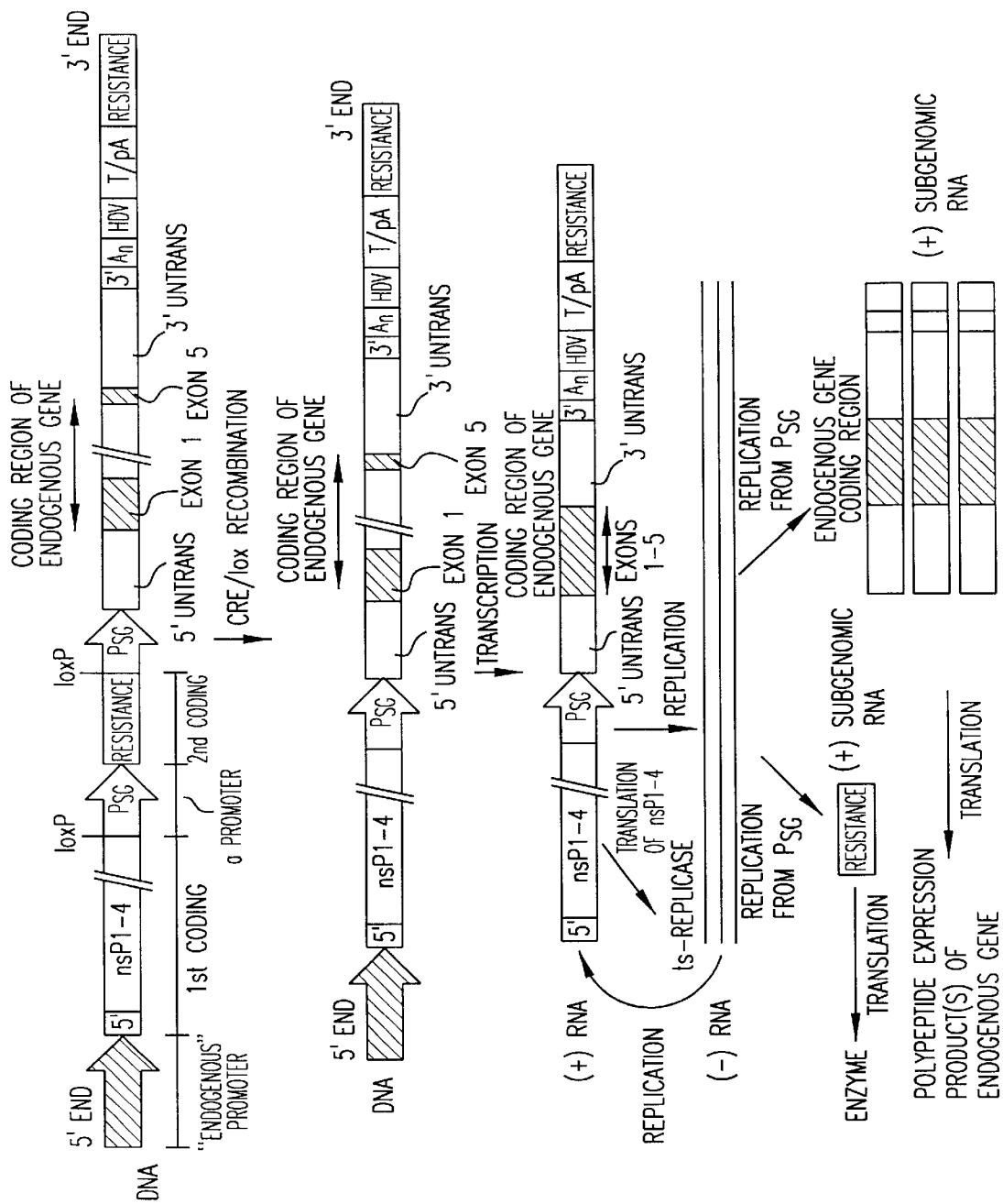

FIG. 4, like FIG. 3, shows the expression of an endogenous target gene from a chromosomal locus. In this schematic, the 3' targeting construct contains nucleic acid encoding and corresponding to a polyA stretch ($A_n$) and a Hepatitis delta virus antigenomic ribozyme (HDV). This schematic further shows the deletion of a subgenomic promoter and positive marker using a CRE/loxP recombination system. (See Sauer, U.S. Pat. No. 4,959,317.)

Additional abbreviations used in FIG. 4 are as follows: nucleic acid encoding non-structural proteins 1–4 (nsP 1–4), 5' cis-acting replication elements (5'), 3' cis-acting replication elements (3'), 5' untranslated region of the endogenous target gene (5' untrans), 3' untranslated region of the endogenous target gene (3' untrans), a transcription terminator and polyadenylation signal (T/pA), positive selection marker (resistance) operably linked to an RNA polymerase II promoter, and subgenomic promoter ($P_{SG}$).

Figure 5A:
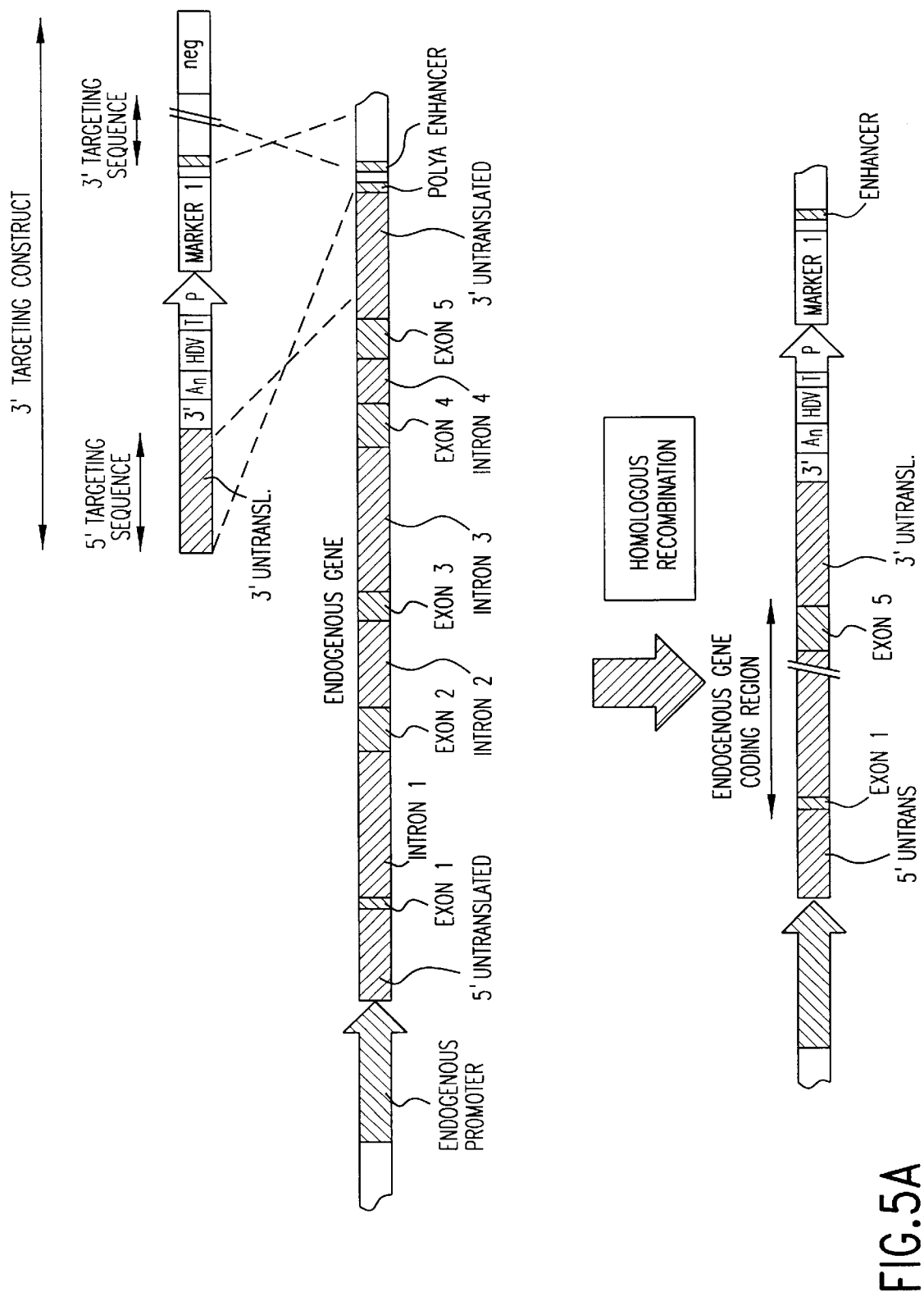
Figure 5B:
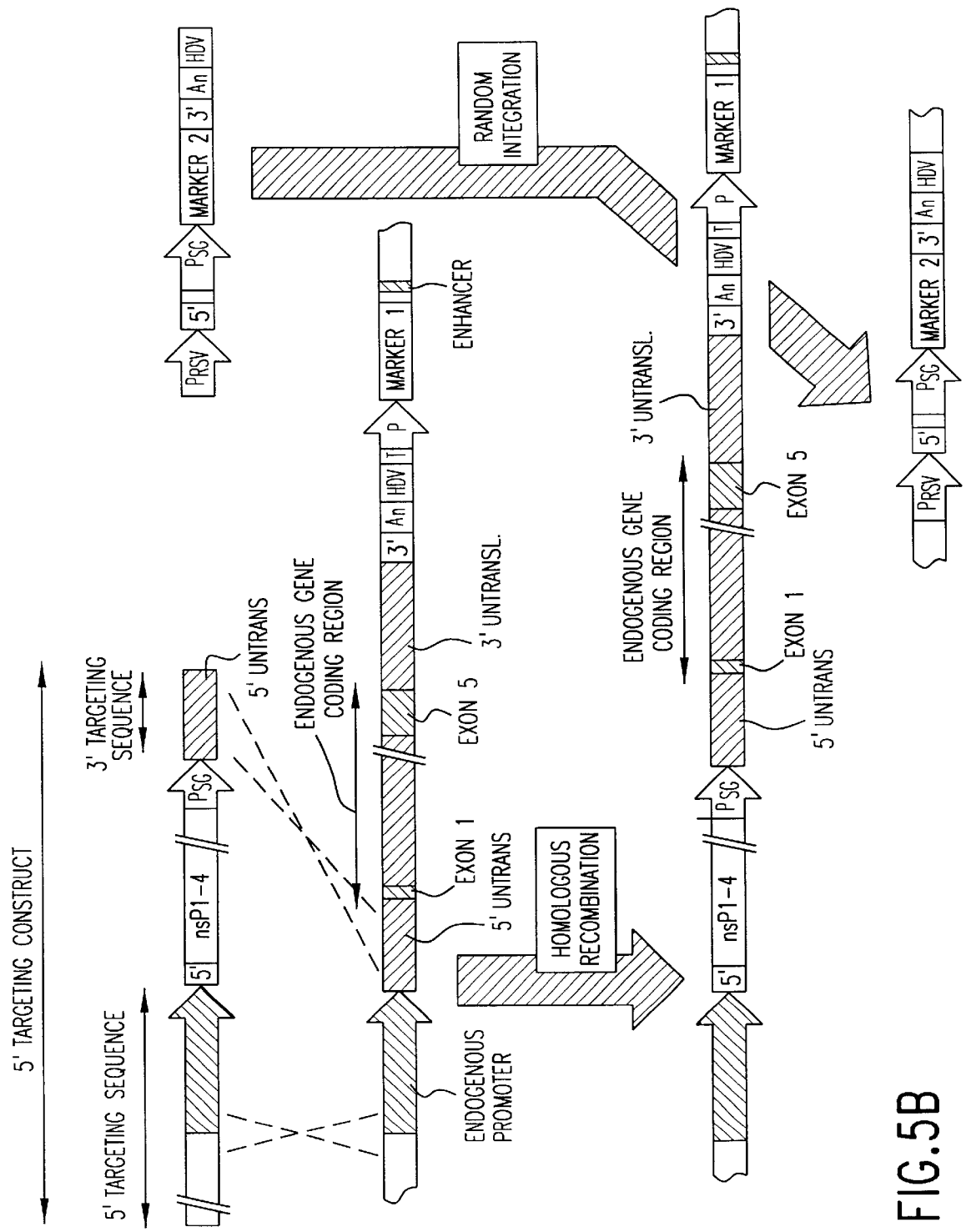

FIGS. 5A–5B show a positive-negative selection scheme for identifying cells which have undergone homologous recombination in regions both 5' and 3' to an endogenous target gene on the same allele. Unlike the vector system shown in FIG. 2, both of the targeting constructs shown in FIGS. 5A–5B contain negative selection markers. Further, in the scheme shown in FIGS. 5A–5B, a positive selection marker, which is operably linked to subgenomic promoter, is inserted into cellular nucleic acid by random integration. Thus, as explained in detail below, this positive selection marker will only be expressed in the presence of the nsP1–4 gene products.

Abbreviations in FIGS. 5A–5B are as follows: positive selection markers (marker 1 and marker 2), negative selection marker (neg.), nucleic acid encoding and corresponding to a 37 nucleotide stretch of adenine residues ($A_n$), nucleic acid encoding the Hepatitis delta virus antigenomic ribozyme (HDV), 5' cis-acting replication elements (5'), 3' cis-acting replication elements (3'), subgenomic promoter ($P_{SG}$), Rous sarcoma virus promoter ($R_{RSV}$), a transcription terminator and polyadenylation signal (T/pA), and an RNA polymerase II promoter (P).

Figure 6B:
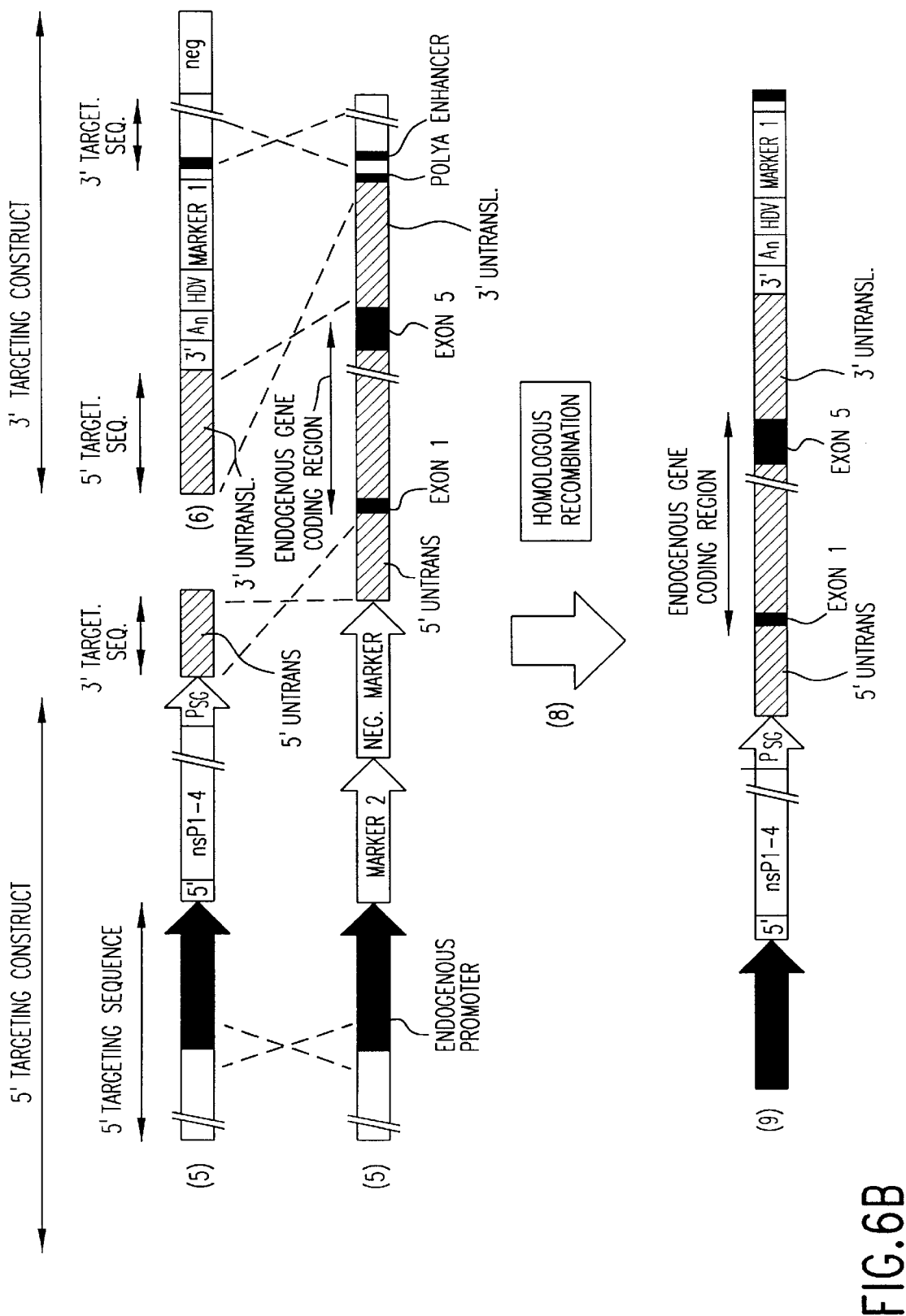

FIGS. 6A–6B show an embodiment of the invention when three targeting constructs integrate into the endogenous target gene locus. The first vector construct (1) integrates 5' to the endogenous target gene coding region and contains both positive and negative selection markers. The second vector construct (5) replaces the first vector construct (1) via homologous recombination and cells where the replacement has occurred are identified by negative selection. The third vector construct (6) contains positive and negative selection markers in locations designed to differentiate between cells where the construct has integrated by homologous and non-homologous recombination.

Abbreviations in FIGS. 6A–6B are as follows: positive selection markers (marker 1 and marker 2), negative selection markers (neg. and neg. marker), nucleic acid encoding non-structural proteins 1–4 (nsP 1–4), nucleic acid encoding and corresponding to a 37 nucleotide stretch of adenine residues ($A_n$), nucleic acid encoding the Hepatitis delta virus antigenomic ribozyme (HDV), 5' untranslated region of the endogenous target gene (5' untrans), 3' untranslated region of the endogenous target gene (3' untransl.), 5' cis-acting replication elements (5'), 3' cis-acting replication elements (3'), and subgenomic promoter ($P_{SG}$).

Figure 7:
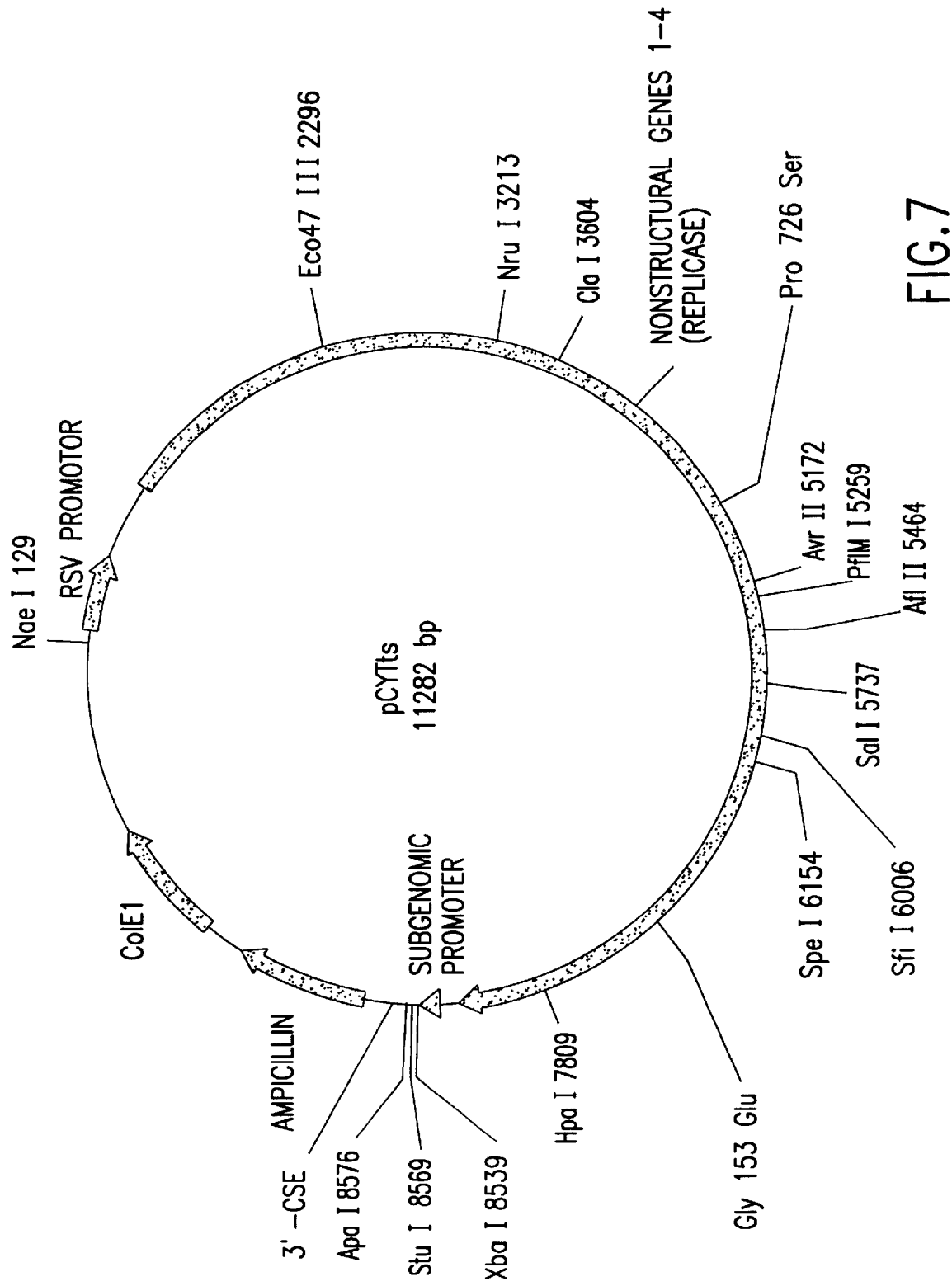

FIG. 7 is a schematic representation of the pCYTts vector. The pCYTts vector contains, in addition to elements shown in FIG. 3, an ampicillin resistance marker for selection in bacterial cells and a ColE1 element which directs high copy number bacterial amplification. The pCYTts vector was prepared as described in PCT publication WO 99/50432, the entire disclosure of which is incorporated herein by reference.

FIGS. 8A–8D show the complete cDNA sequence of pCYTts (SEQ ID NO:1).

Figure 9A:
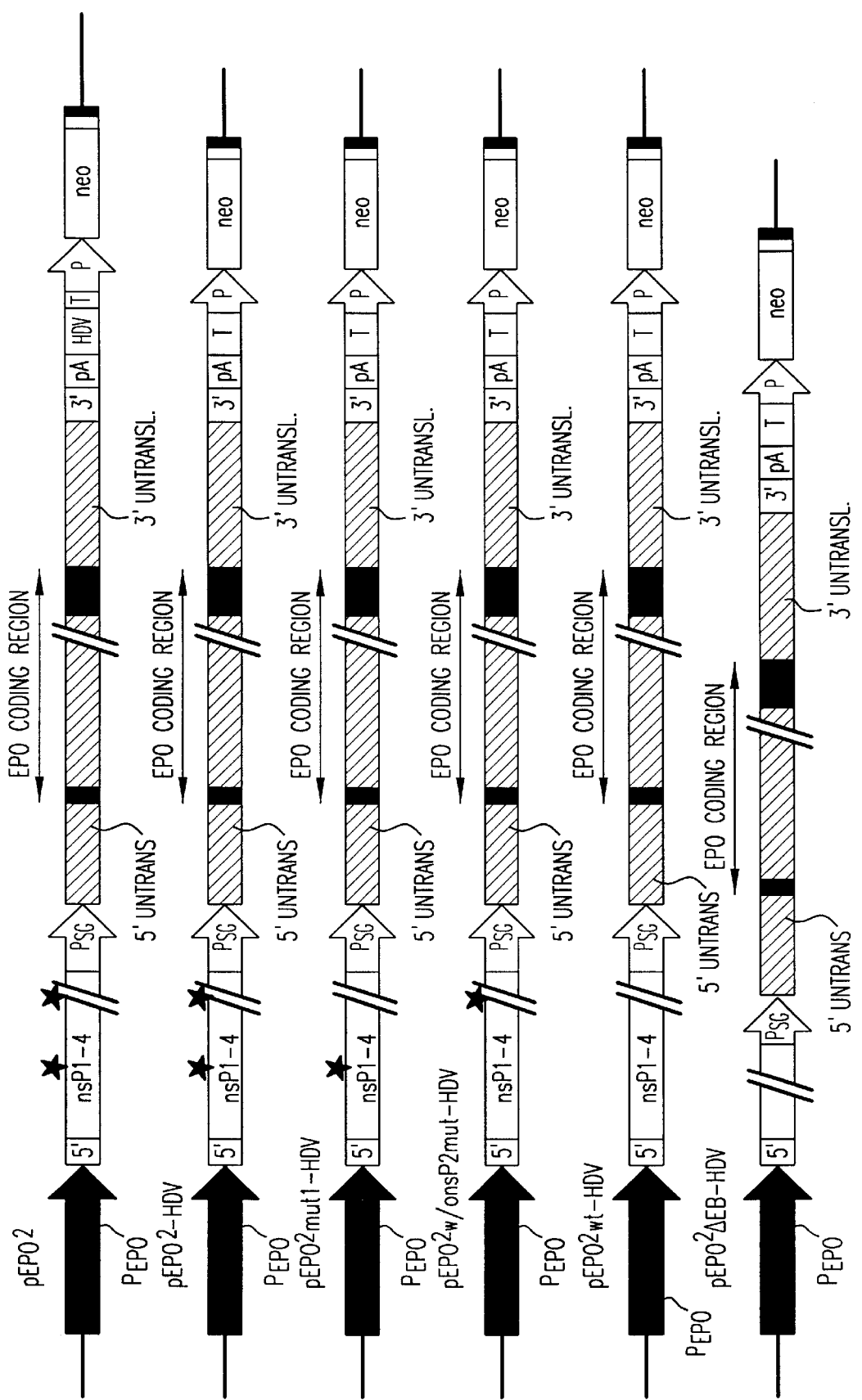
Figure 9B:
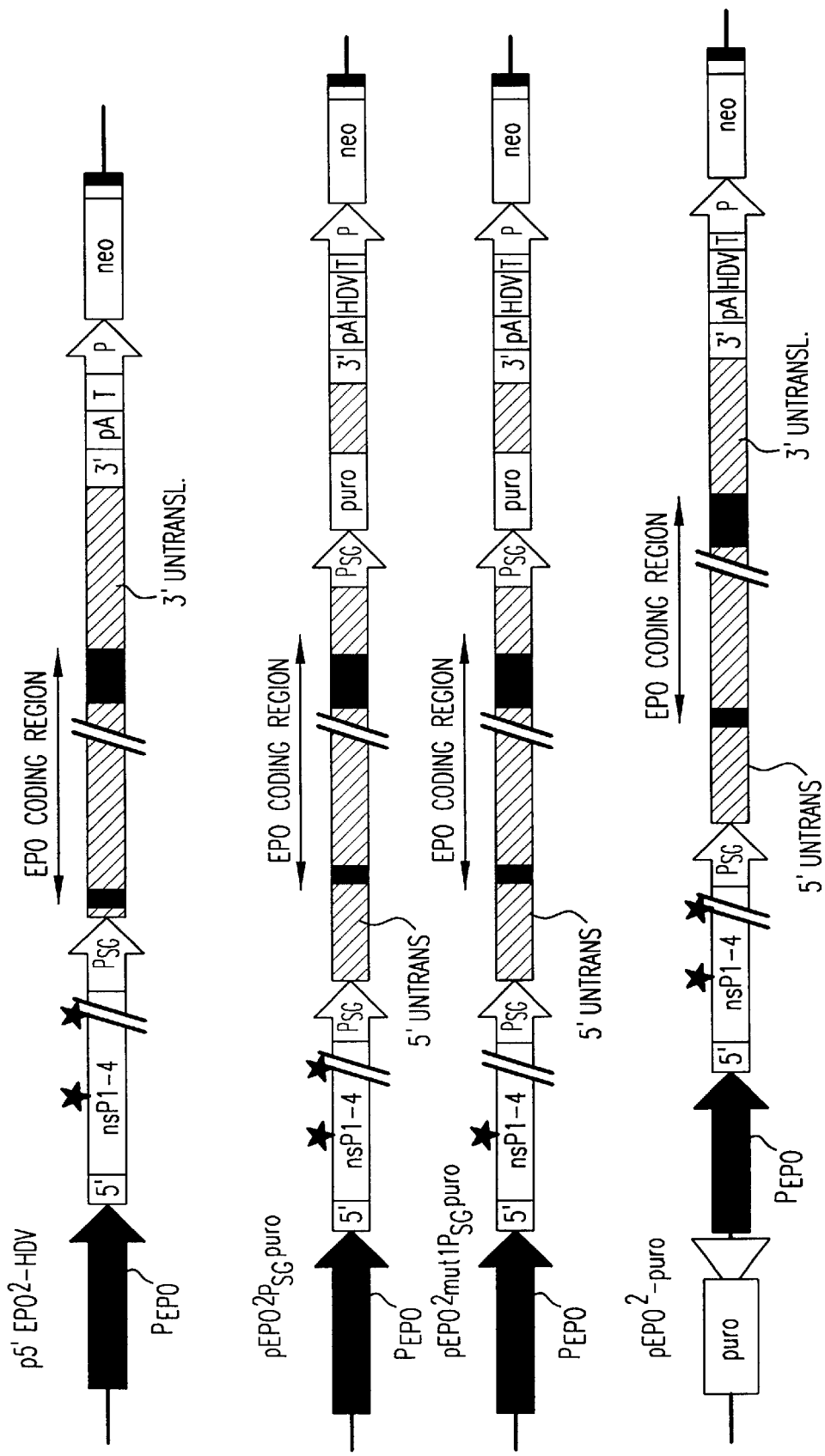
Figure 9C:
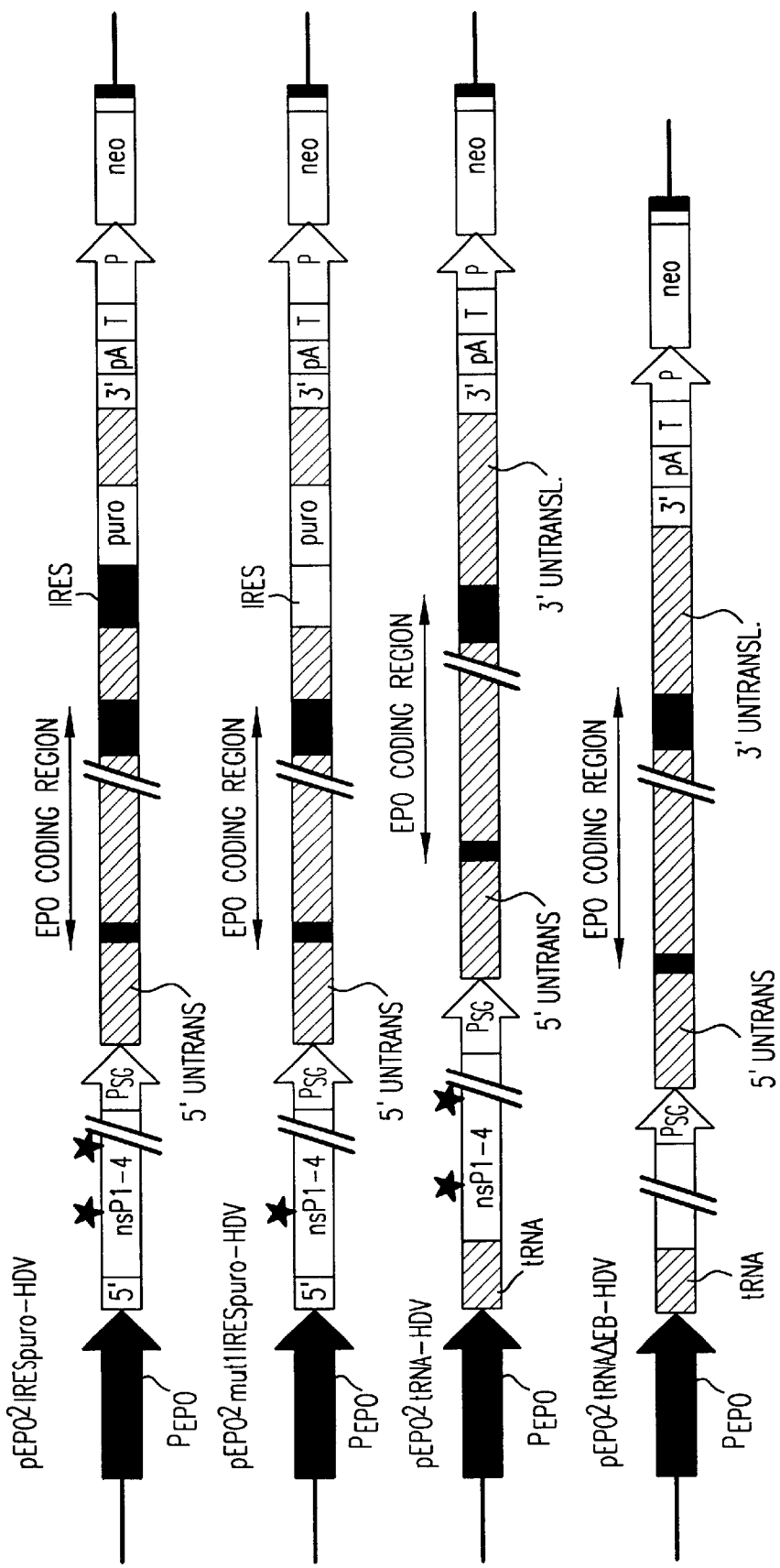

FIGS. 9A–9C show homologous recombination 'mimic' constructs, which can be used to identify the arrangement of genetic elements leading to maximum EPO expression. The constructs shown comprise all necessary genetic elements including the chromosomal EPO sequence. Once a particular genetic arrangement has been identified as optimal expression system, a production cell line is constructed by homologous recombination (i.e., without introducing EPO coding region into the cell) that contains the same arrangement of genetic elements within its chromosome. Abbreviations in FIGS. 9A–9C are as follows: EPO promoter ($P_{EPO}$), 5' cis-acting replication elements (5'), 3' cis-acting replication elements (3'), nucleic acid encoding non-structural proteins 1–4 (nsP 1–4), nsP2 and ts6 mutations within these genes are indicated by asterisks, subgenomic promoter ($P_{SG}$), 5' untranslated region of the EPO gene (5' untrans), 3' untranslated region of the EPO gene (3' untransl.), nucleic acid encoding and corresponding to a 37 nucleotide stretch of adenine residues (pA), nucleic acid encoding the Hepatitis delta virus antigenomic ribozyme (HDV), transcriptional terminator and polyadenylation signal (T), RNA polymerase II promoter (P), nucleic acid encoding neomycin resistance (neo), nucleic acid encoding puromycin resistance (puro), internal ribosome entry site (IRES), and nucleic acid encoding and corresponding to aspartate transfer RNA (tRNA).

Figure 10:
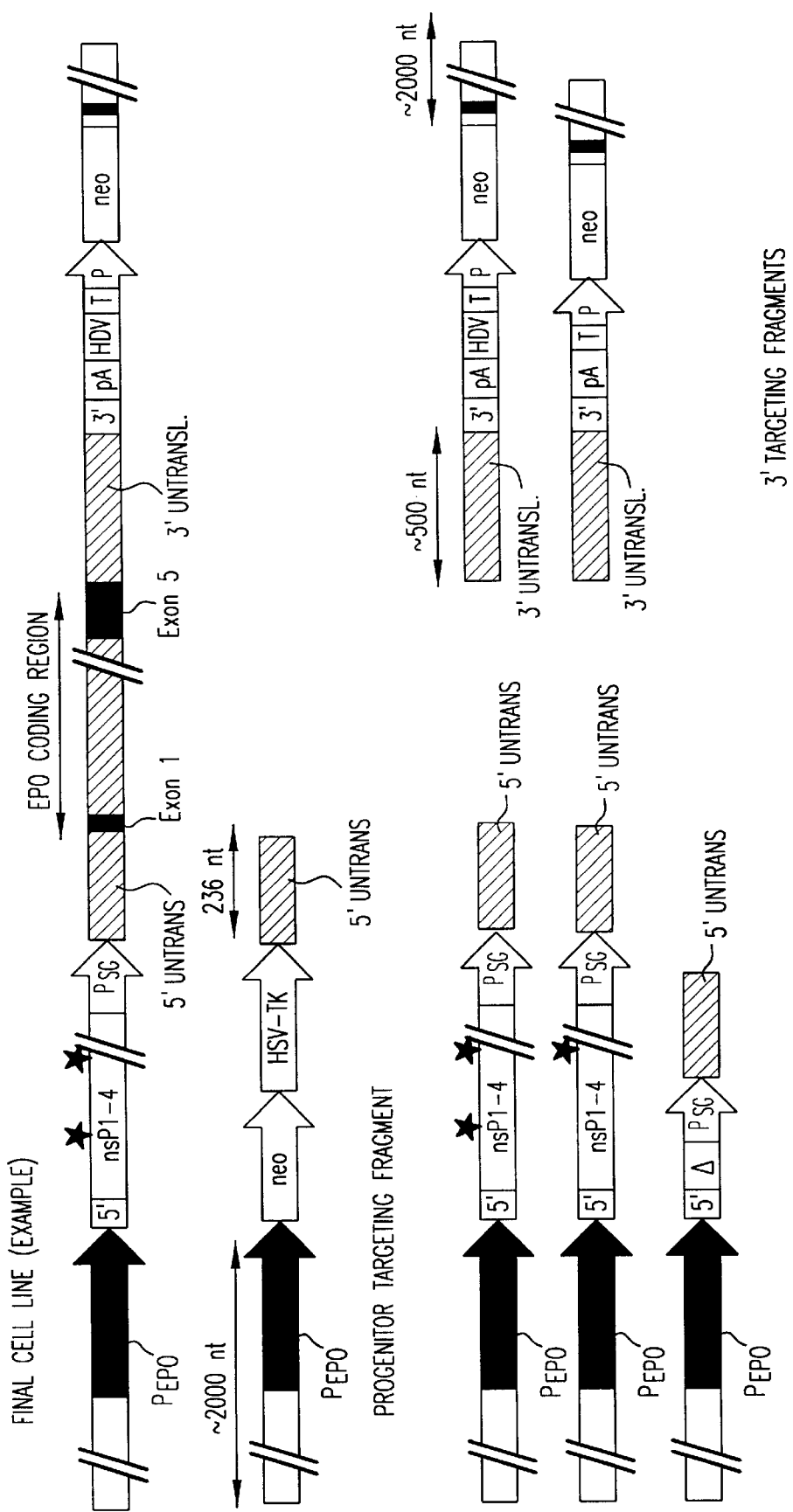

FIG. 10 shows homologous recombination targeting fragments. Only examples for possible homologous recombination targeting fragments are shown, a number of variations with respect to inclusion/omission and exact arrangement of genetic elements are possible based on the invention (see e.g., "homologous recombination 'mimic' constructs", FIGS. 9A–9C). Abbreviations in FIG. 10 are as follows: EPO promoter ($P_{EPO}$), 5' cis-acting replication elements (5'), 3' cis-acting replication elements (3'), nucleic acid encoding non-structural proteins 1–4 (nsP1–4), nsP2 and ts6 mutations within these genes are indicated by asterisks, subgenomic promoter ($P_{SG}$), 5' untranslated region of the EPO gene (5' untrans), 3' untranslated region of the EPO gene (3' untransl.), nucleic acid encoding and corresponding to a 37 nucleotide stretch of adenine residues (pA), nucleic acid encoding the Hepatitis delta virus antigenomic ribozyme (HDV), transcriptional terminator and polyadenylation signal (T), RNA polymerase II promoter (P), nucleic acid encoding neomycin resistance (neo), nucleic acid encoding herpes simplex thymidine kinase (HSV-TK), and an internal deletion within the nsP1–4 coding region ($\Delta$). The latter construct has to be used in conjunction with an expression construct providing the non-structural proteins in trans (e.g., pCYTts or other nsP1–4 expression cassette).

DETAILED DESCRIPTION OF THE PREFERRED EMBODIMENTS

The present invention is directed to methods for altering the expression characteristics of endogenous genes in eukaryotic cells. The invention also provides recombinant eukaryotic host cells produced by the methods of the invention, expression products of endogenous genes having altered expression characteristics, and vector systems for practicing methods of the invention.

In brief, the invention is based on the introduction of exogenous nucleic acid into nucleic acid molecules (e.g., in a nuclear chromosome, mitochondrial chromosome, chloroplast chromosome, or an extrachromosomal element) which reside in a eukaryotic cell resulting in the altered expression of an endogenous target gene or, when multiple endogenous target genes are transcribed as part of the same primary RNA transcript, more than one such gene (e.g., two, three, four, five, six, seven, etc. genes). The exogenous nucleic acid will generally contain genetic elements which allow for amplification (i.e., replication) of RNA molecules corresponding to an endogenous target gene.

Activation of transcriptionally silent genes by insertion of genetic elements into endogenous cellular nucleic acids has been previously described (see Treco et al., U.S. Pat. No. 5,641,670 and Chappel, U.S. Pat. No. 5,272,071). However, most previous gene activation methods involve the insertion of transcription control sequences (i.e., promoters) in operable linkage with endogenous genes. These inserted transcriptional control sequences generally have stronger transcriptional activation activity than that of the endogenous control sequences.

In many embodiments of the present invention, while the endogenous target gene promoter may be used in a targeting sequence, the nucleotide sequences and properties of this endogenous promoter is not altered. In other words, in these embodiments, the increased RNA level which results from the practice of the invention does not result from a significant increase in the number of RNA transcripts produced from the endogenous target gene locus. Instead, increased RNA level results from RNA replication.

I. Definitions

The following definitions are provided to clarify the subject matter of the present invention.

As used herein, the term "alphavirus" refers to any of the RNA viruses included within the genus Alphavirus. Descriptions of members of this genus are contained in Pfeffer et al., *Virol.* 240:100–108 (1998) and Strauss and Strauss, *Microbiol. Rev.* 58:491–562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEB), and Ross River virus.

As used herein, the phrase "homologous recombination" refers to the process in which nucleic acid molecules with similar nucleotide sequences associate and exchange nucleotide strands. A nucleotide sequence of an endogenous nucleic acid which is effective for engaging in homologous recombination at a predefined position of an endogenous target nucleic acid will therefore have a nucleotide sequence which facilitates the exchange of nucleotide strands between the exogenous nucleic acid molecule and a defined position of an endogenous nucleic acid. Thus, the exogenous nucleic acid will generally have a nucleotide sequence which is sufficiently complementary to a portion of the endogenous nucleic acid molecule to promote nucleotide base pairing.

As used herein, the phrase "vector construct" refers to a nucleic acid molecule used in methods of the invention to produce recombinant eukaryotic host cells which exhibit altered expression of an endogenous target gene. In most instances, the practice of the present invention will require the use of at least two vector constructs, referred to as a 5' targeting construct and a 3' targeting construct. These two or more vector constructs of the invention are collectively referred to as a "vector system".

As used herein, the phrases "endogenous promoter" and "endogenous nucleic acid" refer to nucleic acid which is either native to or resides in a eukaryotic cell prior to the insertion of vector constructs of the invention into the cell. One example, of an endogenous nucleic acid is a yeast artificial chromosome which is present in a yeast cell prior to introduction of vector constructs of the invention.

As used herein, the phrase "endogenous target gene" refers to an endogenous gene, the expression characteristics of which are altered by methods and vector constructs of the invention.

As used herein, the term "exogenous," when used in reference to a nucleic acid, refers to nucleic acid which is introduced into a eukaryotic cells during the practice of methods of the invention. One example, of an exogenous nucleic acid is a targeting construct. Exogenous nucleic acids can encode proteins or RNA molecules normally expressed in the cell type in which they are present or molecules not normally expressed therein (erg., Sindbis non-structural and structural proteins).

As used herein, the phrase "selection marker" refers to a gene the expression of or the lack of expression of which allows cells that either contain the gene or do not contain the gene to be identified under particular conditions. A selection marker can be one that allows a cell to proliferate on a medium that prevents or slows the growth of cells without the gene. Examples of such markers include antibiotic resistance genes and genes which allow an organism to grow on a specific metabolite. Alternatively, the selection marker can facilitate visual screening of transformants by conferring on cells a phenotype that is easily identified. Such an identifiable phenotype may be, for examples, the production of luminescence, a colored compound, or a detectable change in the medium surrounding the cell. A selection marker can also be a gene which prevents a cell from reproducing or performing metabolic reactions under conditions which result in selection against cells which are reproducing or are metabolically active. Various other selection markers, as well as selection schemes which employ selection markers, would be apparent to one skilled in the art. For convenience, as used herein, the phrase "selection marker" also refers to the expression product of the gene which encodes this marker.

As used herein, the phrase "corresponds to", when used in reference to a nucleic acid, means that the nucleic acid has a nucleotide sequence which is the same as all or a portion of a reference nucleic acid. The phrase "corresponds to", however, is not strand specific. In other words, two nucleic acid strands having antisense nucleotide sequences would "correspond to" each other.

As used herein, the phrase "complementary to", when used in reference to a nucleic acid, means that the nucleic acid has a nucleotide sequence which is identical to the opposite strand to which it is compared. For example, the 5'-3' nucleotide sequence "ATGCC" is complementary to the 3'-5' nucleotide sequence "TACGG". Thus, unlike the phrase "corresponds to", the phrase "complementary to" is stand specific.

As used herein, the term "homologous", when used in reference to two nucleic acids, means that these nucleic acids share some level of similarity at the nucleotide level. As discussed below, two nucleic acids must be homologous, but need not exactly correspond to each other, in order to undergo homologous recombination. As one skilled in the art would recognize, the term "homologous" inherently includes complementary strands of nucleic acid molecules. For the sake of simplicity, generally reference is only made herein to nucleic acid strands of molecules which have identical nucleotide sequences, as compared to antisense/complementary sequences.

As used herein, the phrases "cis-acting replication elements" and "cis-acting sequences" refer to nucleic acids to which a replicase binds to catalyze RNA-dependent replication of RNA molecules. These RNA-dependent replication events can result in the replication of either full-length or partial RNA molecules. Thus, the alphavirus subgenomic promoter, as well as subgenomic promoters of other viruses (e.g., Rubella virus, turnip crinkle virus, etc.) and synthetic nucleic acids which perform essentially the same functions, are considered to be "cis-acting sequences". Cis-acting sequences may be located at or near the 5' end of an RNA molecule, at or near the 3' end of an RNA molecule, or at or near both ends of an RNA molecule, as well as internally. A number of cis-acting sequences are set out in Pfeffer et al., *Virology* 240:100–108 (1998).

Cis-acting sequences suitable for use in the practice of the invention could be derived from any number of RNA viruses, particularly RNA viruses of the family Togaviridae.

As used herein, the phrase "RNA-Dependent RNA polymerase" refers to a polymerase that catalyzes the polymerization (synthesis) of an RNA molecule using another RNA molecule as a template. This phrase is used herein synonymously with the term "replicase." One example of a replicase is the replication complex formed by the gene products of the Sindbis nsP 1–4 genes.

As used herein, the term "transcription" refers to the production of RNA molecules from DNA templates catalyzed by RNA polymerases.

As used herein, the phrase "RNA replication" refers to processes which result in the formation of an RNA molecule using another RNA molecule as a template.

As used herein, the phrase "untranslated RNA" refers to an RNA molecule which does not contain an open reading frame or contains an open reading frame, or portion thereof, but in a format in which an amino acid sequence will not be produced (e.g., no initiation codon is present). Examples of such molecules are tRNA molecules, rRNA molecules, and ribozymes. Antisense RNA may also be untranslated RNA but, in some instances, antisense RNA can be converted to a translatable sense strand from which a polypeptide is produced. (See, e.g., PCT publication WO 99/50432.)

As used herein, the phrase "temperature-sensitive" refers to an enzyme which readily catalyzes a reaction at one temperature but catalyzes the same reaction slowly or not at all at another temperature. An example of a temperature-sensitive enzyme is the replicase protein encoded by the pCYTts vector, which has readily detectable replicase activity at temperatures below 34° C. and has low or undetectable activity at 37° C. (See PCT publication WO 99/50432.)

As used herein, the phrase "permissive temperature" refers to a temperature at which an enzyme has relatively high levels of catalytic activity.

As used herein. the phrase "restrictive temperature" refers to a temperature at which an enzyme has undetectable or relatively low levels of catalytic activity. Both "hot" and "cold" sensitive mutants are known and, thus, a restrictive temperature may be higher or lower than a permissive temperature.

As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

The phrase "low or undetectable," when used in reference to the catalytic activity of an enzyme, refers to a level of expression which is either significantly lower (e.g., at least five fold, ten fold, fifteen fold, or twenty fold lower) than that seen when the enzyme is placed under conditions where it is maximally activated or is not readily detectable by the methods used in the following examples section. With respect to enzymes such as replicases, for example, the level of catalytic activity can be measured by the production of expression products (e.g., polypeptides) produced by the replicase.

As used herein, the phrase "recombinant eukaryotic host cell" refers to a eukaryotic cell into which one or more nucleic acid molecules of the invention have been introduced. Such cells include slime molds, algae, yeasts (e.g., *Saccharomyces cerevisiae, Schizosaccharomyces pombe*), protists (e.g., *Paramecium tetraurelia, Paramecium caudatum, Chaos carolinensis, Tetrahymena thermophila*), as well as cells derived from plants (e.g., *Zea mays, Triticum aestivum, Glycine max*) and animals (e.g., humans, dogs, cats, horses, cattle, rats, hamsters, mice, mosquitos). Generally, these cells will be homologous recombination competent cells.

II. Vector Systems of the Invention

A. General Features

In many cell lines, gene expression initiated at endogenous promoters is too low for these cells to be useful for the preparative production of endogenous gene products. However, after insertion of all the elements needed for viral RNA replication by homologous recombination into the endogenous target gene locus, amplification of the RNA transcripts initiated at the endogenous gene promoter can be achieved in these cells. In other words, a replicon-like expression cassette under control of the cellular gene promoter can be produced by recombining the necessary viral elements into the genomic endogenous target gene locus (see, e.g. FIGS. 1, 2, and 5A–5B). Using this approach, it is possible to alter the expression of endogenous target genes without either introducing heterologous transcription control elements or altering the endogenous target gene coding sequences.

Further, in the practice of the invention, at least two nucleic acid constructs, referred to herein as 5' and 3' targeting constructs, are normally generated which can integrate into the nucleic acid flanking the endogenous target gene coding region. The invention thus provides vector systems and methods for modifying the expression characteristics of endogenous target genes.

The methods of the invention, which are discussed below, will generally be practiced using vector constructs designed to produce recombinant eukaryotic host cells having an endogenous target gene with altered expression characteristics. These host cells will typically exhibit increased gene expression. However, these cells may be designed to exhibit decreased endogenous target gene expression, for example, when an endogenous target gene is expressed in an antisense format.

In most instances, the practice of the methods of the invention requires the insertion of two nucleic acid molecules at or near the genetic locus which contains the endogenous target gene. These nucleic acids will normally be inserted 5' and 3' to the endogenous target gene and are referred to herein as 5' and 3' vector constructs.

While many variations of the invention are possible, one or both of the 5' and 3' vector constructs, referred to herein collectively as "targeting constructs", will normally contain the following elements: (1) one or more (e.g., one, two, three, four, five, etc.) regions of homology to a genetic locus located at or near an endogenous target gene (referred to herein as either "targeting sequences" or "targeting elements"); (2) one or more (e.g., one, two, three, four, five, etc.) genetic elements for determining whether the vector construct has integrated into the eukaryotic cell genome at the appropriate location or for identifying cells which contain the vector construct integrated at the appropriate location (referred to as "selection markers"); (3) one or more (e.g., one, two, three, four, five, etc.) cis-acting replication elements which allow for the amplification of RNA; and, in some instances, (4) additional nucleic acid coding sequences which are to be inserted into the endogenous target nucleic acid (e.g., replicase coding sequences).

Replicase protein coding sequences and cis-acting sequences used in the vector constructs of the invention will often be derived from a virus (e.g., a Rubella virus), often from an Alphavirus, and generally from Sindbis virus. Thus, in many embodiments, the vector constructs of the invention will contain Alphaviral genetic elements.

Alphaviruses are positive stranded RNA viruses which replicate their genomic RNA entirely in the cytoplasm of the infected cell and without a DNA intermediate (Strauss, J.

and Strauss, E., *Microbiol. Rev.* 58:491–562 (1994)). The concept that alphaviruses can be developed as expression vectors was first established a number of years ago (Xiong, C. et al., *Science* 243:1188–1191 (1989)). Since then, several improvements have made the use of these RNA replicons as expression vectors more practical (Lundstrom, K., *Curr. Opin. Biotechnol.* 8:578–582 (1997)).

DNA vectors have been developed for both Sindbis virus (Herweijer, H. et al., *Hum. Gene Ther.* 6:1495–1501 (1995); Dubensky, T. W. et al., *J. Virol.* 70:508–519 (1996)) and SFV (Berglund, P. et al., *Trends Biotechnol.* 14: 130–134 (1996)). Eukaryotic promoters are introduced in these vectors upstream from the alphavirus replicase gene (consisting of the four non-structural protein genes (nsP1–4)) which are translated as one or two polyproteins that are then proteolytically cleaved (Strauss, J. and Strauss, E., *Microbiol. Rev.* 58:491–562 (1994)). DNA is transcribed to RNA from the recombinant eukaryotic promoter in the nucleus and transported to the cytoplasm, where the replicase catalyzes the replication of the alphavirus RNA molecule as during normal replication of the alphavirus RNA molecule (Strauss, J. and Strauss, E., *Microbiol. Rev.* 58:491–562 (1994)). However, only transient expression of heterologous sequences has been possible until recently due to the cytopathogenicity of the alphavirus replicase (Lundstrom, K., *Curr. Opin. Biotechnol.* 8:578–582 (1997)). As suggested above and discussed below, non-cytopathic Alphavirus vectors useful for molecular cloning have been developed.

DNA vectors have also been developed for positive stranded RNA viruses other than Alphaviruses. Turina et al., *Virol.* 241:141–155 (1998), for example, describe an infectious cDNA clone of panicum mosaic virus (PMV), a member of the Tombusviridae family. Thus, replicase protein coding sequences, cis-acting sequences, and other elements used in the vector constructs of the invention can also be derived from viruses other than Alphaviruses.

A number of non-Alphavirus viruses and vectors which contain components suitable for use in the present invention have been identified or constructed (see, e.g., Caley et al., *J. Virol.* 71:3031–3038 (1997); Davis et al., *J. Virol.* 70:3781–3787(1996); Kohno et al., *Gene. Ther.* 5:415–418 (1998); Pushko et al., *Virology* 239:389–401 (1997); Roks et al., *Cardiovasc. Res.* 35:498–504 (1997). Turina et al., *Virol.* 241:141–155 (1998); Zhang et al., *Gene. Ther.* 4:367–374 (1997); Strauss and Strauss, *Microbiol. Rev.* 58:491–562 (1994)). These viruses include plus-stranded viruses classified in the following groups:

1. Enterovirus (e.g., polioviruses (e.g., polioviruses 1, 2 and 3), coxsackieviruses virus, swine vesicular disease virus);
2. Rhinovirus (e.g., human rhinovirus 1A);
3. Flavivirus (e.g., yellow fever virus; dengue virus serotypes 1, 2, 3, and 4; Japanese encephalitis virus, West Nile virus, Kunjin virus, Murray Valley encephalitis virus, St. Louis encephalitis virus, tick-borne encephalitis viruses);
4. Pestivirus (e.g., bovine diarrhea virus, border disease virus, hog cholera virus);
5. "Hepatitis C-like" viruses; and
6. Alphanodavirus (e.g., Nodamura, flock house, black beetle, Boolarra, Manawatu, gypsy moth, striped jack nervous necrosis viruses).

Thus, targeting constructs of the invention, for example, may be prepared using appropriate genetic elements derived from viruses classified in any of the above groups, as well as other viruses which contain genetic elements that perform the functions required by targeting constructs of the invention.

B. Targeting Sequences/Elements

In order for one nucleic acid molecule to integrate into another nucleic acid molecule by homologous recombination, the two molecules must share at least one region of homology.

Homologous recombination is a process in which nucleic acid molecules having similar nucleotide sequences line up side-by-side and exchange nucleotide strands. A nucleotide sequence of a recombinant nucleic acid which is effective for engaging in homologous recombination at a predefined position of an endogenous nucleic acid must have a nucleotide sequence which facilitates the exchange of strands between the recombinant nucleic acid molecule and the endogenous nucleic acid.

A vector construct suitable for homologous recombination will generally have at least one region with a nucleotide sequence that is complementary to an endogenous nucleic acid molecule, thereby promoting base pairing between nucleotides of the two nucleic acids. Any recombinant nucleic acids can be employed as long as they facilitate homologous recombination at specific and selected positions of endogenous nucleic acid molecules.

Unless designed to integrate by random integration (see, e.g. FIGS. 5A–5B), the vector constructs of the invention will generally have at least one region, referred to as a targeting sequence, with substantial sequence homology to a portion of an endogenous nucleic acid molecule into which the vector construct is inserted. This endogenous nucleic acid molecule will normally be a nuclear chromosome, mitochondrial chromosome, chloroplast chromosome, or an extrachromosomal element (e.g., a double minute).

In general, the efficiency of homologous recombination between a targeting construct and an endogenous genetic locus varies with two factors: (1) the amount of homology between the targeting sequences and the endogenous locus where homologous recombination is to occur and (2) the length of the region(s) of the targeting construct which share homology with the corresponding endogenous locus.

In general, the greater the amount of homology between two nucleic acids and the longer the region(s) which share homology, the higher the frequency of homologous recombination. Thus, the efficiency of homologous recombination is increased when the target sequences share a high level of homology with the endogenous nucleic acid. As a result, while homologous recombination can occur between two nucleic acid molecules sharing relatively low homology (e.g., 70–75% identity), recombinant nucleic acid to be inserted into endogenous nucleic acid will generally be flanked by targeting sequences having high homology to the endogenous nucleic acid. In general, these flanking targeting sequences will share at least 90%, 91%, 92%, 93%, 94%, 95%, 96%, 97%, 98% or 99% identity with endogenous nucleic acid. Further, in most instances, the targeting sequences will have nucleotide sequences which are 100% identical to nucleic acid at the recombination locus.

The length of homologous nucleic acid selected for use as targeting sequences in targeting constructs will generally be chosen on the basis of the sequence composition and complexity of the endogenous locus and guidance provided in the art. For example, it is known that targeting sequences 1.3 to 6.8 kilobase segments in length work well for performing homologous recombination but the use of targeting sequences of greater than about 6.8 kilobases in length generally adds less to the targeting frequency (Hasty et al., *Molec. Cell Biol.* 11:5586–5591 (1991); Shulman et al., *Molec. Cell. Biol.* 10:4466–4472 (1990), both of which are incorporated herein by reference in their entireties). Thus, the actual size of the targeting sequences used will be determined by a number of factors, including the information known about the endogenous locus, the number of loci in the genome having nucleotide sequences with homology to the site selected for integration, and the properties of the particular integration site.

In order to select appropriate targeting sequences, it will generally be necessary to either know the sequence of the endogenous nucleic acid at the recombination locus or to have information about this locus such as a restriction map.

While it has been reported that nucleic acid having as little as 14 bases complementary to an endogenous nucleic acid in a genome can engage in homologous recombination, the targeting sequences will typically be at least about 30 bases, at least about 40 bases, at least about 50 bases, at least about 60 bases, at least about 70 bases, at least about 80 bases, at least about 90 bases, at least about 100 bases, at least about 120 bases, at least about 140 bases, at least about 160 bases, at least about 180 bases, at least about 200 bases, at least about 250 bases, at least about 300 bases, at least about 350 bases, at least about 400 bases, or at least about 450 bases in length. In general, however, the targeting sequences will be at least about 500 bases, at least about 600 bases, at least about 700 bases, at least about 800 bases, at least about 900 bases, or at least about 1000 bases in length.

Due to the relatively long length of the homologous regions that will normally be used as targeting sequences, it will generally be advantageous to obtain the targeting sequences of vector constructs from either cells of the same cell line which is to undergo homologous recombination (e.g., Hep G2, Hep 3B, 293) or cells of the same organism (e.g., human, Chinese hamster, *Rattus norvegicus, Zea mays*). In other words, it is generally advantageous to use targeting sequences derived from cells as closely related as possible to the cell line in which homologous recombination is to occur.

Factors for consideration in the selection of nucleic acids and methods for using these nucleic acids for homologous recombination are described, e.g., in Skoultchi, U.S. Pat. No. 5,981,214; Berns et al., U.S. Pat. No. 5,789,215; Muller, Mech. Dev. 82:3–21 (1999); Lai et al., *Exp. Nephrol.* 7:11–14 (1999); and Deng et al., *Mol. Cell. Bio.* 12:3365–3371 (1992), the entire disclosure of each of which is incorporated herein by reference.

As explained in more detail below, the targeting sequences will generally contain between them a nucleic acid which is to be inserted into endogenous nucleic acid and at least one selection marker. Further, as also explained below, another selection marker (e.g., a negative selection marker) may be located either 5' to the 5' targeting sequence or 3' to the 3' targeting sequence. In most instances, such a marker will integrate into an endogenous nucleic acid only when non-homologous recombination occurs.

C. Selection Markers

Any number of selection markers can be used in the practice of the present invention. In general, however, two types of marker which can be employed: positive selection markers and negative selection markers.

Positive selection markers are markers that, in effect, allow for the identification of cells which express the gene product of the marker gene. Thus, it is possible to identify a recombinant cell which expresses a gene encoding a positive selection marker. Identification can occur by any number of means but will generally be scored by survival or growth of the cell under selective pressure. Positive selection markers include those which confer antibiotic and ouabain resistance. Specific examples of genes which can be used as positive selection markers include genes which encode neomycin phosphotransferase (neo), metallothionein I, metallothionein II, dihydrofolate reductase (DHFR), hygromycin B phosphotransferase (hph), puromycin-N-acetyl-transferase, xanthine/guanine phosphoribosyl transferase, tryptophan synthase (β-subunit, trpB), and histidinol dehydrogenase (hisD) (see, e.g., Hartman & Mulligan, *Proc. Natl. Acad. Sci. USA* 85:8047–8051 (1988)).

Negative selection markers are markers that, in effect, allow for the identification of cells which do not express the gene product of the marker gene. Cells which express a negative selection marker will generally be distinguished from those which do not by negative selection of those which express the selection marker. Negative selection markers include genes which encode products that convert less toxic compounds to more toxic compounds. Specific examples of enzymes which can be used as negative selection markers include *Herpes simplex* thymidine kinase, hypoxanthine phosphotransferase (HPRT), diphtheria toxin, ricin toxin, Diptheria toxin, xanthine/guanine phosphoribosyl transferase, adenosine deaminase, and cytosine deaminase.

Some markers, such as genes which encode detectable tags (e.g., luciferase, alkaline phosphatase, horseradish peroxidase), can function as both positive and negative selection markers. For example, cells which express the green fluorescent protein of *Aequorea victoria*, as well as variants of this protein (e.g. yellow green fluorescent protein, cyan fluorescent protein), can be identified and sorted using a cell sorter. Methods of this nature are described, for example, in Levy et al., *Nat. Biotechnol.* 14:610–614 (1996) and Bierhuizen et al., *Biochem. Biophys. Res. Commun.* 234:371–375 (1997).

A considerable number of nucleic acids encoding additional selection markers are known in the art (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)).

While it will almost always be advantageous to include a selection marker for identifying cells which have integrated the vector construct into an endogenous nucleic acid molecule, the actual use of these markers will vary with the particular application. For example, when it is advantageous to identify cells in which a targeting construct has integrated via homologous recombination a positive-negative selection scheme can be used to reduce the background of cells wherein the targeted construct has integrated via non-homologous recombination.

Positive-negative selection systems typically employ two active selection markers. In one embodiment, a positive selection marker is used which is expressed following either non-homologous or homologous integration in an endogenous nucleic acid and a negative selection marker is used which is only expressed following non-homologous integration. By combining both positive and negative selection, recombinant eukaryotic host cells having the correctly targeted homologous recombination event can be efficiently obtained. Positive-negative selection schemes are described, for example, in Capecchi et al., U.S. Pat. No. 5,631,153 and WO 94/06908.

A targeting construct for positive-negative selection will generally contain a gene encoding a positive selection marker located between the targeting sequences and a gene encoding a negative selection marker located either 5' to the 5' targeting sequence or 3' to the 3' targeting sequence. Thus, when the targeting construct integrates into an endogenous nucleic acid by non-homologous recombination, the positive and negative selection markers will normally both be expressed. Further, when the targeting construct integrates into an endogenous nucleic acid by homologous recombination, the positive selection markers will normally be expressed but the negative selection marker will not be expressed. This is so because the gene encoding the negative selection marker is not located between the 5' and 3' targeting sequences and, thus, will normally not integrate into the endogenous target locus.

Depending on the particular approach, a number of methods can be used for selection marker expression. For examples, markers can be (i) operably linked to an RNA polymerase II promoter, (ii) operably linked to a viral subgenomic promoter, (iii) operably linked to an internal ribosome entry site (IRES), or (iv) fused to either a complete or a partial viral gene (e.g., fused to codon 121 of nsP1; see Polo et al., *Proc. Natl. Acad. Sci USA* 96:4598–4603 (1999)).

D. Cis-Acting Replication Elements

The targeting constructs of the invention will generally contain nucleic acid which allows for the amplification of RNA molecules in which they reside, referred to herein as "cis-acting replication elements" or "cis-acting sequences". Replicase proteins bind to these cis-acting replication elements and catalyze RNA-dependent replication of RNA molecules. RNA-dependent replication can result in the replication of the full-length and partial RNA molecules and, thus, alphavirus subgenomic promoters are considered to be cis-acting sequences.

When a cis-acting replication element is located at or near the end of an RNA molecule, replication of this molecule generally results in a product which corresponds to the entire RNA template. However, when a cis-acting replication element is located internally in an RNA molecule, replication generally results in a product which corresponds to only part of the RNA template.

In most instances, the targeting vectors used in the methods of the invention will be designed so as to place cis-acting replication element in positions such that RNA replication proceeds according to several steps. First, an RNA molecule is produced from a DNA template which corresponds to a considerable amount of the targeting constructs and either the entire endogenous target gene or a selected portion thereof. This RNA molecule is referred to herein as a "replicon". Second, essentially the entire replicon is replicated. Third, a subportion of the replicon is replicated again to produce RNA which corresponds to the endogenous target gene. Each of the above replication events is catalyzed by a replicase protein which binds to cis-acting replication elements. This process is represented schematically in, for example, FIGS. 3 and 4.

Additional elements may be included in nucleic acid molecules of the invention which confer particular properties upon these molecules. For example, in defective interfering (DI) particles, it has been found that the 5' ends of the respective RNAs are frequently modified. Modifications found comprise replacement of the regular 5' end of virion RNA by nucleic acid which encodes tRNAs or parts thereof or by nucleic acid derived from the 5' end of the 26S subgenomic RNA. These modifications support RNA replication more efficiently than the normal 5' end of RNA does (Monroe & Schlesinger, *Proc. Natl. Acad. Sci. USA* 80:3279–3283 (1983); Tsiang et al., *J. Virol.* 54:38–44 (1985); Tsiang et al., *J. Virol.* 62:47–53 (1988); Straus & Strauss, *Microbiol. Rev.* 58:491–562 (1994)). Therefore, it may be advantageous to include such modifications in the DNA fragments of the invention.

Examples of locations where cis-acting replication elements can be placed in accordance with methods of the invention are set out in the accompanying figures and below in the specific embodiments.

E. Additional Coding Sequences

In many instances, at least one of the targeting constructs will contain nucleic acid which encodes polypeptides required for RNA dependent replication of RNA molecules. Further, these coding sequences will generally be inserted into endogenous nucleic acid. While any polypeptides which allow for RNA replication can be used, examples of such polypeptides are the Alphaviral nsP1–4 (non-structural proteins 1–4) gene products. FIGS. 3 and 4 shows schematic representations of recombinant cells which amplify RNA encoding endogenous target genes after insertion of targeting vectors of the invention.

As suggested above, the nsP1–4 genes encode a series of polypeptides which are capable of replicating RNA from RNA templates. These nsP genes will generally be located in the targeting construct so as to be operably linked to either an endogenous or an exogenous promoter after integration by homologous recombination. Thus, expression of the RNA containing the endogenous nucleic acid results in the production of a replicon which can be amplified by RNA replication. This replication is catalyzed by a either a constitutive or regulatable RNA-dependent RNA polymerase, which is encoded alternatively on the same or on a different RNA molecule.

When using an alphavirus replicase, in most instances, it is desirable to use a replicase which has been converted to a non-cytopathic phenotype. Preferred mutations which confer such a phenotype are in the nsP2 gene (e.g., the proline residue at position 726 is replaced with a serine residue). Mutations are known in the art which render the replicase protein non-cytopathic (Weiss et al., *J. Virol.* 33:463–474 (1980); Dryga et al., *Virology* 228:74–83 (1997)). These mutations may be introduced by a number of means, including site directed mutagenesis. In other instances, it may be desirable to use a wild-type replicase, for example, in cell lines where the wild-type replicase is not cytopathic (e.g., SF9 cell lines).

As noted above, when a non-cytopathic Sindbis virus replicase is used in the practice of the invention, a mutation may be introduced in the nsP2 gene. One such mutation results from the exchange of the proline residue at position 726 to another of the 20 natural occurring amino acids, such as a serine (abbreviated as "Pro 726 Ser"). Alternatively, any other mutation rendering the replicase molecule non-cytopathic may be used in the practice of the invention. The generation and identification of mutations which render the Sindbis replicase non-cytopathic are described in more detail elsewhere (Weiss et al., *J. Virol.* 33:463–474 (1980); Dryga et al., *Virology* 228:74–83 (1997); WO 97/38087). Further, methods for inducing such mutations are known in the art (see, e.g., Sambrook, J. et al., eds., MOLECULAR CLONING,A LABORATORY MANUAL, 2nd edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Further, Frolov et al., *Proc. Natl. Acad. Sci. USA* 93:11371–11377 (1996) describe a method for identifying non-cytopathic replicases. According to this method, replicons which express the dominant, selective marker, puromycin acetyl-transferase but lack nucleotide sequences which encode structural protein are transfected in BHK cells. Puromycin resistant clones are then selected. Thus, one skilled in the art could generate non-cytopathic replicases suitable for use with the present invention.

A number of mutations in various replicases have been shown to render these proteins non-cytopathic. For example, Frolov et al., *Proc. Natl. Acad. Sci. USA* 93:11371–11377 (1996), describe two Sindbis based replicons which exhibit a non-cytopathic phenotype. The mutation in each of these replicons maps to the nsP2 gene. Perri et al., *J. Virol.* 74:9802–9805 (2000) describe both Sindbis and Semliki Forest virus variants with non-cytopathic phenotypes. The mutations were mapped to several regions within the nsP2 gene. In addition, Khromykh et al., *J. Virol.* 71:1497–1505 (1997), describe Flavivirus Kunjin subgenomic replicons which express a non-cytopathic replicase. Additional examples of mutations in various replicases which render them non-cytopathic are known in the art.

It will generally also be advantageous to be able to regulate replicon replication. One convenient way to regulate replication is to use a temperature-sensitive replicase. Temperature sensitivity (ts) may be conferred, for example, by the introduction of a mutation in the nsP4 gene of the replicase. Preferably, mutations which confer a temperature-sensitive phenotype upon replicase activities are in a protein in complementation group F (Lemm et al., *J. Virol.* 64:3001–3011 (1990)). For example, a temperature-sensitive phenotype may be conferred by changing Gly 153 of nsP4 to Glu. Additionally, any other mutation which renders replicase activity temperature-sensitive can be used in the practice of the invention. Methods for creating and identifying new temperature-sensitive mutants are described by Pfefferkorn (Burge and Pfefferkorn, *Virol.* 30:204–213 (1966); Burge and Pfefferkorn, *Virol.* 30:214–223 (1966)).

While most temperature-sensitive mutants are "hot" sensitive, "cold" sensitive ones are also known (see, e.g., Schwer, B. et al., *Nucleic Acids Res.* 26:803–809 (1998), Mathe, E. et al., *J. Cell Sci.* 111:887–896 (1998), Doedens, J. et al., *J. Virol.* 71:9054–9064 (1997), Patterson, B. et al., *J. Biol. Chem.* 272:27612–27617 (1997)). Thus, the temperature-sensitive replicase may be "cold" or "hot" sensitive and thus will catalyze RNA replication only at temperatures either above or below restrictive temperatures. In one embodiment, RNA replication is catalyzed by the is replicase encoded by the pCYTts vector and occurs at detectable levels only at temperatures lower than 34° C. In a related embodiment, a vector system containing elements of the pCYTts vector, or variant thereof, is used to produce recombinant eukaryotic host cells of the invention and which exhibit altered expression of an endogenous target gene when the temperature of cells containing the vector system is reduced from of about 37° C. to a temperature lower than of about 34° C.

As shown in PCT publication WO 99/50432, permissive temperatures for the replicase encoded by the pCYTts vector are below about 34° C. Further, expression of a gene operably linked to the pCYTts subgenomic promoter increases when the temperature is increased from about 24° C. until a maximal expression level is reached at about 29° C. Additionally, expression of the gene increases as the temperature decreases from about 34° C. Thus, permissive temperatures for the replicase activity encoded by the pCYTts vector are below 34° C., and include temperatures below 24° C., as well as 24° C., 25° C., 26° C., 27° C., 28° C., 29° C., 30° C., 31° C., 32° C., and 33° C. and intervening fractional temperatures up to about 34° C.

The basal level of expression in recombinant eukaryotic host cells containing the pCYTts vector in the inactive state at 37° C. is below the level of detection using standard methods. Further, the temperature-dependent induction profile of gene expression appears to be independent of the chromosomal integration site and copy number. (See PCT publication WO 99/50432.) In some cases, it may be desirable to use a non-temperature-sensitive replicase, for example, when replicase activity at 37° C. is desired.

A number of mutations in various replicase are known in the art to render these proteins temperature sensitive. For example, Burge et al., *Virology* 30:214–223 (1966), describe eleven temperature sensitive Sindbis viruses having mutations which map to five different complementation groups. Further, Suopanki et al., *J. Gen. Virol.* 79:309–319 (1998), describe a temperature-sensitive SFV RNA-dependent RNA polymerase having an alteration in amino acid 781 of nsP2. Suopanki et al., *J. Gen. Virol.* 79:309–319 (1998), also describe a number of temperature sensitive Sindbis mutants. designated ts15, ts17, ts24, and ts133. Further, Strauss et al., *Microbiol. Rev.* 58:491–562 (1994), describe, a series of temperature-sensitive replicase mutants which have alterations in nsP4 and exhibit various activities at restrictive temperatures. For additional examples of mutant, temperature-sensitive viral replicases, see, e.g., Burns et al., *Virol.* 189:568–582 (1992); Diamond & Kirkegaard, *J. Virol.* 68:863–876 (1994); Munoz et al., *Intervirology* 38:256–263 (1995); O'Reilly & Kao, *Virol.* 252, 287–303 (1998).

As discussed below, the targeting constructs may also contain nucleic acid which is inserted into endogenous nucleic acid in such a manner as to result in the expression of fusion products. For example, nucleic acid which encodes a signal peptide may be added to the endogenous target gene coding sequence. Also, exogenous nucleic acid which encodes catalytic RNA (e.g., ribozymes) may be integrated into the cell's endogenous nucleic acid such that RNA transcribed from the endogenous target gene locus nucleic acid results in the production of this catalytic RNA.

F. Additional Elements

One skilled in the art would recognize that transcription of replicon RNA from DNA at the integration locus generally depends on genetic elements such as promoters. The promoter used to drive replicon transcription can be the promoter normally associated with the endogenous target gene or an inserted, exogenous promoter.

When an endogenous promoter drives transcription, this promoter need not be a strong promoter because replicon amplification (i.e., replication) and subgenomic RNA production can be used to produce considerable quantities of translatable mRNA, ribozyme RNA, antisense RNA, or other RNA corresponding to the endogenous target gene.

In other embodiments, replicon transcription is driven by exogenous promoters. The promoter selected will vary with the particular application and may be inducible or constitutive. A constitutive promoter will generally be used in conjunction with a non-cytopathic, temperature-sensitive replicase. When an inducible promoter is used, in certain circumstances, it will generally be feasible to use cytopathic, non-temperature-sensitive replicases. This is so because recombinant eukaryotic host cells can be produced and cultured without significant replicase production and, thus, will only produce the cytopathic replicase upon transcription and translation of replicon RNA.

A considerable number of eukaryotic promoters suitable for use with the present invention are known. Suitable RNA polymerase II promoters suitable for use with the present invention include the Rous Sarcoma Virus (RSV), cytomegalovirus (CMV), simian virus 40 (SV40), myeloproliferative sarcoma virus (MPSV), glucocorticoid, metallothionein, Herpes simplex virus thymidine kinase (HSVTK), human immuno deficiency (HIV), mouse mammary tumor virus (MMTV), human polyomavirus BK (BKV), and Moloney murine leukemia virus (MuLV) promoter. Additional suitable promoters are known in the art (see, e.g., Lee, A. et al., *Mol. Cells.* 7:495–501 (1997); Artuc, M. et al., *Exp, Dermatol.* 4:317–321 (1995)). For example, Hew, C. et al., U.S. Pat. No. 5,545,808 describes the production of transgenic fish which express nucleotide sequences linked to an "anti-freeze" gene promoter. Expression of a sequence of interest in such an animal containing a nucleic acid molecule of the invention can be regulated by changing the water temperature the fish is kept in between restrictive and permissive temperatures.

Nucleic acid may also be included in the targeting constructs which encode enhancer elements. When present, these enhancer elements will generally be located in positions where they stimulate transcription from either endogenous or exogenous promoters. A considerable number of enhancers are known in the art. (See, e.g., Graven et al., *Biochim. Biophys. Acta.* 1447:208–2018 (1999); Miyakawa et al., *Biochim. Biophys. Acta.* 1446:359–364 (1999); lituska et al., *J. Biol. Chem.* 274:24401–24407 (1999).)

Additional genetic elements which may or may not be present in targeting constructs include elements which allow for cloning and amplification. Such genetic elements include bacterial selection markers and origins of replication. The pCYTts vector, for example, contains an ampicillin resistance marker for positive selection in bacterial host cells and an *E. coli* origin of replication. A considerable number of nucleic acids encoding origins of replication are known in the art (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)).

Nucleic acids which may also be present in the targeting constructs of the invention include those which either alter the characteristics of the expression product of the endogenous target gene or facilitate processing of RNA corresponding to the endogenous target gene. Examples of such nucleic acids are coding sequences which result in the expression of the endogenous target gene product as a fusion protein and the Hepatitis delta virus (HDV) antigenomic ribozyme.

The HDV antigenomic ribozyme incises the RNA strand in which it resides immediately 5' to its own sequence, thereby generating a proper poly(A) terminus (Perrotta & Been, *Nature* 350:434–436 (1991)). This has been shown to increase the expression of a reporter enzyme by a factor of 3–4 (Dubensky et al., *J. Virol.* 70:508–519 (1996); Pattnaik et al., *Cell* 69:1011–1020 (1992)). Further, the HDV antigenomic ribozyme can be used to cleave RNA of the invention to generate a replication-component RNA molecule having cis-acting sequence, for example, near the 3' terminus. (See FIG. 2.)

The replicons produced by the recombinant eukaryotic host cells of the invention can also contain packaging signals which direct the packaging of these replicons into viral particles. These replicons can be packaged in the presence of wild-type virus or defective helper virus RNA.

A significant improvement was made with the development of defective helper RNA molecules (Bredenbeek, P. et al., *J. Virol* 67:6439–6446 (1993)). These defective helper RNA molecules contain cis-acting sequences, required for replication of the full-length transcription product, and subgenomic RNA promoter sequences which drive the expression of the structural protein genes. For example, in cells containing both replicons with packaging signals and the defective helper virus RNA, alphaviral non-structural proteins allow for replication and amplification of the defective helper virus RNA sequences which are translated to produce virion structural proteins. Since the helper virus RNA lacks packaging signals, these molecules are not packaged into assembled virions. Thus, virion particles produced in this way contain essentially only replicons expressed from the endogenous target gene locus. These non-infective packaged replicons do not contain sequences encoding virion structural proteins and, thus, undergo only one round of host cell infection and are not pathogenic.

Non-infective packaged replicons can be used to infect a culture of suitable host cells simply by addition of the particles to culture medium containing these cells. The preparation of non-infective alpahviral particles is described in a number of sources, including "Sindbis Expression System", Version C, (*Invitrogen* Catalog No. K750-1).

Recombinant eukaryotic host cells of the invention can be used for the temperature-dependent production of non-infective, packaged replicons. These packaged replicons may be produced using recombinant eukaryotic host cells of the invention which also contain nucleic acid encoding a helper virus RNA sequence. For example, the endogenous target gene locus may encode a replicon which contains packaging signals, nucleic acid encoding a non-cytopathic, temperature-sensitive replicase, and RNA corresponding to the endogenous target gene. Another nucleic acid molecule may contain sequences encoding alphaviral structural proteins downstream from an alphavirus subgenomic promoter. Using such a system, viral particles containing only replicons with packaging signals will be produced at permissive temperatures in recombinant eukaryotic host cells. This is so because alphaviral structural proteins will only be produced at a permissive temperature. Numerous variations of the above would be apparent to one skilled in the art.

G. Specific Embodiments of the Invention

FIG. 1 shows a general overview of homologous recombination performed using a vector system of the invention. The vector system consists of two components: a 5' targeting construct (1) and a 3' targeting construct (2). The 5' targeting construct contains a region which shares substantial sequence homology with nucleic acid located 5' to a chromosomal, endogenous target gene (5' targeting sequence). Immediately 3' to the 5' targeting sequence is a 5' cis-acting replication element which allows for RNA replication after replicon transcription. 3' to the 5' cis-acting replication element is nucleic acid which encodes Alphaviral non-structural proteins 1–4. 3' to the nucleic acid encoding Alphaviral non-structural proteins 1–4 is a resistance marker cassette, which is operably linked to an Alphaviral subgenomic promoter ($P_{SG}$), located between two loxP recombination sites. Finally, another subgenomic promoter ($P_{SG}$) and a 3' targeting sequence are located at the 3' end of the 5' construct.

The 3' targeting construct contains a region which shares substantial sequence homology with nucleic acid located 3' to the same chromosomal, endogenous target gene (5' targeting sequence). Immediately 3' to the 5' targeting sequence is a 3' cis-acting replication element which allows for RNA amplification after replicon transcription. Nucleic acid encoding a polyA stretch ($A_n$) is located immediately 3' to the 3' cis-acting replication element. Further, nucleic acid encoding a Hepatitis delta virus antigenomic ribozyme is located 3' to the polyA stretch, further followed by a transcriptional terminator and polyadenylation signal. Finally, a 3' targeting sequence is located at the 3' end of the 3' construct.

The resistance marker inserted into the endogenous nucleic acid by the 5' targeting construct is deleted by CRE recombinase mediated recombination. (See Sauer, U.S. Pat. No. 4,959,317.)

In the embodiments shown in FIG. 1 nucleic acid corresponding to the endogenous promoter is used as part of a targeting sequence. Thus, homologous recombination leaves the endogenous promoter unaltered.

One positive-negative selection scheme that is especially useful in the practice of the methods of the invention is set out in FIGS. 5A–5B. In the embodiments of the invention shown in this figure, each targeting construct contains at it's ends nucleic acid homologous that of the integration site, referred to herein as "targeting sequences". In a first step, the 3' end of the endogenous target gene locus undergoes homologous recombination with a 3' targeting construct which results in the insertion of a cis-acting sequence 3' to the target gene. Nucleic acid lying 3' to the endogenous target gene coding region is used as the 3' targeting sequences of the 3' targeting construct. Further, DNA which corresponds to the 3'-untranslated region of the endogenous target gene RNA is used as the 5' targeting sequence of the 3' targeting construct.

In a second step, the 5' end of the endogenous target gene locus undergoes homologous recombination with a 5' targeting construct containing nucleic acid encoding a replicase and a negative selection marker for counter-selection of cells in which this construct has integrated by non-homologous recombination. The 5' untranslated region of the endogenous target gene is used as the 3' targeting sequence of the 5' targeting construct. Several kilobases of nucleic acid 5' to the transcription start (ending with nucleotide-1 relative to the transcription start of the endogenous target gene) is used as the 5' targeting sequence of the 5' targeting construct. This 5' targeting sequence will often span the entire endogenous target gene promoter region.

As part of the second step discussed above, a third vector construct integrates randomly into endogenous nucleic acid (i.e., no targeting sequences are present in this vector construct). This vector construct encodes an alphaviral replicon under transcriptional control of an RNA polymerase II promoter. Further, the replicon contains a positive selection marker operably linked to a subgenomic promoter. Both replication of this entire RNA replicon, as well as formation of subgenomic RNA (encoding the positive selection marker) is dependent on the alphavirus replicase. Thus, this positive selection marker will only be expressed in the presence of the nsP 1–4 gene products. As a result, only recombinant eukaryotic host cells in which the 5' targeting construct have integrated into cellular nucleic acid by homologous recombination on the same allele already harboring the integrated 3' targeting construct and the vector construct containing the positive selection marker via random integration will be identified by a positive-negative selection system.

The resulting cell produced after performed these three chromosomal integrations will have a replicon-like arrangement within the chromosome. Using the strategy set out above, homologous recombination can be used to increase expression of the endogenous target gene without alteration or recombination of any of the endogenous target gene coding sequences. Further, in the scheme shown in FIGS. 5A–5B, replicon-like integrated nucleic acid is expressed from the endogenous target gene promoter.

Once the replicon has been transcribed from the endogenous target gene locus, additional RNA replications can occur to amplify the replicon and to produce replicons with both strand polarities.

As shown in FIG. 3, sections (7)–(8), (10), and (12)–(13), the endogenous target gene coding region will only be expressed after partial replication of a full-length RNA molecule. This partial replication of the full-length RNA molecules is driven by a cis-acting sequence composed of RNA (e.g., an alphaviral subgenomic promoter sequence).

In other embodiments of the invention, at least one of the targeting constructs is structured such that a resistance marker is co-transcribed with the endogenous gene coding region as part of the same initial RNA transcript. In such an instance at least one internal ribosome entry site (IRES) will generally be included to allow for translation of coding region(s) 3' to the 5' most coding region of the RNA when these RNA are not replicated using a subgenomic promoter.

Systems which use IRESs to allow for translation of multiple polypeptides from a single RNA species are known in the art. Hobbs et al., *Biochem. Biophys. Res. Commun.* 252:368–372 (1998), for example, describe an expression vector, designated pEFIRES-P, which encodes RNA structured in a fashion similar to that discussed immediately above. More specifically, the vector described in Hobbs et al. is designed for the stable expression of recombinant protein in mammalian cells. Both the recombinant cDNA and a puromycin resistance gene are transcribed from this vector as a single mRNA driven by the human polypeptide chain elongation factor 1-α promoter. The mRNA produced from this vector contains an IRES to ensure translation of both the recombinant cDNA and the puromycin resistance gene.

In one specific embodiment, the 3' targeting construct is designed to insert a resistance marker, operably linked to an IRES, downstream from an endogenous gene coding region. Thus RNA corresponding to this resistance marker is located near the 3' end of RNA corresponding to the endogenous gene coding region and is translated from the IRES. As a result, RNA molecules which encode the product of the endogenous gene will also encode the resistance marker in a translatable format.

A 3' targeting construct for producing recombinant cells via homologous recombination could be structured similarly to the 3' targeting construct shown in FIGS. 6A–6B but the negative selection marker could be omitted and the positive selection marker (marker 1) would be operably linked to nucleic acid encoding an IRES. Similarly, the RNA corresponding to the endogenous target gene could also be positioned so that it is translated via an IRES.

In a related embodiment, the endogenous gene product is produced as a fusion protein linked to the resistance marker. Depending on the particular application, these two proteins may or may not be separated by proteolytic cleavage.

In another related embodiment, the expression product of the endogenous gene is a functional RNA which is expressed as single nucleic acid molecule along with RNA encoding a resistance marker. In this instance, translation of resistance marker RNA can occur in one of several ways. First, the resistance marker can be located near the 5' end of the RNA and translated without the aid of an IRES. Second, the resistance marker can be located at a position other than the 5' end of the RNA but the RNA is cleaved (e.g., by a ribozyme) resulting in the production of an RNA molecule with the resistance marker located near the 5' end. Third, the RNA can contain an IRES which allows for the initiation of translation from an internal site in the molecule.

The sequences of a number of nucleic acids which can be used as IRESs are known in the art. (See, e.g., Jespersen et al., *Gene* 239:227–235 (1999); Martines-Salas, *Curr. Opin. Biotechnol.* 10:458–564 (1999); Isoyama et al., *J. Gen. Virol.* 80(Pt 9):2319–2327 (1999).)

III. Amplified Expression Products

While the methods of the invention do not, per se, result in gene amplification, RNA molecules which encode the endogenous target gene are effectively amplified by being included as a component of a replicable RNA molecule. Further, large numbers of translatable RNA copies of the endogenous target gene, or a subportion thereof, are produced from the subgenomic promoter.

The endogenous target gene products coded for and expressed by the replicons can be a wide variety of RNAs or polypeptides and include antisense and ribozyme RNAs, regulatory enzymes, structural protein, regulatory proteins and therapeutic proteins. These gene products may be expressed in their native form or from gene fusions.

When the replicon encodes an RNA molecule which is intended to inhibit the expression or activity of an endogenous target gene (e.g., antisense RNA), the recombinant eukaryotic host cells will generally be designed to express an RNA molecule in a format where the RNA does not have the functional properties of the RNA normally transcribed from the endogenous target gene. For example, when an antisense construct for a coding sequence is designed, the RNA replicated from the subgenomic promoter may be in antisense format and, further, may only represent part of the coding sequence of the endogenous target gene. In such an instance, the targeting sequences can be designed to delete part of or disrupt the coding region of the endogenous target gene.

Untranslated antisense RNA molecules can be used to inhibit translation of mRNA expressed in recombinant eukaryotic host cells. The use of antisense nucleic acid molecules to regulate gene expression is known in the art (see, e.g., Kawamata, H. et al., *Br. J. Cancer* 77:71–78 (1998); Bechler, K., *Biochem. Biophys. Res. Commun.* 241:193–199 (1997); Urakami, S. et al., *Biochem Biophys. Res. Commun.* 241:24–30 (1997)) and the use of the present vectors to construct recombinant eukaryotic host cells which express antisense RNAs is within the scope of the invention. Along these lines, Johnson et al., *Proc. Natl. Acad. Sci.* 96:13399–13403 (1999), for example, have recently shown that production of antisense nucleic acid using a Sindbis expression system can inhibit gene expression in mosquitos.

Replicons produced by the recombinant eukaryotic host cells can also be designed to produce the expression product of the endogenous target gene as a fusion product. For example, when the endogenous target gene expression product is an intracellular polypeptide, a signal peptide may be added to the polypeptide expression products of the replicons to allow for extracellular transport or localization to a specific intracellular compartment. Similarly, when altered cell transport or localization is desired, nucleic acid encoding the signal peptide normally associated with an endogenous target gene can be either replaced with a heterologous signal peptide or deleted. In such instances, the targeting sequences can be designed to make the desired additions or changes to the coding sequence of the endogenous target gene.

In many instances, it will also be advantageous to produce polypeptide expression products of endogenous target genes fused to amino acid sequences which improve stability and persistence in the recombinant eukaryotic host cell, during purification, or during subsequent handling and storage. A region may also be added to the polypeptide to facilitate purification. Such signal peptides may be designed with or without specific protease sites such that the signal peptide is amenable to subsequent removal.

The nucleic acid encoding the expression product of the endogenous target gene may also be fused to nucleic acid encoding at least a portion of the Fc region of an immunoglobulin. For example, the fusion protein expression products may contain an amino-terminal portion of polypeptides encoded by the endogenous target gene and a carboxy terminal portion derived from an Fc region. In these fusion proteins, the Fe region will often be limited to the hinge region and the $C_H2$ and $C_H3$ domains.

The nucleic acid encoding the endogenous target gene may also be fused to a hexa-histidine (HIS) peptide, such as the tag provided in the pQE vector (Qiagen, Inc.), among others, many of which are commercially available. This HIS peptide provides for convenient purification of the fusion protein.

In most instances, the endogenous target genes selected for expression modification will encode polypeptides. These polypeptides may be encoded by genes in the cells of any eukaryotic organism (e.g., yeasts and other fungi, algae, protists, plants, animals).

In many instances, the endogenous target genes will encode polypeptides useful for therapeutic applications. Such therapeutic polypeptides include members of the interleukin family of proteins and colony stimulating factors such as interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interleukin-17 (IL-17), interleukin-18, granulocyte colony stimulating factor (G-CSF), granulocyte-macrophage colony stimulating factor (GM-CSF), and macrophage colony stimulating factor (M-CSF). Therapeutic polypeptides also include antithrombin III, α-galactosidase, megakaryocyte-growth factor (M-GF), α-interferon (α-IF), β-interferon (β-IF), γ-interferon (γ-IF), tissue plasminogen activator (TPA), thrombopoietin (TPO), αI-antitrypsin, LDL-receptor, calcitonin, immunoglobins, protein kinase C, glucocerebrosidase, superoxide dismutase, urokinase, tyrosine hydroxylase, blood clotting factor V, blood clotting factor VII, blood clotting factor VIII, blood clotting factor IX, blood clotting factor X, blood clotting factor XIII, parathyroid hormone, nerve growth factors, FSH-β, TGF-β, tumor necrosis factor, glucagon, bone growth factor-2, bone growth factor-7, TSH-β, antithrombin III, globins, low density lipoprotein receptor, IL-2 receptor, IL-2 antagonists, immune response modifiers, glucagon, insulin, insulotropin, insulin-like growth factors, human growth hormone, apolipoprotein E apolipoprotein A-I, streptokinase, and DNase.

Fusion proteins of the invention also include proteins which have domains or regions derived from various different proteins. Examples of such fusion proteins are those containing domain II of Pseudomonas exotoxin. (See Pastan et al., U.S. Pat. No. 5,705,163. Domain II of Pseudomonas exotoxin will translocate across cell membranes. Using this protein, fusion proteins can be designed which allow for systemic delivery after expression. Further, a peptide which binds to a particular cell type can also be included in the fusion protein. Such a fusion protein could be expressed in one cell type and delivered via the circulatory or lymphatic systems, for examples, to other cell types.

In addition, instead of encoding an open reading frame, the endogenous target gene for which altered expression is desired may encode RNA molecules which are not normally translated. Examples of such untranslated RNA molecules include tRNA molecules, rRNA molecules, and ribozymes. A considerable number of ribozyme sequences with defined catalytic activities are known in the art (see, e.g., Tanner, K., *FEMSMicrobiol. Rev.* 23:257–275 (1999): Narlikar, G. et al., *Biochemistry* 38:14192–14204 (1999)).

The invention further provides methods for producing cells which exhibit increased expression of endogenous genes which lead to the production of additional products. Further included within the scope of the invention are cells produced by these methods, vector constructs used to produce these cells expression products of the amplified genes, and products produced by the expression products of the amplified genes. As an example, methods of the invention may be used to amplify endogenous genes involved in the production of cellular products such as taxol. In such an instance, genetic loci of cells of *Taxus chinensis* or *Taxus cuspidata* may be modified using methods of the invention to increase the expression of endogenous genes involved in pathways which lead to taxol production. These cells may then be grown in culture and used to produce taxol (see U.S. Pat. No. 5,871,979.) Further, the modified cells can be "fed" various precursors or intermediates which result in the production of taxol derivatives. A number of taxol derivatives and intermediates are known in the art. (See. e.g., U.S. Pat. Nos. 5.965,739, 6,028,206 and 6,072,060 and PCT publication WO 99/33462.)

Thus, in one aspect, the invention provides methods for producing biological products, as well as derivatives of such biological products, which comprise increasing the expression of one or more endogenous genes in cells, wherein these one or more (e.g., one, two, three, four, five, six, seven, eight, nine, ten, etc.) endogenous genes lead to the production of one or more (e.g., one, two, three, four, five, six, seven, eight, nine, ten, etc.) biological products. As suggested above, these biological products can essentially be any products, or derivatives thereof which are produced as a result of the expression of one or more endogenous genes. In various embodiments, the invention includes cells, as well as methods for preparing such cells, which exhibit increased expression of one, two, three, four, five, six, seven, eight, nine, ten, fifteen, twenty, or more endogenous genes.

In certain instances, it will be desirable to increase the expression of an endogenous gene which encodes, for example, an enzyme involved in the rate limiting step of a series of reactions. Similarly, in certain instances, it will be desirable to the increased the expression of an endogenous gene which encodes a product that performs the first committed step in a reaction series. In other instances, it will be desirable to increased the expression of genes in "upstream" pathways to increase the intracellular production of precursors for a particular pathway. This will, in effect, increase the intracellular concentration of precursors which can then be used as substrates in "down-stream" reactions. Similarly, the expression of antisense RNA, for example, corresponding to mRNA of endogenous genes which encode expression products which metabolize precursors and/or intermediates of a desired cellular product can be used to decrease expression of these endogenous genes. This will again lead to increases in intracellular concentrations of precursors and/or intermediates of the desired product. As one skilled in the art would recognize, various combinations of the above are possible. Thus, in certain instances, the expression characteristics of more than one endogenous gene will be altered to produce cells which exhibit increased production of cellular products.

Examples of biological products which can be produced by cells modified by methods of the invention include carbohydrates, amino acids, nucleotides, nucleosides, anti-bacterial agents (e.g., antibiotics), anti-viral agents, anti-parasitic agents, anti-fungal agents, anti-malarial agents, amebicidic agents, anti-neoplastic agents (e.g., taxol), and modified forms of each of these agents.

In another aspect, the invention provides methods for regulating the activity of target genes by modifying the expression of regulatory proteins involved in the regulation of said target genes. Such regulatory proteins may be transcription activators or repressors. For example, a number of promoters can be activated by hypoxia-inducible factor 1, a heterodimer consisting of subunits HIF-1α and HIF-1β (see, e.g., Blanchard et al., *Mol. Cell. Biol.* 12:5373–5385 (1992); Wang & Semenza, *J. Biol. Chem.* 268:21513–21518 (1993); Wang et al., *Proc. Natl. Acad. Sci. USA* 92:5510–5515 (1995); European Patent Application EP 0919619A2). Thus, it would be clear to those skilled in the art, that replicon based activation of genes encoding gene regulatory proteins (activators or repressors) may be a means to regulate (activate or, respectively, repress) the activity of the respective target genes of said regulatory proteins. Replicon based activation of genes encoding gene regulatory proteins is a means to co-ordinately regulate the entire set of target genes regulated by said gene regulatory protein.

Thus, as discussed above, in one aspect, the invention includes methods for modifying cells which exhibit increased expression of endogenous genes, as well as vector constructs used in these methods, cells produced by these methods, expression products produced by these cells, products produced as a result of the altered expression of the one or more endogenous genes, and methods for producing products produced as a result of the altered expression of the one or more endogenous genes.

IV. Methods for Preparing Targeting Constructs and Recombinant Eukaryotic Host Cells The targeting constructs of the invention and vectors for amplifying these constructs may be prepared in accordance with any number of conventional methods. Thus, the nucleic acids of these constructs may be synthesized, isolated from natural sources, manipulated, cloned, ligated, subjected to in vitro mutagenesis, primer repair, or the like.

At various stages, the joined sequences may be cloned, and analyzed by restriction analysis, sequencing, or the like. Usually the construct will be carried on a cloning vector comprising a replication system functional in a prokaryotic host, e.g., *E. coli,* and a marker for selection, e.g., antibiotic resistance, in a host cell (see, e.g., pCYTts). Other functional nucleic acids may also be present, such as polylinkers, for ease of introduction and excision of the construct or portions thereof.

Introduction of the polynucleotide vectors into cells can be effected by methods described in standard laboratory manuals (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997). Chapter 16), including methods such as electroporation, DEAE-dextran mediated transfection, transfection, microinjection, cationic lipid-mediated transfection, electroporation, transduction, scrape loading, ballistic introduction, and infection. Methods for the introduction of exogenous nucleic acids into cells are discussed in Felgner, P. et al., U.S. Pat. No. 5,580,859.

Non-infective packaged RNA sequences can also be used to infect cells. These packaged RNA sequences can be introduced to cells by adding them to the culture medium.

V. Cells and Methods for Producing Endogenous Target Gene Expression Products

As noted above, the recombinant eukaryotic host cells of the invention can be used for the production of polypeptides and RNA molecules. Thus, the invention provides, in part, methods for producing polypeptides or RNA molecules encoded by endogenous cellular nucleic acid. These methods involve the introduction of vector constructs of the invention into eukaryotic cells and the expression of RNA corresponding to the endogenous target gene in a format which allows for RNA amplification. In one embodiment, amplification and expression of the RNA corresponding to the endogenous target gene is controlled by regulating the temperature to either repress or induce replicase activity.

The methods of the invention can be practiced in any recombination competent mammalian cell. Such cells may be defined functionally as those which are capable of homologously recombining DNA molecules which contain regions of substantial overlapping homology. In general, recombination competent cells either contain endogenous recombinases or are genetically engineered to contain such recombinases, as well as other necessary components required to mediate homologous recombination. Examples of recombination competent mammalian cells include endothelial cells, kidney cells (e.g., 293 cells and 293T cells, as well as other derivatives of 293 cells), epithelial cells, myoblasts, hepatocytes, leukocytes, hematopoietic stem cells, fibroblasts, COS cells, Vero cells, Baby Hamster Kidney (BHK) cells, HeLa cells, Chinese hamster ovary cells (CHO), cells derived from fetal tissues, and cells generated by cell fusion (e.g., hybridomas).

When a promoter normally associated with an endogenous gene is used to drive transcription of a replicon of the invention, the endogenous promoter will be one which exhibits at least some constitutive or inducible transcriptional activity in the eukaryotic cell. For example, when the endogenous target gene selected is the human erythropoietin gene, the cell line chosen for modification according to the methods of the invention should exhibit at least low levels of erythropoietin expression. A number of such cells are know in the art and include cells of the Hep 3B (ATCC Deposit No. HB 8064) and Hep G2 (ATCC Deposit No. HB 8065) lines. Further, one skilled in the art would know how to isolate and identify additional cells which produce erythropoietin. For example, such methods are disclosed in Sugimoto et al., U.S. Pat. No. 4,377,512.

When cells for use in the practice of the present invention are derived from tissues, these tissues will generally be selected by those skilled in the art on the basis that they contain cells which express the endogenous target gene at least at low levels. Again, using erythropoietin as an example, tissues which contain cells which express this protein include tissues of the uterus, kidney, liver, and lung. Further, human hematopoietic progenitors have also recently been shown to express erythropoietin (Stopka et al., *Blood* 91:3766–3772 (1998). Additionally, a number of human tumors, including hemangioblastomas, and cell lines derived from human tumors have been shown to express erythropoietin (see, e.g., Krieg et al., *Blood* 92:3388–3393 (1998) and Goldberg et al., *Proc. Natl. Acad. Sci., USA* 84:7972–7976 (1987)).

When recombinant eukaryotic host cells of the invention are intended to be inserted into an individual, these cells will generally be from either another individual of the same genus and species or the same individual into which the cells will be inserted. Cells may be obtained from an individual by any number of means including surgical means and tissue biopsy.

Further, the cells selected for modification will generally be ones in which the RNA amplification system used is functional. Alphavirus vectors, for example, are known to have a wide host range. Sindbis virus, in particular, infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W. Schlesinger. Ed., Academic Press, (1980), pp.583–621). Thus, numerous eukaryotic cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be either selected (Zang, M. et al., *Bio/Technology* 13:389 (1995)) or genetically engineered (Renner W. et al., *Biotech. Bioeng.* 47:476 (1995); Lee K. et al. *Biotech. Bioeng.* 50:336 (1996)) to grow in serum-free medium, as well as in suspension. Thus, these cells may be particularly useful when a gene has been integrated into their genomes and the methods of the invention are used at a later time to alter expression of this gene.

When the eukaryotic cell which contains the endogenous target gene selected for altered expression is a yeast or plant cell, for example, it will be advantageous to use a vector system which functions in such cells. One such system would use genetic elements derived from an alphaviral-like virus such as the Brome Mosaic Virus (see, e.g., Sullivan et al., *J. Virol.* 73:2622–2632 (1999); O'Reilly et al., *J. Virol.* 72:7160–7169 (1998)).

When mammalian cells are used as recombinant eukaryotic host cells for the production of polypeptides and RNA molecules, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

The selection of a cell suited for a particular application will vary with a number of factors including the polypeptide or RNA molecule which is expressed.

In one aspect, the present invention provides methods for producing polypeptides and RNA molecules comprising introducing nucleic acid molecules of the invention into eukaryotic cells and incubating these cells at a permissive temperature. In a related aspect, the invention provides purified polypeptides and RNA molecules produced according to methods of the present invention.

Depending on the molecule which is expressed, the molecule may be obtained either from the culture supernatant or by lysing the recombinant eukaryotic host cells. When the expression product is a protein, it will often be possible to obtain the expression product from the culture supernatant. This will be so even when the protein does not have a naturally associated secretory signal. Codons encoding such a signal can be added to the vector sequences of the invention and will result in the expression of a fusion protein which will be secreted from the recombinant eukaryotic host cell. Nucleotide sequences encoding such leader sequences are known in the art and are publically available (see, e.g., pPbac and pMbac vectors, STRATAGENE 1997/1998 CATALOG, Catalog #211503 and #211504, Stratagene, 11011 North Torrey Pines Road, La Jolla, Calif. 92037, USA).

Recombinant eukaryotic host cells may also be infected with packaged or unpackaged RNA molecules which have either been transcribed from endogenous genetic loci modified by methods of the invention or replicated from such transcribed molecules. Further, when a temperature-sensitive replicase is used, these cells may be infected at a restrictive temperature and then later shifted to a permissive temperature to activate high level expression of the endogenous target gene. The endogenous target gene expression product may then be recovered and purified by any suitable means.

The endogenous target gene expression product can be recovered and purified from recombinant eukaryotic host cell cultures by methods known in the art including ammonium sulfate precipitation, anion or cation exchange chromatography, phosphocellulose chromatography, hydrophobic interaction chromatography, affinity chromatography, hydroxylapatite chromatography, and high performance liquid chromatography. Methods for purifying proteins are described in numerous sources (see, e.g., Celis, J., ed., CELL BIOLOGY, Academic Press, $2^{nd}$ edition, (1998)).

Methods for purifying RNA molecules are also known in the art (see, e.g., Celis, J., ed., CELL BIOLOGY, Academic Press, $2^{nd}$ edition, (1998)). These methods include phenol/chloroform extraction, digestion with DNAses followed by precipitation of the undigested RNA molecules, and column chromatography (e.g., oligo dT column chromatography). Further, RNA molecules can be separated from other cellular material using the single-step guanidinium-thiocyanate-phenol-chloroform method described in Chomczynski and Sacchi, *Anal. Biochem.* 162:156–159 (1987).

A number of different bioprocess parameters can be varied in order to increase the amount of expression product produced during the cell culture process. The conditions under which the recombinant eukaryotic host cells are grown (e.g., medium composition, pH, oxygen concentration, agitation, and, for the case of anchorage-dependent cells, the surface provided and the carrier of that surface) prior to exposure to the nucleic acid molecules of the invention (e.g., packaged replicons) or induction of gene expression influence both the cell density achieved at a given time and the physiological state of the cells. These culture conditions will thus affect the expected cellular response to vector exposure or the induction signal (e.g., shifting to a permissive temperature). Further, the cell culture process-conditions mentioned above can be varied to maximize the production of expression product and, often, the characteristics (e.g., glycosylation pattern) of that expression product.

The overall cell culture process employed for the production of expression product can be implemented in a variety of bioreactor configurations (e.g., stirred-tank, perfused, membrane enclosed, encapsulated cell, fluidized bed, and air-lift reactors) and scales (from laboratory T-flasks to thousands of liters), chosen to accommodate the requirements of the host cell line utilized (e.g., anchorage dependency, $O_2$ concentrations), to maximize the production of expression product, and to facilitate subsequent recovery and purification of expression product.

The invention is also directed to the production of proteins and RNA molecules encoded by endogenous target genes using recombinant mammalian host cells grown in serum-free or protein-free culture media. For example, by long-term culture under conditions restricting serum access or selecting for suspension growth, CHO cell lines are selected which are able to grow in serum-free medium and/or in suspension (Zang. M. et al., *Bio/Technology* 13:389 (1995)). Further, by genetic modification of CHO K1 cells, a modified cell line designated CHO K1:cycE was obtained which grows as suspended single cells in protein-free culture media (Renner W. et al., *Biotech. Bioeng.* 47:476 (1995)). CHO mutants (e.g., LEC10 cells) have also been isolated which produce glycoproteins having different glycosylation patterns than those produced in parental CHO cells (Stanley, P., *Glycobiology* 2:99 (1992)). Alternatively, CHO cells capable of synthesize glycoproteins with correspondingly modified oligosaccharides may be obtained by genetic modifications which alter the activities of enzymes involved in oligosaccharide biosynthesis (Minch et al., *Biotechnol. Prog.* 11:348 (1995)).

Further, a number of different bioprocess parameters can be varied in order to alter the glycosylation pattern of polypeptide products produced by the recombinant eukaryotic host cells of the invention. These factors include medium composition, pH, oxygen concentration, lack or presence of agitation, and, for the case of anchorage-dependent cells, the surface provided. Thus, the glycosylation pattern of glycoproteins may be altered by choosing the cell in which these proteins are expressed and the conditions under which the recombinant eukaryotic host cells are grown.

As explained below, endogenous target gene expression products may also be produced in genetically engineered, non-human animals.

VI. Genetically Engineered Plants and Non-Human Animals

Genetically engineered pants and animals are currently used for the production of heterologous proteins (see, e.g., Tackaberry, E. et al., *Vaccine* 17:3020–3029 (1999); Rudolph, N., *Trends Biotechnol.* 17:367–374 (1999); Jeng, S. et al., *J. Dairy Sci.* 80:3167–3175 (1997); Limonta J. et al., *Immunotechnology* 1:107–113 (1995)). When transgenic animals are used, these proteins are often harvested from bodily fluids such as blood, milk and urine (Meade, H. et al., *Nat. Biotechnol.* 16:21–22 (1998); Kerr, D. et al., *Nat. Biotechnol* 16:75–79 (1998)).

The present invention also provides genetically engineered plants and non-human animals comprising cells which contain nucleic acid molecules of the present invention. These plants and animals will generally contain a vector system of the invention stably integrated into their somatic and germ line cells. A number of methods are known in the art for producing plants and animals containing vector systems of the invention in their germ line cells (see, e.g., Tackaberry, E. et al., *Vaccine* 17:3020–3029 (1999); Ingram, R. et al., *Plant Cell* 11:1047–1060 (1999); Hew, C. et al., U.S. Pat. No. 5,545,808; Jolicoeur, P., U.S. Pat. No. 5,574,206; Mintz, B., U.S. Pat. No. 5,550,316; Wagner, T. et al., U.S. Pat. No. 4,873,191). With respect to animals, for example, DNA molecules can be introduced by microinjection into a fertilized, mammalian oocyte between the one-cell and eight-cell stage of embryological development. These oocytes are then implanted in a suitable female to produce founder animals which will stably transmit the heterologous transgene through the germ line to the next generation. Southern blot analysis is generally used to determine whether the genome of any particular individual carries the heterologous DNA.

The genetically engineered plants and animals may also contain nucleic acid molecules of the invention exclusively in somatic cells. Recombinant eukaryotic host cells containing these molecules may be implanted into the organism or nucleic acid molecules may be introduced into cells of the plant or animal in vivo.

When a temperature-sensitive replicase is used, high level expression of the endogenous gene in the cells of a genetically engineered animal may be induced by altering the body temperature of all or part of the plant or animal from a restrictive one to a permissive one. When an animal is used in such a situation, the choice of the animal used will vary with a number of factors, including the restrictive and permissive temperatures of the replicase employed, and the normal body temperature of the animal to be genetically engineered. These animals may be either warm-blooded or cold-blooded (see, e.g., Hew, C. et al., U.S. Pat. No. 5,545,808).

When a warm-blooded animal contains a vector system of the present invention, the normal body temperature of the animal may be either a restrictive one or a permissive one. Further, in many instances expression of the endogenous target gene at a genetic locus where vector constructs of the invention have integrated will either be induced or repressed in only a portion of the animal at any one time. For example, when the normal body temperature of a warm-blooded animal is a restrictive temperature and the temperature sensitive replicase is "hot" sensitive, the animal may be kept under conditions in which its extremities (e.g., feet, arms, legs, etc.) or surface tissues are lowered to a permissive one.

When a warm-blooded animal having cells which contain a nucleic acid molecule of the invention has a normal body temperature which is a permissive one, the endogenous target gene at a genetic locus where vector constructs of the invention have integrated will generally be expressed in cells in internal regions of the animal. Such animals will be particularly useful for expressing the endogenous target gene in mammary gland and urothelial tissues. Kerr, D. et al. (*Nat. Biotechnol.* 16:75–79 (1998)), for example, describe the production of transgenic animals which express a heterologous gene in the cells of their urothelium. These animals excrete the foreign gene product in their urine. In such a situation, the product of the endogenous target gene is readily collectable from such animals. Similarly, high level expression of the endogenous target gene in mammary gland tissues can result in the gene product being excreted in significant quantities into the animal's milk.

The present invention thus further provides genetically engineered plants and non-human animals which contain a vector system of the invention in at least some of their cells. Also provided are genetically engineered plants and non-human animals which contain a vector system of the invention stably integrated into the genome of some or all the organism's cells. The invention also provides methods for producing genetically engineered plants and non-human animals comprising introducing cells containing a vector system of the invention into these organisms introducing a vector system of the invention into the cells of these organisms in vivo, or introducing a vector system of the invention into germ line cells to produce transgenic plants or animals containing cells Which exhibit altered expression of the endogenous target gene in their somatic and germ line cells.

The invention further provides both genetically engineered plants and non-human animals and expression products of endogenous genes produced by the organisms.

VII. Gene Therapy

The invention further provides methods for performing gene therapy on an individual (e.g., domesticated animal, human, etc.), as well as vector constructs for performing gene therapy. Delivery of the vector constructs into an individual may be either direct, in which case the individual is directly exposed to the vector constructs, or indirect, in which case, vector constructs are introduced into the cells first in vitro, then the cells containing these vector constructs are transplanted into the individual. These two approaches are known, respectively, as in vivo and ex vivo gene therapy. Thus, the invention further includes methods for performing gene therapy comprising introducing nucleic acid molecules which lead to alterations in the expression of endogenous genes. These alterations in gene expression can result in either increased or decreased expression. Increased expression will occur, for example, when a genetic locus is modified using methods of the invention to increase the production of RNA (e.g, mRNA) corresponding to an endogenous gene. Decreased expression can occur, for example, when RNA corresponding to one or both alleles in a cell, or group of cells, is expressed in an antisense format.

Further, as discussed above with respect to transgenic animals, temperature-sensitive replicases can be employed to regulate the expression of endogenous genes which reside at genetic loci where vector constructs of the invention have integrated. For example, when the normal body temperature of the individual to which vector constructs have been introduced is a restrictive temperature, and the temperature sensitive replicase is "hot" sensitive, regions of the individual's body which contain cells modified by methods of the invention may be lowered to a permissive temperature to induce expression of an endogenous gene.

In one application, keratinocytes or fibroblasts of a human individual are removed by tissue biopsy, vector constructs of the invention containing nucleic acid which renders the vector constructs capable of integrating into cellular nucleic acid and increase expression of genes which are expressed in these cells (e.g., interleukin-6, interleukin-18, nerve growth factor, type I collagen, matrix metalloproteinases-1, Bcl-2, etc.) are introduced and stably integrated into these cells in vitro by homologous recombination. These recombinant cells (i.e., recombinant eukaryotic host cell) are reimplanted in a location near the surface where body temperature is relatively stably maintained (e.g., an axilla). When increased gene expression is desired, the individual places a cold item, such as an ice pack or peltier element for a specified period of time over the location containing the recombinant cells to induce the production of RNA from the modified genetic locus. The amount of RNA from the modified genetic locus, will vary with factors such as the temperature which the recombinant cells at the locus are incubated at and the length of time that these cells remain at a permissive temperature.

The actual temperature of the item which is placed in contact with the skin will vary with the type of temperature-sensitive mutation used, the individual, the location of the recombinant host cells, the level of gene expression desired, and other factors.

In specific embodiments, targeting constructs of the invention are directly administered in vivo, where they integrate into cells via homologous recombination. These targeting constructs can be introduced into cells by any of numerous methods known in the art (e.g., by infection using packaged viral particles, by direct injection of naked DNA, by use of microparticle bombardment (e.g., a gene gun; Biolistic, Dupont), etc). Further, targeting constructs can be targeted in vivo for cell specific uptake and expression, by targeting a specific receptor (see, e.g., PCT Publications WO 92/06180, WO 92/22635, WO92/20316, WO93/14188, and WO 93/20221 dated Oct. 14, 1993).

Having generally described the invention, the same will be more readily understood by reference to the following examples, which are provided by way of illustration and are not intended as limiting.

EXAMPLES

Materials and DNA Manipulations

The following enzymes and reagents were used in the experiments described in the examples which follow: T4 DNA ligase was obtained from New England Biolabs, Inc. (32 Tozer Road, Beverly, Mass. 01915); Taq DNA Polymerase, QIAprep Spin Plasmid Kit, QIAGEN Plasmid Midi Kit, QiaExII Gel Extraction Kit, QIAquick PCR Purification Kit were obtained from QIAGEN, Inc. (28159 Avenue Stanford, Valencia, Calif. 91355); QuickPrep Micro mRNA Purification Kit was obtained from Pharmacia; SuperScript One-step RT PCR Kit, fetal calf serum (FCS), bacto-tryptone and yeast extract were obtained from Gibco BRL; Oligonucleotides were obtained from Microsynth (Switzerland); restriction endonucleases were obtained from Boehringer Mannheim, New England Biolabs or MBI Fermentas; Pwo polymerase and dNTPs were obtained from Boehringer Mannheim. HP-1 medium was obtained from Cell culture technologies (Glattbrugg, Switzerland). All standard chemicals were obtained from Fluka-Sigma-Aldrich and all cell culture materials were obtained from TPP.

DNA manipulations were carried out by standard techniques. DNA was prepared either from 2 ml bacterial culture using the QIAprep Spin Plasmid Kit or from 50 ml culture using the QIAGEN Plasmid Midi Kit, both according to the protocols provided by the manufacturer. For restriction digest, DNA was incubated at least 2 hours with the respective restriction enzyme at a concentration of 5–10 units of enzyme per $\mu$g DNA under appropriate conditions (buffer and temperature as recommended by the manufacturer). Digests with more than one enzyme were performed simultaneously if reaction conditions were appropriate for all enzymes, otherwise consecutively. DNA fragments to be isolated for further manipulations were separated by electrophoresis in a 0.7 to 1.5% agarose gel, excised from the gel and purified with the QiaExII Gel Extraction Kit according to the protocol provided by the manufacturer. For ligation of DNA fragments, 100 to 200 pg of purified vector DNA were incubated overnight with a threefold molar excess of the insert fragment at 16° C. in the presence of 1 unit of T4 DNA ligase in the buffer provided by the manufacturer (total volume: 10–20 $\mu$l). $\frac{1}{10}$ to $\frac{1}{2}$ aliquot of the ligation reaction was used for transformation of *E. coli* XL1-Blue (Stratagene, 11011 North Torrey Pines Road, La Jolla, Calif. 92037, USA) by electroporation using a Gene Pulser (Bio-RAD, 1000 Alfred Nobel Drive, Hercules, Calif. 94547) and 0.1 cm Gene Pulser Cuvettes (Bio-RAD) at 200$\Omega$, 25 $\mu$F, 1.7 kV. After electroporation, the cells were incubated for 1 hour in 1 ml Luria broth medium (Luria, S. E., and Delbruck, M., *Genetics* 28:491–511 (1943)) with shaking, before plating on selective LB agar.

For transfection of eukaryotic cells using the lipofectamine method, cells were grown in 6-well cell culture plates medium (containing 2 ml DMEM supplemented with 10% fetal calf serum) to a confluency of 80%. Three-five $\mu$g of DNA to be transfected were pipetted into 250 $\mu$l of OPTI MEM II medium (Life Technologies. Rockville, Md.) and incubated for 15 minutes at room temperature. In parallel, 10 $\mu$l of lipofectamine 2000 was pipetted into 250 $\mu$l of OPTI MEM II medium (Life Technologies) and also incubated for 15 minutes at room temperature. The two solutions were then mixed and incubated at room temperature for a further 30 minutes. The transfection mix was pipetted onto the cell culture to be transfected and the culture was rocked for a few times. The cells were then incubated for 5 to 24 hours at 37° C., before the medium was exchanged.

For stable transfection of 293 cells and derivatives thereof by electroporation, cells were removed from an 80% confluent T-150 cell culture flask by trypsinization. The cells were washed once with 10 ml of growth medium (90% DMEM, 10% fetal bovine serum), resuspended in 10 ml of phosphate buffered saline (PBS; Life Technologies) and counted. $5 \times 10^6$ cells were suspended in 400 $\mu$l PBS and 5 $\mu$g of linearized DNA was then added. The suspension was transferred to a 0.2 cm electroporation cuvette (BioRad Laboratories, 4000 Alfred Nobel Drive, Hercules, Calif. 94547) and exposed to one electroporation pulse (1.2 kV, 25 $\mu$F) using a BioRad electroporation device (Gene Pulser II, Pulse Controller Plus, Capacitance Extender Plus). After electroporation, the cells were immediately transferred into a T-75 cell culture flask and incubated at 37° C. One day after electroporation, the medium was exchanged against selective medium.

Erythropoietin concentrations were determined using the Quantikine IVD human Erythropoietin ELISA Kit (R&D Systems, Minneapolis, USA).

Example 1

Screening for Suitable Candidate Cell Lines as Production Hosts for Replicon Based Activation of the Endogenous EPO Gene Suitable candidate cell lines for replicon based activation of the human EPO gene will generally need to have the following characteristics:

1. They have to be of human origin.
2. The EPO promoter has to be active within these cells, at least at a basal level, to provide for initial full length transcript of replicons.
3. The cell lines have to support replicon based expression technology (e.g., replication of alphaviral replicons and expression from viral subgenomic promoters).

Therefore, to identify promising candidate cell lines for replicon based activation of the human EPO gene, a three-step screening procedure was initiated, comprising the following steps:

Step 1

In a first screening round, human cell lines were investigated in parallel as to (i) activity of the EPO promoter (either by assaying for EPO in the supernatant using ELISA or by assaying for EPO mRNA using RT-PCR) and (ii) the ability to support of alphaviral expression technology. The latter was performed by infecting the cells with pSinRep5-GFP viral particles (containing the gene encoding *Aequorea victoria* green fluorescent protein (GFP) cloned into pSinRep5 (Invitrogen BV, The Netherlands)) and determining the number of "green" cells in the resulting population using a fluorescence activated cell sorting (FACS) device.

Step 2

Cell lines which support GFP expression from pSinRep5-GFP were transiently transfected with vectors pCYTts-GFP (PCT publication WO 99/50432) and pEPO$^2$-GFP (see Example 2) in order to test, whether GFP expression is also supported from these (non-cytopathic and temperature-sensitive) expression vectors. Transfections were performed using lipofectamine 2000. Five to twenty-four hours after transfection, cells were shifted to inducing conditions (in the case of pCYTts-derivatives to 29° C., in the case of pEPO$^2$- derivatives to 29° C. and a 1% oxygen containing atmosphere). After 24 hours of induction, GFP expression was monitored by FACS analysis. For pEPO²-GFP, specific transcription initiation at the EPO promoter was shown by transfecting a pEPO²-GFP derivative containing a deletion in the EPO promoter region as a negative control in parallel.

Step 3

Cells proven to support GFP expression from vectors pCYTts-GFP and pEPO²-GFP were assayed for recombinant EPO expression from vector pEPO². To this end, cells were transiently or stably transfected with pEPO² and the amount of EPO in the culture supernatant was determined using an ELISA after 3 days of induction.

Cells proving positive in all three of the above steps were used as candidate cell lines for replicon based activation of the endogenous EPO gene by homologous recombination. Cell lines that met all requirements best were Human Embryonic Kidney Cells 293 and derivatives thereof. Before gene activation by homologous recombinations in these cell lines is performed, a number of variants of pEPO² (homologous recombination 'mimic' constructs) are tested for EPO expression (see Example 9) in order to find the genetic configuration with the best performance in terms of EPO productivity.

Example 2

Construction of Expression Vector pEPO²-GFP

Vector pEPO²-GFP resembles vector pEPO² with the only exception that the EPO gene in pEPO² has been replaced with the *Aequorea victoria* green fluorescent protein gene (gfp) in order to have a quick and simple readout of gene expression from the vector. For construction, vector pEPO²-HDV was digested with SexAI, the 5' DNA overhangs were filled in with T4 DNA Polymerase, and the linearized fragment was digested afterwards with ClaI to obtain a 8636 bp fragment. The vector pCYTts-GFP was digested with Bsp120I, the 5' overhangs were filled in with T4 DNA Polymerase, and the linearized fragment was digested with ClaI/NgoAIV. The obtained 5674 bp fragment was ligated with the upper 8636 bp vector fragment to obtain pEPO²-GFP.

Example 3

Replicon-based Expression Under Initial Transcriptional Control of the EPO Promoter To investigate whether alphaviral replicon-based expression of a gene of interest may be initiated by transcription from the weak EPO promoter, expression plasmid pEPO-GFP was constructed. This plasmid contains an expression cassette comprising the green fluorescent protein (GFP) encoding sequence flanked on its 5' side by nucleotide nos. 1–7646 and on its 3' side by nucleotide nos. 11394–11703 of the Sindbis virus genome (Strauss et al., *Virol.* 133:92–110 (1984)). This expression cassette is immediately followed by a sequence stretch encoding 37 consecutive A-residues and the Hepatitis delta virus antigenomic ribozyme (Perrotta & Been, *Nature* 350:434–436 (1991)). The sequence encoding the Sindbis nonstructural proteins contains two point mutations (introducing amino acid changes P726S in nsP2 and G153E in nsP4) that render the viral replicase temperature-sensitive and non-pathogenic. The entire expression cassette is directly preceded by an engineered EPO enhancer/promoter region (nucleotide nos. 3451–3503 and nos. 261–388 according to GenBank Accession No. M11319).

The above-described expression vector was transiently introduced into cell line Hep G2 (Goldberg et al., *Proc. Natl. Acad. Sci.*, USA 84:7972–7976 (1987)) by the calcium phosphate, precipitation technique. The cells were grown under inducing conditions (in the presence 50 μM cobalt or under hypoxic conditions) at 30° C. or 37° C. and investigated daily for expression of the green fluorescent protein. Whereas in the cultures incubated at 30° C. green cells was detected after 2 days no expression of GFP was detected up to 6 days post transfection in the cells incubated at 37° C. Since the viral expression vector encodes a temperature-sensitive replicase (see above), this result clearly shows that GFP expression had occurred from the viral replicon.

Example 4

Construction of Expression Vector pEPO²·⁰

For construction of expression vector pBKSII(–)Pepo, the EPO promoter region (nucleotide 8 to 388 according the GenBank Accession. No. M11319) are amplified by PCR from Hep G2 (ATCC Deposit. No. HB-8065) chromosomal DNA using the oligonucleotides Pepo-FOR/Pepo-REV. The PCR product is cleaved with restriction enzymes NotI/BamHI and ligated into NotI/BamHI digested vector pBluescript II KS(–) (Stratagene). This vector is cleaved with MunI/EcoRV and ligated with the 2282 bp MunI/NruI fragment from vector pCYTts (see PCT publication WO 99/50432) resulting in plasmid pBKSII(–)PepoNSP5'.

The Sindbis subgenomic promoter region is amplified from vector pCYTts using the oligonucleotide pair Psub-FOR/Psub-REV. The 5' untranslated region of the EPO gene is amplified from Lambda HE1 phage lysate (ATCC Deposit. No. 40381) using the oligonucleotide pair EPO5'-FOR/Epo5'-REV. These PCR fragments are connected by SOE PCR using the oligonucleotides Psub-FOR and EPO5'-REV. The resulting fragment is cleaved with NotI/XbaI and ligated to NotI/XbaI digested vector pBluescript II KS(–) to obtain plasmid pBKSII(–)PsubEPO5'.

The 3' untranslated region of the EPO gene is amplified from Lambda HE1 phage lysate using the oligonucleotide pair EPO3'-FOR/Epo3'-REV. Digestion of the resulting PCR product with XbaI/XhoI and ligation with XbaI/XhoI digested vector pBKSII(–)PsubEPO5' results in plasmid pBKSII(–)PsubEPO5'+3'. The latter is cleaved with XbaI/BglII and ligated to the 1761 bp XbaI/BglII fragment encompassing Exons 2–5 of the EPO gene (nucleotide 1197 to 2957 according to GenBank Accession No. M11319) to obtain plasmid pBKSII(–)PsubEPO. The latter is cleaved with Eco47III/BamHI and ligated with the 5928 bp Eco47III/BamHI fragment from vector pCYTts to obtain plasmid pBKSII(–)NSP'EPO.

The EPO enhancer region (nucleotide 1028 to 1541 according to GenBank Accession No. AF053356) is amplified by PCR from Hep G2 chromosomal DNA using the oligonucleotide pair Enh-FOR/Enh-REV. The PCR product is cleaved with XhoI/KpnI and ligated into XhoI/KpnI cleaved vector pBluescript II KS(–) to obtain plasmid pBKSII(–)Enh. Upon cleavage with XhoI and dephosphorylation of DNA 5' ends, this vector is ligated with the 1146 bp XhoI/SalI fragment from plasmid pMC1neoPolyA (Stratagene, 11011 North Torrey Pines Road, La Jolla, Calif. 92037, USA; Thomas & Capecchi, *Cell* 51:503–512 (1987)). The ligation product where the EPO enhancer region is located downstream of the neo cassette is designated pBKSII(–)neoEnh. Vector pCYTts is cleaved with Bsp120I/NaeI and upon filling in the recessed 3' terminus, the vector fragment is recircularized by ligation to obtain plasmid pCYTΔBsp120I/NaeI.

The Hepatitis delta virus antigenomic ribozyme (Perrotta & Been, Nature 350:434–436(1991);Dubensky et al., *J. Virol.* 70:508–519(1996)) is obtained by annealing the 5' phosphorylated synthetic oligonucleotides HDV-FOR and HDV-REV. Plasmid pCYTΔBsp120I/NaeI is cleaved with EcoRI and ligated to the HDV-FOR/HDV-REV oligonucleotide duplex in the orientation that regenerates the EcoRI site adjacent to the $A_{37}$ stretch. From the resulting plasmid, the region encompassing the Sindbis 3' terminus, the $A_{37}$ stretch, the HDV sequence and the SV40 polyadenylation signal is amplified by PCR using the primers SIN3'-FOR and SV40-REV. The PCR product is cleaved with HindIII/XhoI and ligated into HindIII/XhoI digested plasmid pBKSII(−)neoEnh to obtain vector pBKSII(−)SIN3'neoEnh. This vector is cleaved with NotI/SalI and ligated with the 9139 bp NotI/XhoI fragment from plasmid pBKSII(−)NSP'EPO to get vector pBKSII(−)nsP-EPO-neo. For construction of expression vector pEPO$^{2.0}$, pBKSII(−)nsP-EPO-neo is cleaved with NotI/Eco47III and ligated with the 1793 bp NotI/Eco47III fragment from plasmid pBKSII(−)PepoNSP5'.

Example 5

Construction of Expression Vector pEPO$^2$ and pEPO$^2$-puro

For construction of expression vector pBKSII(−)Pepo, the first part of the EPO promoter region (nucleotide 8 to 287 according the GenBank Accession No. M11319) was amplified by PCR reaction from Hep G2 (ATCC Deposit. No. HB-8065) chromosomal DNA using the oligonucleotides Pepo-FOR/Pepo-REV3. The second part of the EPO promoter (nucleotides 251–388 according to GenBank Accession No. M11319) and the 5'Sindbis sequence (nucleotides 1–46; Strauss et al. (1984), Virology 133:92–110) were amplified by PCR reaction from pEPO-GFP using the oligonucleotide pair Pepo-FORX/PepoREVY. These two PCR fragments were assembled by SOE PCR using oligonucleotides Pepo-FOR/PepoREVY. The PCR product was cleaved with restriction enzymes NotI/BamHI and ligated into the NotI/BamHI digested vector pBluescript II KS(−) (Stratagene). This vector was cleaved with MunI/EcoRV and ligated with the 2282 bp MunI/NruI fragment from vector pCYTts (see PCT publication WO 99/50432) resulting in plasmid pBKSII(−)PepoNSP5'.

The Sindbis subgenomic promoter region was amplified from the vector eCYTts-GFP (a derivative of pCYTts-GFP carrying an additional puromycin resistance marker within the vector backbone region) using the oligonucleotide pair Psub-FOR/Psub-REV. The 5' untranslated region of the EPO gene was amplified from Hep G2 chromosomal DNA using the oligonucleotide pair EPO5'-FOR/EPO5'-REV. These PCR fragments were connected by SOE PCR using the oligonucleotides Psub-FOR and EPO5'-REV. The resulting fragment was cleaved with SstI/XbaI and ligated to the SstI/XbaI digested vector pBluescript II KS(−) to obtain plasmid pBKSII(−)PsubEPO5'.

The 3' untranslated region of the EPO gene was amplified from Hep G2 chromosomal DNA using the oligonucleotide pair EPO3'-FOR/EPO3'-REV. Digestion of the resulting PCR product with XbaI/XhoI and ligation with XbaI/XhoI digested vector pBKSII(−)PsubEPO5' resulted in plasmid pBKSII(−)PsubEPO5'+3'. The latter was cleaved with XbaI/BglII and ligated to the 1761 bp XbaI/BglII fragment encompassing Exons 2–5 of the EPO gene (nucleotide 1,197 to 2,957 according to GenBank Accession No. M11319) to obtain plasmid pBKSII(−)PsubEPO. The latter was cleaved with Eco47III/BamHI and ligated with the 5928 bp Eco47III/BamHI fragment from vector pCYTts to obtain plasmid pBKSII(−)NSP'EPO.

The EPO enhancer region (nucleotide 53,108 to 53,621 according to GenBank Accession No. AF053356) was amplified by PCR from Hep G2 chromosomal DNA using the oligonucleotide pair Enh-FOR/Enh-REV. The PCR product was cleaved with XhoI/KpnI and ligated into the XhoI/KpnI cleaved vector pBluescript II KS(−) to obtain plasmid pBKSII(−)Enh. Upon cleavage with XhoI and dephosphorylation of DNA 5' ends, this vector was ligated with the 1146 bp XhoI/SalI fragment from plasmid pMC1neoPolyA (Stratagene, 11011 North Torrey Pines Road, La Jolla, Calif. 92037, USA; Thomas & Capecchi, *Cell* 51:503–512 (1987)). The ligation product where the EPO enhancer region is located downstream of the neo cassette was designated pBKSII(−)neoEnh.

Vector pCYTts was cleaved with Bsp120I/NaeI and upon filling in the recessed 3' terminus, the vector fragment was recircularized by ligation to obtain plasmid pCYTΔBsp120I/NaeI. The Hepatitis delta virus antigenomic ribozyme (Perrotta & Been, *Nature* 350:434–436 (1991); Dubensky et al., *J. Virol.* 70:508–519 (1996)) was obtained by annealing the 5' phosphorylated synthetic oligonucleotides HDV-FOR and HDV-REV. Plasmid pCYTΔBsp120I/NaeI was cleaved with EcoRI and ligated to the HDV-FOR/HDV-REV oligonucleotide duplex in the orientation that regenerates the EcoRI site adjacent to the $A_{31}$ stretch. From the resulting plasmid, the region encompassing the Sindbis 3' terminus, the $A_{31}$ stretch, the HDV sequence and the SV40 polyadenylation signal was amplified by PCR using the primers SIN3'-FOR and SV40-REV. The PCR product was cleaved with HindIII/XhoI and ligated into HindIII/XhoI digested plasmid pBKSII(−)neoEnh to obtain vector pBKSII(−)SIN3'neoEnh. This vector was cleaved with NotI/SalI and ligated with the 9139 bp NotI/XhoI fragment from plasmid pBKSII(−)NSP'EPO to generate vector pBKSII(−)nsP-EPO-neo. For construction of expression vector pEPO$^2$, pBKSII(−)nsP-EPO-neo was cleaved with NotI/Eco47III and ligated with the 1793 bp NotI/Eco47III fragment from plasmid pBKSII(−)PepoNSP5'.

The expression vector pEPO$^2$-puro contains a puromycin expression cassette upstream of the EPO promoter region. The puromycin expression cassette (*Streptomyces alboniger* puromycin-N-acetyl-transferase (pac) gene between the SV40 early promoter and polyadenylation signals) was amplified from vector pPUR (Clontech Laboratories Inc.) using the oligonucleotide pair 5'SV40PUR/SV40puro-REV. The resulting PCR product was cleaved with NotI and ligated with the NotI digested and dephosphorylated pEPO$^2$ vector fragment. The ligation product resulted in expression vector pEPO$^2$-puro.

Example 6

Construction of a 'Homologous Recombination Mimic Cell Line':Stable Transfection of Hep G2 Cells with pEPO$^2$ and pEPO$^{2.0}$ Stable Transfection of Hep G2 Cells with pEPO$^2$ and pEPO$^{2.0}$ The human hepatoma cell line Hep G2 is stably transfected with either pEPO$^2$ or pEPO$^{2.0}$ DNA using the standard Ca-phosphate precipitation protocol: 20 μg of pEPO$^2$ or pEPO$^{2.0}$ DNA are digested with NotI for at least 4 hours under the conditions recommended by the manufacturer. The DNA is purified by phenol/chloroform extraction followed by ethanol precipitation. Six μg of DNA in 30 μl H$_2$O are mixed with 30 μl of a 1 M $CaCl_2$ solution. After addition of 60 μl phosphate buffer (50 mM HEPES, 280 mM NaCl, 1.5 mM $Na_2HPO_4$, pH 7.05) the solution is mixed for 5 seconds, followed by incubation at room temperature for 25 seconds. The solution is immediately added to 2 ml growth medium containing 2% fetal calf serum (2% FCS medium). The medium of an 80% confluent Hep G2 culture in a 6-well plate is then replaced by the DNA containing medium. After incubation for 5 hours at 37° C. in a 5% $CO_2$ atmosphere, the DNA containing medium is replaced by 2 ml of 2% FCS medium containing 15% glycerol. The glycerol containing medium is removed after 30 seconds and the cells are washed with 5 ml growth medium containing 10% FCS. Finally, 2 ml of fresh growth medium containing 10% FCS are added and the cells are incubated over night at 37° C. in a 5% $CO_2$ atmosphere. The cells are then trypsinized, transferred to a tissue culture dish (150 mm diameter) and stably transfected cells are selected by addition of G418 (20 μg/ml) to the growth medium. After completion of the selection process, G418 resistant clones are separated (cloned) by standard cell culture techniques.

Production of Recombinant EPO

Hep G2 cells stably transfected with either $pEPO^2$ or $pEPO^{2.0}$ DNA are grown at 37° C. in cell culture flasks until 80% confluency. The temperature is then shifted to 29° C. and growth conditions known to induce the EPO promoter are applied (e.g. reduced oxygen pressure, addition of CoCl, MnCl, NiCl: see Goldberg et al., *Proc. Natl. Acad Sci. USA* 84:7972–7976 (1987); Blanchard et al., *Mol. Cell. Biol,* 12:5373–5385 (1992); Eckhard et al., *Ann. N.Y. Acad. Sci.* 718:50–63 (1994)). For comparison, Hep G2 cells not transfected with either $pEPO^2$ or $pEPO^{2.0}$ and a cell line not producing EPO (e.g., BHK-21) are treated in the same manner. EPO secreted to the supernatant is detected using a commercially available EPO ELISA Kit (R&D Systems, 614 McKinley Place NE, Minneapolis, Minn. 55413).

Example 7

Construction of a 'Homologous Recombination Mimic Cell Line': Stable Transfection of 293 Cells with $pEPO^2$ In order to mimic the replicon-activated EPO expression system present in the homologous recombinant host cell line, the human embryonic kidney cell line 293 was stably transfected with the 'mimic' construct $pEPO^2$ by electroporation. Ten μg of plasmid $pEPO^2$, prepared using the Plasmid Midi Kit (Qiagen, Germany), were linearized using restriction enzyme NotI and the linear DNA was purified using the QIAquick PCR purification Kit (Qiagen, Germany). Five μg of the purified DNA were used for electroporation of 293 cells. Recombinant cells were selected by incubation in the presence of 1 mg/ml G418.

After two weeks, when selection was complete, single cells of the G418 resistant population were transferred into the wells of a 96-well cell culture plate and further incubated until the confluency of the cells within the wells had reached 80%. The clones were split, each one being distributed to two 96-well plates, and one of the plates was incubated under inducing conditions (1% $O_2$, 29° C.). Three days later, the EPO concentrations in the culture supernatants were determined using an ELISA. Seventeen out of 415 clones screened were found to produce EPO at amounts significantly above the background level determined with untransfected 293 cells.

Cells prepared and screened by the methods set out above have been found to produce as much as about 60 μg/liter of EPO.

Example 8

Construction of a 'Homologous Recombination Mimic Cell Line': Stable Transfection of 293T Cells with $pEPO^2puro$ In order to mimic the replicon-activated EPO expression system present in the homologous recombinant host cell line, the human embryonic kidney cell line 293T, deviating from the 293 cell line by harboring a gene encoding SV40 large T antigen, was stably transfected with the 'mimic' construct $pEPO^2puro$ by electroporation. Ten μg of plasmid $pEPO^2puro$, prepared using the Plasmid Midi Kit (Qiagen, Germany), were linearized using restriction enzyme PacI and the linear DNA was purified using the QIAquick PCR purification Kit (Qiagen, Germany). Five μg of the purified DNA were used for electroporation of 293T cells. Recombinant cells were selected by incubation in the presence of 1 μg/ml puromycin. After one week, when selection was complete, single cells of the puromycin resistant population were transferred into the wells of a 96-well cell culture plate and further incubated until the confluency of the cells within the wells had reached 80%. The clones were split, each one being distributed to two 96-well plates, and one of the plates was incubated under inducing conditions (1% $O_2$, 29° C.). Three days later, the EPO concentrations in the culture supernatants were determined using an ELISA. Fifteen out of 64 clones screened were found to produce EPO at amounts significantly above the background level determined with untransfected 293T.

Cells prepared and screened by the methods set out above have been found to produce as much as about 30 μg/liter of EPO.

Example 9

Maximizing EPO Expression: Variations on the Expression System

In order to maximize EPO expression, as compared to the 'standard' expression cassette $pEPO^2$, a number of variants thereof are constructed, introduced into the respective host cell line, and compared to $pEPO^2$ in terms of EPO productivity. Modifications which are introduced include:

1. Presence/absence of the HDV ribozyme sequence at the 3' terminus of the alphaviral replicon.
2. All possible combinations of non-cytopathic mutations (e.g., nsP2(P726L), nsP2(P726S), etc.) and temperature-sensitive mutations (e.g., nsP4(G153E)) with each other and with the respective wild type alleles of the nsP genes.
3. A modified alphaviral replicon 5' terminus (e.g., like modifications found in defective interfering particles (Monroe & Schlesinger. *Proc. Natl. Acad. Sci. USA* 80:3279–3283 (1983))
4. Deletion of all or part of the nsP genes and co-expression of replicase from a different expression cassette (e.g., from pCYTts or from a regular expression cassette (i.e., nsP1–4 coding sequence under control of an RNA polymerase II promoter)) or from any other expression cassette.
5. Modification (e.g., shortening) of the 5' untranslated region of the EPO gene.
6. Inclusion on the replicon of a selection marker operably linked to a second subgenomic promoter or an internal ribosome entry site (IRES).

As would be clear to one of ordinary skill in the art, more than one of the above-mentioned modifications—and also other modifications not referred to herein (e.g., the introduction of elements which facilitate the export of the RNA from the nucleus to the cytoplasm of the cell (e.g., SV40 small t antigen intron), or RNA stabilizing elements) but which lead to increases in EPO expression levels—can be combined in the same expression system and the preferred combination of genetic elements will be defined on the basis of the influence of the respective elements on EPO expression.

In order to test the influence of the modifications listed above on the EPO expression level, the following plasmids were constructed (see FIGS. 9A–9C):

Construction of Expression Vector pEPO$^2$(-HDV)

For construction of the expression vector pEPO$^2$(-HDV) in which the Hepatitis delta virus antigenomic ribozyme sequence is omitted, the region encompassing the Sindbis 3' terminus, the $A_{31}$ stretch, the HDV sequence and the SV40 polyadenylation signal was amplified by PCR using the primers SIN3'-FOR/SV40-REV as described above. The PCR product was cleaved with HindIII/XhoI and ligated into pGEM®7Zf(-) (Promega) cleaved with HindIII/XhoI, resulting in plasmid pGEM7(-)SIN3'. From this vector a PCR fragment was amplified using primers -HDV/SV40-REV introducing an additional EcoRI site 5' of the SV40 terminator. The EcoRI/XhoI fragment (SV40 polyadenylation signal without HDV) was ligated into the EcoRI/XhoI cleaved plasmid pGEM7(-)SIN3', designated as vector pGEM7(-)SIN3'-HDV. The HindIII/XhoI fragment of this plasmid was ligated into the HindIII/XhoI cleaved pBKSII(-)neoEnh (see pEPO$^2$) to obtain plasmid pBKSII(-)SIN3'-HDVneoEnh. This vector was cleaved with NotI/SalI and ligated with the 9139 bp NotI/XhoI fragment from plasmid pBKSII(-)NSP'EPO to obtain vector pBKSII(-)nsP-EPO-neo-HDV. Vector pBKSII(-)nsP-EPO-neo-HDV was cleaved with NotI/Eco47III and ligated with the 1793 bp NotI/Eco47III fragment from plasmid pBKSII(-)PepoNSP5' resulting in expression vector pEPO$^2$-HDV.

Construction of Expression Vector pEPO$^2$ΔEB-HDV

For construction of a pEPO$^2$-HDV variant, where the 5,932 bp Eco47III/BamHI fragment of the Sindbis nonstructural proteins has been deleted, the pEPO$^2$-HDV vector was used. The vector was first digested with Eco47III and SalI and afterwards partially digested with BamHI. The resulting 10,022 bp Eco47III/BamHI fragment was isolated, the 5' overhangs were filled in with T4 DNA polymerase and the fragment was religated to obtain plasmid pEPO$^2$ΔEB-HDV. The sequence of the ligation junctions was confirmed by DNA sequence analysis.

Construction of Expression Vector pEPO$^2$w/onsP2mut-HDV

For construction of the expression vector pEPO$^2$ without the nsP2 mutation (Pro726Ser) the Eco47III/BamHI nsP-fragment of pCYTox-GFP (a derivative of pCYTts-GFP where this mutation has been deleted by PCR) was ligated into the Eco47III/BamHI vector pBKSII(-)PsubEPO (see pEPO$^2$). This vector was designated pBKSII(-)nsP'w/onsP2mut-EPO. This vector was cleaved with NotI/XhoI and ligated with the NotIlSalI fragment from plasmid pBKSII(-)SIN3'-HDVneoEnh to obtain plasmid pBKSII(-)nsPw/onsP2mut-EPO-neo-HDV. The 1793 bp NotI/Eco47III fragment of pBKSII(-)PepoNSP5'(see pEPO$^2$) was ligated into the NotI/Eco47III cleaved vector pBKSII(-)nsPw/onsP2mut-EPO-neo-HDV. The ligation product resulted in expression vector pEPO$^2$w/onsP2mut-HDV.

Construction of Expression Vector pEPO$^2$mut1-HDV

The vector pEPO$^2$mut1-HDV is another variant of the pEPO$^2$-HDV vector. It differs only through the absence of the ts6 mutation (G153E) in the Sindbis nsP4 gene (PCT publication WO99/50432). The vector pEPO$^2$-HDV was cleaved with ClaI/HpaI and the 11,748 bp vector fragment was ligated with the 4,206 bp ClaI/HpaI fragment from pEPO$^2$mut1-GFP (a variant of pEPO$^2$-GFP lacking the ts6 mutation) resulting in pEPO$^2$mut1-HDV.

Construction of Expression Vector pEPO$^2$wt-HDV

The expression vector pEPO$^2$wt-HDV is missing the nsP2 and ts6 mutations and has therefore the Sindbis wild type nsP genes. The vector $pEPO^2$-HDV was cleaved with ClaI/HpaI and the 11,748 bp vector fragment was ligated with the 4,206 bp ClaI/HpaI fragment from $pEPO^2$wt-GFP (a variant of $pEPO^2$-GFP) resulting in $pEPO^2$wt-HDV.

Construction of Expression Vectors $pEPO^2P_{SG}$puro and $pEPO^2mut1P_{SG}$puro The vector $pEPO^2P_{SG}$puro contains an additional second Sindbis subgenomic promoter region in the 3' untranslated EPO region in vector $pEPO^2$. This second subgenomic region is connected with the puromycin coding region. The vector pBS/5'$pEPO^2$ was obtained by digestion of $pEPO^2$ with NotI/XhoI and ligation of the 11,502 bp fragment into the NotI/XhoI digested vector pBS(w/oSacI). The pBluescript II KS(−) vector (Stratagene) derivative pBS(w/oSacI) was obtained by cleaving the pBluescript II KS(−) with SacI, filling in the 5' recessed ends with T4 DNA polymerase and recircularize the vector, so that the original SacI site was destroyed. The Sindbis subgenomic promoter region combined with the puromycin coding sequence was amplified by PCR from vector pCYTBB-puro (a derivative of pCYTts) using the primer pair subfor/subrev. The resulting PCR fragment was cleaved with SacI and ligated into the SacI digested, dephosphorylated pBS/5'$EPO^2$ vector. Upon cleavage with enzymes XhoI/NotI the 12,278 bp fragment out of this vector was ligated with the 4541 bp XhoI/NotI fragment of vector $pEPO^2$. This ligation results in $pEPO^2P_{SG}$puro.

The vector $pEPO^2mut1P_{SG}$puro is a variant of the vector $pEPO^2P_{SG}$puro, where the ts6 mutation of the Sindbis nsP4 gene is missing. The vector $pEPO^2$mut1-GFP (avariant of $pEPO^2$-GFP lacking the ts6 mutation) was digested with ClaI/HpaI. The resulting 4,206 bp fragment was ligated into the 12,613 bp ClaI/HpaI vector fragment of $pEPO^2P_{SG}$puro. The obtained vector is called $pEPO^2mut1P_{SG}$puro.

Construction of Expression Vector p5'$EPO^2$-HDV

Deletion of the 5' untranslated region of the EPO gene in the vector $pEPO^2$-HDV leads to the vector p5'$EPO^2$-HDV. The 3' region of the Sindbis nsP genes and the subgenomic promoter region were amplified from vector $pEPO^2$ using the oligonucleotide pair rrNSPHPA-FOR/rrNSPSOE. The 5' coding region of the EPO gene was amplified from vector $pEPO^2$ using the oligonucleotides rrEPO5'FOR/rrEPO5'REV. These PCR fragments were assembled by SOE PCR using the oligonucleotides rrNSPHPA-FOR/rrEPO5'-REV. The resulting PCR fragment was digested with HpaI/XbaI and ligated to the HpaI/XbaI digested fragment of vector $pEPO^2$-HDV to obtain the vector p5'$EPO^2$-HDV.

Construction of Expression Vectors $pEPO^2$tRNA-HDV and $pEPO^2$tRNAΔEB-HDV

The 5' Sindbis sequence of $pEPO^2$-HDV was replaced partly by a $tRNA^{Asp}$ (Monroe & Schlesinger, *Proc. Natl. Acad. Sci. USA* 80:3279–3283 (1983)) sequence in the $pEPO^2$tRNA-HDV construct. For this construction the EPO promoter region was amplified from $pEPO^2$ using oligonucleotides nhPeponot-FOR/nhPepotRNA-REV. The $tRNA^{ASP}$ sequence and the 5' region of the Sindbis nsP genes were amplified from pDH-EB (Bredenbeek et al., *J.*

*Virol.* 11:6439–6446 (1993)) by PCR using oligonucleotides nhPepotRNA-FOR/nhnsPEco-REV. These two PCR fragments were assembled by SOE PCR using the oligonucleotides nhPeponot-FOR/nhnsPEco-REV. The obtained PCR product was cleaved with NotI/Eco47III and ligated into the 14,159 bp NotI/Eco47III fragment of vector pEPO$^2$-HDV. The vector pEPO$^2$tRNA-HDV was cleaved with NotI/MunI and the resulted 464 bp fragment was used for ligation into the 9,596 bp NotI/MunI fragment from vector pEPO$^2$ΔEB-HDV. The obtained plasmid is named pEPO$^2$tRNAΔEB-HDV.

Construction of Expression Vectors pEPO$^2$IRESpuro-HDV and pEPO$^2$mut1IRESpuro-HDV In the vector pEPO$^2$IRESpuro-HDV, a cassette containing a synthetic intron, an internal ribosome entry site (IRES) of the encephalomyocarditis virus (ECMV) followed by the puromycin-N-acetyl-transferase coding region was introduced into the 3' untranslated EPO region. As preparation the vector pIRESpuro2 (Clontech Laboratories Inc.), which contains this above mentioned cassette, was modified to delete almost the whole multiple cloning site. The vector was cleaved with EcoRV/NotII, the 5' overhangs were filled in with T4 DNA polymerase and the fragment was recircularized to obtain vector pIRESpuro2delMCS.

The 11,411 bp NotI/XhoI fragment from pEPO$^2$-HDV was ligated into the NotI/XhoI digested pBS(w/oSacI) (see pEPO$^2$P$_{SG}$puro). This vector pBS5'EPO$^2$-HDV was cleaved with SacI and upon dephosphorylation of the DNA 3' ends the 13,102 bp fragment was ligated with the 1,691 bp fragment of pIRESpuro2delMCS. From the resulting pBS5'EPO$^2$IRESpuro-HDV vector the NotI/XhoI digested 13,104 bp fragment was ligated into the NotI/XhoI fragment of pEPO$^2$-HDV. This ligation product resulted in pEPO$^2$IRESpuro-HDV.

The vector pEPO$^2$mut1IRESpuro-HDV was constructed by ligation of the 15,992 bp SpeI/HpaI fragment of pEPO$^2$IRESpuro-HDV with the 1,653 bp SpeI/HpaI fragment of pEPO$^2$mut1-HDV.

Transfection of Candidate Cell Lines and Determination of Productivity

In order to find the optimal homologous recombination 'mimic' construct in terms of EPO productivity, candidate cell lines (e.g., 293, Hep G2 and derivatives thereof) are either transiently or stably transfected with the above-listed vectors. For transient transfections, the lipofectamine method is used, stable transfections are performed by electroporation. In the case of pEPO$^2$ΔEB-HDV and pEPO$^2$tRNAΔEB-HDV, the cell line is further transfected with a second construct providing for viral replicase. This construct may be either pCYTts or a regular expression cassette (i.e., the nsP1–4 genes under transcriptional control of an RNA polymerase II promoter). In the case of transient transfections, the cultures are induced for EPO production 24 hours after transfection. In the case of stable transfections, recombinant clones are selected, cloned (e.g., by limited dilution), grown up and induced for EPO production. Relative EPO productivities (measured by ELISA) conferred by the homologous recombination 'mimic' constructs are compared to each other. Genetic elements leading to an improvement of EPO productivity are included in the targeting fragments for homologous recombination.

Example 10

Activation of the Endogenous EPO Gene by RNA Replication

Construction of the 5' and 3' Targeting Fragments

The 3' untranslated region of the EPO gene is amplified from Lambda HE1 phage lysate using the primer pair EPO3'-FOR2/EPO3'-REV. The PCR product is cleaved with NotI/BglII and the resulting NotI/BglII fragment is ligated with the NotI/BglII vector fragment of pEPO$^2$. The resulting plasmid is cleaved with HindIII/SalI and ligated with the HindIII/XhoI fragment carrying the HSV-tk gene from plasmid pIC19R/MCI-TK (Chauhan & Gottesmann, *Gene* 120:281–286 (1992)). The BamHI/KpnI vector fragment of the resulting plasmid is then ligated with the 3' targeting sequence. The latter is obtained by PCR amplification of nucleotides 51,567 to 53,621 according to GenBank Accession No. AF053356 from Lambda HE1 phage lysate using the oligonucleotide pair Enh-FOR2/Enh-REV2 and subsequent cleavage with BamHI/KpnI. From the resulting plasmid, the 3' targeting fragment is prepared by cleavage with NotI.

The Sindbis subgenomic promoter and EPO 5' untranslated region is amplified from vector pEPO$^2$ using the primer pair Psub-FOR/EPO5'-REV2. The resulting fragment is cleaved with BamHI/KpnI and ligated with the BamHI/KpnI vector fragment of pBluescript II KS(−). The resulting plasmid is cleaved with XhoI/HindIII and ligated with the HindIII/XhoI fragment carrying the HSV-tk gene from plasmid pIC19R/MCI-TK (Chauhan & Gottesmann, *Gene* 120:281–286 (1992)). The resulting plasmid is cleaved with SacI/BamHI to be ligated to the 5' targeting sequence. The latter is obtained by amplification of nucleotides 56,604 to 58,742 according to GenBank Accession No. AF053356 from Hep G2 cells (ATCC No. HB-8065) using the oligonucleotide pair Pepo-FOR2/Pepo-REV and subsequent cleavage with SacI/BamHI. The resulting vector is digested with MunI/BamHI and ligated with the 7,293 bp fragment resulting from partial digestion of vector pCYTts with MunI/BamHI. From the resulting vector, the 5' targeting fragment is obtained by cleavage with NotI.

TABLE 1

Oligonucleotides

| Designation | Sequence | SEQ ID NO |
|---|---|---|
| Enh-FOR | d(GTTTTCTCGAGCCTCCAAATCCCCTGGCTC) | 2 |
| Enh-FOR2 | d(CCTCCGGATCCGTCGAGCCTCCAAATCCCCTGGCTCTG) | 3 |
| Enh-REV | d(AGAGGTACCTCCAACCGCACCTGTG) | 4 |
| Enh-REV2 | d(GGTGGGGTACCGCGGCCGCATCCTCTGAGCTCAGGAGTTTG) | 5 |
| EPO3'-FOR | d(GCTGTCTAGAGAGCAACTCTGAGATCTAAG) | 6 |
| EPO3'-FOR2 | d(GGGGAGCTCGCGGCCGCAAGCTTGGTGGGTCGACCAGGTGTGTCCACCTGGG) | 7 |
| EPO3'-REV | d(CCAACCCTCGAGGCCAGCCCCCATCCTGTC) | 8 |
| EPO5'-FOR | d(CAACACCACCACCAGAGTCCCTGGGCCACCC) | 9 |
| EPO5'-REV | d(GGACATTCTAGAACAGATAGCC) | 10 |
| EPO5'-REV2 | d(GGTGGGTACCGCGGCCGCAAGCTTGGTTGGCTCGAGGCTCCGCGCCTGGCCGGGG) | 11 |
| HDV-FOR | d(AATTCGGGTCGGCATGGCATCTCCACCTCCTCGCGGTCCGACCTGGGCATCCGAAGGAGGACGCACGTCCACTCGGATGGCTAAGGGAGC) | 12 |
| HDV-REV | d(AATTGCTCCCTTAGCCATCCGAGTGGACGTGCGTCCTCCTTCGGATGCCCAGGTCGGACCGCGAGGAGGTGGAGATGCCATGCCGACCCG) | 13 |
| Pepo-FOR | d(CCCGAGCTCGCGGCCGCTGGGCTTCCAGACCCAGC) | 14 |
| Pepo-FOR2 | d(GGTTGGGAGCTCGCGGCCGCGTTACTGCTGATTAGTATCTTGC) | 15 |
| Pepo-REV: | d(CCCGGATCCCCTCCCAATTGGTCGGCTGTTTGATTCAATAGTGTGTACTACGCCGTCAATGCGGCTCTGGCCGGGGTCGGGG) | 16 |
| Psub-FOR | d(GGGGAGCTCGCGGCCGCGGAGGAGCGCTGATTCGGTTACTTCCACAGCG) | 17 |

TABLE 1-continued

Oligonucleotides

| Designation | Sequence | SEQ ID NO |
|---|---|---|
| Psub-REV | d(CGGGGTGGCCCAGGGACTCTGGTGGTGGTGT TGTAGTATTAG) | 18 |
| SIN3'-FOR | d(CCAACCAAGCTTGTCGACGCCCCAATGATCC GACCAGC) | 19 |
| SV40-REV | d(CTCGACGGCTCGAGACATGATAAGATACAT) | 20 |

Example 11

Activation of the Endogenous EPO Gene by RNA Replication

Construction of the Progenitor Cell Line Targeting Fragment

The 1,146 bp XhoI/SalI neomycin cassette of pMC1neopolyA (Stratagene) was ligated into the XhoI cleaved, dephosphorylated vector pBluescript II KS(−) (Stratagene) to obtain plasmid pBSKS(−)neo. The 5' targeting sequence containing the EPO promoter region was obtained by PCR amplification of nucleotides 56,604 to 58,742 according to GenBank accession no. AF053356. PCR reactions were done using the oligonucleotide pairs PEPOlongFOR3/PEPOHIIIREV on Hep G2 chromosomal DNA and PEPOHIIIFOR/PEPOlongREV on plasmid pBSKSII(−)Pepo (see pEPO$^2$). These PCR fragments were connected by SOE PCR using the primers PEPOlongFOR3/PEPOlongREV3. The resulting fragment was cleaved with KpnI/XhoI and ligated into the KpnI/XhoI cleaved vector pBSKS(−)neo, resulting in pBSKS(−)PEPOlongneo.

The XhoI/HindII fragment carrying the HSV-TK gene from plasmid pIC19R/MC1-TK (Chauhan and Gottesmann (1992), Gene 120:281–286) was ligated into the XhoI/HindIII digested plasmid pBluescript II KS(−). The obtained vector pBSKS(−)HSV-TK was cleaved with HindIII/NotI and ligated to the EPO 5' untranslated region (nucleotides 56,369–56,604 according to GenBank accession no. AF053356). This fragment was amplified by PCR from vector pBSKS(−)PsubEPO5' (see pEPO$^2$) using oligonucleotides EPO5'un-FOR/EPO5'-REV3. The resulting vector pBSKS(−)HSV-TK EPO5'un was cleaved with XhoI/SstII and the obtained HSV-TK EPO5'un fragment was ligated into the SalI/SstII cleaved vector pBSKS(−)PEPOlongneo. From the resulting plasmid pBSKS(−)EPO3Vorläufer, the fragment for transfection of candidate cell lines (e.g., Hep G2, 293, etc.) was prepared by digestion with NotI (see FIG. 10: Progenitor Targeting Fragment).

Construction of the 3' Targeting Fragments

The 3' untranslated region of the EPO gene was amplified from pBKSII(−)PsubEPO (see pEPO$^2$) using the primer pair EPO3'-FOR3/EPO3'-REV. The PCR product was cleaved with NotI/BglII and the resulting NotI/BglII fragment was ligated with the NotI/BglII vector fragments of pEPO$^2$ or pEPO$^2$w/onsP2mut-HDV, respectively. The BamHI/KpnI vector fragments of the resulting plasmids were then ligated with the 3' targeting sequence. The latter was obtained by PCR amplification of nucleotides 51,567 to 53,621 according to GenBank Accession No. AF053356 from Hep G2 chromosomal DNA using the oligonucleotide pair Enh-FOR2/Enh-REV2 and subsequent cleavage with BanHI/KpnI. From the resulting plasmids, pBSKS(−)EPO3 3'targfrag or pBSKS(−)EPO3 3'targfrag-HDV, respectively, the 3' targeting fragments containing or, respectively, lacking the HDV ribozyme sequence (see FIG. 10) are prepared by cleavage with NotI.

Construction of the 5' Targeting Fragments

The Sindbis subgenomic promoter and the EPO 5' untranslated region were amplified from vector pBKSII(−)PsubEPO5' (see pEPO$^2$) using the primer pair Psub-FOR/EPO5'-REV3. The resulting fragment was cleaved with BamHI/KpnI and ligated with the BamHI/KpnI vector fragment of pBluescript II KS(−) (Stratagene). The resulting plasmid pBSKS(−)PsubEPO5'un was cleaved with SstI/BamHI to be ligated to the 5' targeting sequence. The latter was obtained by amplification of nucleotides 56,604 to 58,742 according to GenBank Accession No. AF053356 and 5' Sindbis sequence (1–46). The oligonucleotide pair PEPOlong-FOR4/PEPOHIII-REV was used for PCR amplification on Hep G2 chromosomal DNA and the primer pair PEPOHIIIFOR/PEPOREVY on plasmid pBKSII(−)Pepo (see pEPO$^2$). These two PCR fragments were assembled by SOE PCR using the primers PEPOlong-FOR4/PEPOREVY and the product was subsequently cleaved with SstI/BamHI. The resulting vector pBSKS(−)PEPOlongNSP5'PsubEPO5'un was digested with MunI/BamHI and ligated with the 4,550 bp MunI/BamHI fragment of vector pCYTts. The obtained vector was cleaved with MunI, dephosphorylated and ligated with the 2,743 bp MunI fragment of pCYTts. From the resulting vector pBSKS(−)EPO3 5'targfrag. the 5' targeting fragment comprising both the nsP2 and the ts6 mutation (see FIG. 10) is obtained by cleavage with NotI.

For the 5' targeting fragment lacking the nsP2 mutation, the 4,550 bp MunI/BamHI fragment was isolated from vector pBKSII(−)NSP5'w/onsP2mut-EPO (see pEPO$^2$w/onsP2mut-HDV) and ligated into the MunI/BamHI vector fragment of plasmid pBSKS(−)PEPOlongneoPsubEPO5'un. The resulting vector was cleaved with MunI, dephosphorylated and ligated with the 2,743 bp MunI fragment of pCYTts. From the resulting vector pBSKS(−)EPO3 5'targfragw/onsP2mut, the 5' targeting fragment is obtained by cleavage with NotI.

The 5' targeting fragment carrying a deletion within the Sindbis non structural protein coding sequence (see FIG. 10) was constructed by cleavage of the plasmid pBSKS(−)EPO3 5'targfrag with enzymes Eco47III/BamHI, and upon filling in the BamHI overhang, the vector was recircularized by ligation to obtain plasmid pBSKS(−)EPO3 5'targfragnsPΔEH. The 5' targeting fragment of this vector is obtained by cleavage with NotI.

It will be clear to one skilled in the art that other genetic elements or modifications not mentioned in this example may be included in the homologous recombination targeting fragments (like e.g., genetic modifications depicted in Example 9) and that the final design of homologous recombination targeting fragments will depend upon the EPO productivities conferred by the respective homologous recombination 'mimic' constructs (see Example 9).

TABLE 2

Oligonucleotides

| Designation | Sequence | SEQ ID NO |
|---|---|---|
| Enh-FOR | d(GTTTTCTCGAGCCTCCAAATCCCCTGGCTC) | 2 |
| Enh-FOR2 | d(CCTCCGGATCCGTCGAGCCTCCAAATCCCCTG GCTCTGTCC) | 21 |
| Enh-REV | d(AGAGGTACCTCCAACCGCACCTGTG) | 4 |
| Enh-REV2 | d(GGTGGGGTACCGCGGCCGCATCCTCTGAGCTC AGGAGTTTGAGACC) | 22 |

TABLE 2-continued

Oligonucleotides

| Designation | Sequence | SEQ ID NO |
|---|---|---|
| EPO3'-FOR | d(GCTGTCTAGAGAGCAACTCTGAGATCTAAG) | 6 |
| EPO3-FOR3 | d(GGGGAGCTCGCGGCCGCCAGGTGTGTCCACCT GGGCATATC) | 23 |
| EPO3'-REV | d(CCAACCCTCGAGGCCAGCCCCCATCCTGTC) | 8 |
| EPO5'-FOR | d(CAACACCACCACCAGAGTCCCTGGGCCACCC) | 9 |
| EPO5'-REV | d(GGACATTCTAGAACAGATAGCC) | 10 |
| EPO5'-REV3 | d(GGTGGGTACCGCGGCCGCCTCCGCGCCTGGCC GGGG) | 24 |
| EPO5'un-FOR | d(CGCAAGCTTAGAGTCCCTGGGCCACCC) | 25 |
| -HDV | d(CTAAGGGAGGAATTCCCAACTTGTTTATTG) | 26 |
| HDV-FOR | d(AATTCGGGTCGGCATGGCATCTCCACCTCCTC GCGGTCCGACCTGGGCATCCGAAGGAGGACGCAC GTCCACTCGGATGGCTAAGGGAGC) | 12 |
| HDV-REV | d(AATTGCTCCCTTAGCCATCCGAGTGGACGTGC GTCCTCCTTCGGATGCCCAGGTCGGACCGCGAGG AGGTGGAGATGCCATGCCGACCCG) | 13 |
| nhnsPEco-REV | d(GGAAAAGCGCTAAAAGAGGCTGGGAC) | 27 |
| nhPEPOnot-FOR | d(CCGCGGTGGCGGCCGCTGGGCTTCC) | 28 |
| nhPEPOtRNA-FOR | d(CCAGAGCCGCATATAGTGGTGAGTATCCCCG) | 29 |
| nhPEPOtRNA-REV | d(CACCACTATATGCGGCTCTGGCCGGGGGTCG) | 30 |
| notsin5'-FOR | d(GCGCGCGCGGCCGCATTGACGGCGTAGTACAC ACTATTG) | 31 |
| Pepo-FOR | d(CCCGAGCTCGCGGCCGCTGGGCTTCCAGACCC AGC) | 14 |
| Pepo-FORX | d(CAACCCAGGCGTCCTGCCCCTGCTCTGAC) | 32 |
| PEPOHIIIFOR | d(CCTAAAGCTTCTGGGCTTCCAGACCCAGC) | 33 |
| PEPOHIIIREV | d(GGGTCTGGAAGCCCAGAAGCTTTAGG) | 34 |
| PEPOlongFOR3 | d(CGCGGTACCATGCGGCCGCGTTACTGCTGATT AGTATCTTGCTAATCATAGG) | 35 |
| PEPOlongFOR4 | d(GGTTGGGAGCTCGCGGCCGCGTTACTGCTGAT TAGTATCTTGCTAATCATAGG) | 36 |
| PEPOlongREV | d(CGGCTCGAGGCGGCTCTGGCCGGGGGTCGGG) | 37 |
| PEPOlongREV3 | d(CGGCTCGAGGCGGCTCTGGCCGGGGGTC) | 38 |
| Pepo-REV3 | d(CACCCGGGGTCAGAGCAGGGGCAGGAC) | 39 |
| PepoREVY | d(CTGTACAAGGATCCGTGCAATTGGTCGGCTGT TTG) | 40 |
| Psub-FOR | d(GGGGAGCTCGCGGCCGCGGAGGAGCGCTGATT CGGTTACTTCCACAGCG) | 17 |
| Psub-REV | d(CGGGGTGGCCCAGGGACTCTGGTGGTGGTGTT GTAGTATTAG) | 18 |
| rrEPO5'-FOR | d(GGCGCGGAGATGGGGGTGCACGGTGAGTAC) | 41 |
| rrEPO5'-REV | d(GACATTCTAGAACAGATAGCCAG) | 42 |
| rrNSPHPA-FOR | d(TATGGCGTTAACCGGTCTGATG) | 43 |
| rrNSPSOE | d(CGTGCACCCCCATCTCCGCGCCGGTGGTGGTG TTGTAGTATTAG) | 44 |
| SIN3'-FOR | d(CCAACCAAGCTTGTCGACGCCCCAATGATCCG ACCAGC) | 19 |
| 3'sineco47 | d(GCAAAGAGGTCGTCCATACGG) | 45 |
| subfor | d(GCGCGGAGCTCTGAGGTAGACAATATTAC ACC) | 46 |
| subrev | d(GCGCGGAGCTCTCAGGCACCGGGCTTGCG GGT) | 47 |
| SV40-REV | d(CTCGACGGCTCGAGACATGATAAGATACAT) | 20 |
| 5'SV40 PUR | d(ACGTACGCGTGCGGCCGCGTTAGGGTGTGGAA AGTCCCC) | 48 |
| SV40puro-REV | d(GCGCGCGGCCGCTTAATTAATGGACAAACCAC AACTAGAATGC) | 49 |

Example 12

EPO Production Process by Replicon Based Gene Activation

Introduction

Endogenous genes can be activated by replicon technology. A strategy is presented here for activation of the chromosomal EPO gene using an alphavirus replicon-based approach. Recent results demonstrated that the low transcription rate of the EPO promoter is sufficient to initiate the RNA replication cycle. Starting with a cell line that has at least a basal transcriptional activity from the EPO promoter, an EPO production cell line is constructed by homologous recombinations. All elements required for RNA replication are integrated into the chromosomal EPO locus, leading to high amplification of the EPO mRNA upon initial transcription from the EPO promoter. Between the EPO promoter and the 5' untranslated sequence of the EPO gene, the Sindbis 5' cis-acting sequences (CSE), the replicase gene and the viral subgenomic promoter are inserted. Into the 3' untranslated sequence of the EPO gene, the Sindbis 3' CSE is inserted.

The resulting producer cell line will carry a pCYTts-EPO like arrangement on the chromosome, similar to that shown in FIG. 3, without ever touching the EPO coding sequence itself. (The pCYTts expression system is described in detail in PCT publication WO 99/50432, the entire disclosure of which is incorporated herein by reference.) The resulting cell line allows for the development of a one-step EPO production process.

Genetic Constructions

The following two targeting DNA constructs for integration at the human chromosomal EPO locus are constructed having the features shown in FIGS. 5A–5B:

A. 3' Targeting Construct

The 3' targeting construct encompasses the Sindbis 3' CSE, which is required for RNA replication. Immediately downstream of this element, a stretch of 37 A residues is fused ("poly(A) tail"). The poly(A) tail may or may not be followed by the Hepatitis delta virus (HDV) antigenomic ribozyme (see FIG. 10; Perrotta & Been, *Nature* 350:434–436 (1991)). The ribozyme incises the RNA strand immediately 5' to its own sequence, thereby generating a proper poly(A) terminus. This has been shown to increase the expression of a reporter enzyme by a factor of 3–4 (Dubensky et al., *J. Virol.* 70:508–519 (1996); Pattnaik et al., *Cell* 69:1011–1020 (1992)). The HDV sequence (or the $A_{37}$ stretch, respectively) is followed by a transcriptional terminator and polyadenylation signal. Furthermore, a resistance marker is present on this construct for selection of recombinant clones. The targeting sequences of this construct are designed such that the poly(A) signal of the EPO gene is deleted by homologous recombination. Hence, the 5' targeting sequence encompasses a stretch of ~500 nucleotides of the 3' untranslated region of the EPO gene. The 3' targeting sequence of this construct encompasses a stretch of ~2 kb located downstream of the poly(A) signal. To reduce the fraction of non-homologous recombinants within the antibiotic resistant population, this construct may be flanked on one side by *Herpes simplex* thymidine kinase gene. This marker, which will normally be co-integrated into the chromosome in case of random integration (i.e., non-homologous recombination) can be counter-selected using gancyclovir.

Homologous recombination of the 3' targeting construct is performed in the first step. Among the antibiotic resistant population, clones having incorporated the construct homologously (i.e., at the correct site on the chromosome) are identified by methods known in the art (e.g., PCR or Southern Blot analysis).

B. 5' Targeting Constructs

The 5' targeting construct, which is inserted between the EPO promoter and the 5' untranslated region, encompasses a 5' cis-acting sequence required for RNA replication (either the authentic Sindbis 5' CSE or a modified version; see e.g., Monroe & Schlesinger (1983) *Proc. Natl. Acad. Sci. USA* 80:3279–3283), the replicase gene, a resistance marker operably linked to a viral subgenomic promoter, and a second subgenomic promoter that will drive transcription of the EPO gene. The 3' targeting sequence of this construct is homologous to the 5' untranslated region of the EPO gene (starting with nucleotide 1 of the main EPO RNA transcript; Costa-Giomi et al., *J. Biol. Chem.* 265:10185–10188 (1990)). The 3' targeting sequence covers about 2 kb of sequence upstream of the transcription start (ending with nucleotide -1 with respect to the transcription start). Expression of the resistance marker from the subgenomic promoter only occurs upon homologous recombination, since random integration of this construct at a different site does not lead to a replication-competent RNA molecule (due to the missing 3' CSE at that site). Nevertheless, correct integration of this construct is verified by PCR and Southern Blot analysis. Alternatively, the resistance marker (operably linked to a subgenomic promoter or an internal ribosome entry site) may be introduced on the 3' side of the EPO coding region (i.e., would be included on the 3' targeting fragment, immediately following on the 3' side of its 5' targeting sequence). The resistance cassette may be flanked by loxP sites (Sternberg & Hamilton, *J. Mol. Biol.* 150:467–486 (1981)) to enable this region to be deleted afterwards (by transient expression of the recombinase CRE) (see FIG. 1).

If inclusion of a resistance marker (operably linked to a subgenomic promoter or an internal ribosome entry site) on one of the targeting fragments for selection for correct integration of the 5' targeting fragment is not desired, the approach depicted in FIGS. 6A–6B can be followed. Here, a progenitor cell line is constructed, where both a positive and a negative selection marker are integrated between the EPO promoter and the 5' untranslated region of the EPO gene. The positive selection marker is required for selection of cells having integrated this fragment into their genome. Correct integration (i.e., by homologous recombination) has to be verified by methods known in the art (e.g., PCR, Southern Blot). The negative selection marker has to be conditionally functional, i.e., has to exert its function only under particular conditions. An example for such marker is the HSV-tk gene, which is lethal only in the presence of Gancyclovir or Acyclovir. When such progenitor cell line is used for integration of the 5' targeting fragment, both the previously introduced positive and negative selection markers are replaced by the final construct and homologously recombinant cells can be selected for by their resistance to Gancyclovir or Acyclovir.

As a further alternative, the 5' targeting construct can be co-transfected with an expression cassette essentially comprising the Sindbis 5' and 3' CSEs and a resistance marker operably linked to the viral subgenomic promoter (which will integrate randomly into the genome). This marker is expressed only in the presence of the Sindbis non-structural proteins, which will only be produced in reasonable amounts upon homologous recombination of the 5' targeting fragment (i.e., integration of the latter in the near 5' region of the already integrated 3' targeting fragment). Upon transfection, homologously recombinant cells are selected for the resistance marker and further characterized by PCR and Southern Blot analysis. A scheme similar to that described above is shown in FIGS. 5A–5B.

As an alternative to being included on the 5' targeting fragment, the nsP1–4 genes may also be expressed in trans, i.e., from a separate viral replicon (like pCYTts) or a regular non-replicating expression cassette (i.e., nsP1–4 coding sequence under control of an RNA polymerase II promoter), which would be integrated randomly into the cellular genome. Such approach would allow for a deletion within the nsP1–4 coding sequence on the 5' targeting fragment. In addition, the nsP1–4 coding sequences may be replaced by or parts of it may be fused to a sequence encoding a selection marker in such approach (see, e.g., Polo et al. *Proc. Natl. Acad. Sci. USA* 96:4598–4603 (1999)). The cis-acting sequence required for RNA replication introduced by such 5' targeting fragment may be either the authentic Sindbis 5' CSE or a modified version (see e.g., Monroe & Schlesinger (1983) *Proc. Natl. Acad. Sci. USA* 80:3279–3283 (1983)).

It will be clear to one skilled in the art, that the 3' targeting sequence of the 5' targeting fragment needs not necessarily correspond to the 5' untranslated region of the EPO gene. An alternative would be to use the sequence of intron 1 or part of it as 3' targeting sequence of the 5' targeting fragment. In the latter case, exon 1 of the EPO gene (or a different exon which exerts the same function) would have to be included on the 5' targeting fragment. Such approach may be desired in order to reduce the distance between the subgenomic promoter and the start codon of the EPO coding sequence.

The Recombinant Eukaryotic Host Cells

The 5' and 3' targeting constructs are introduced into recombination competent, human host cells which express EPO.

A minimal basal EPO expression is required for initiation of the replication cycle. Initially, the EPO replicon is transcribed from the chromosomal EPO promoter before self-propagation in the cytoplasm. For this reason, a human cell line is used in which the EPO promoter shows at least a basal activity (induction of EPO production by conditions known from literature (see e.g., Goldberg et al., *Proc. Natl. Acad. Sci. USA* 84:7972–7976 (1987)) and test for secreted EPO by immunological methods). While a considerable number of cell lines have been described in the literature which express human erythropoietin, the cell lines used herein are 293 and Hep G2.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method for modifying the expression characteristics of an endogenous target gene within the genome of a eukaryotic cell, said method comprising:
   (a) inserting exogenous polynucleotides by homologous recombination in the 5' and 3' regions flanking the coding region of the endogenous target gene to produce a recombinant eukaryotic host cell; and
   (b) culturing the recombinant eukaryotic host cell under conditions which allow for transcription and replication of RNA corresponding to the endogenous target gene;
   wherein the exogenous polynucleotides encode genetic elements required for RNA replication.

2. The method of claim 1, wherein at least one of the exogenous polynucleotides contains one or more selection markers.

3. The method of claim 2, wherein at least one of the exogenous polynucleotides contains a positive selection marker.

4. The method of claim 2, wherein at least one of the exogenous polynucleotides contains a negative selection marker,
   wherein the negative selection marker is excised from the exogenous polynucleotides when integration occurs by homologous recombination.

5. The method of claim 2, wherein at least one of the exogenous polynucleotides contains a positive selection marker and a negative selection marker,
   wherein the negative selection marker is excised from the exogenous polynucleotides when integration occurs by homologous recombination.

6. The method of claim 3, wherein the positive selection marker is selected from the group consisting of:
   (a) neomycin phosphotransferase;
   (b) metallothionein I;
   (c) metallothionein II;
   (d) dihydrofolate reductase;
   (e) hygromycin B phosphotransferase;
   (f) puromycin-N-acetyl-transferase;
   (g) xanthine/guanine phosphoribosyl transferase; and
   (h) histidinol dehydrogenase.

7. The method of claim 3, wherein the positive selection marker is tryptophan synthase.

8. The method of claim 4, wherein the negative selection marker is selected from the group consisting of:
   (a) *Herpes simplex* thymidine kinase;
   (b) cytosine deaminase;
   (c) Diptheria toxin;
   (d) xanthine/guanine phosphoribosyl transferase; and
   (e) hypoxanthine phosphoribosyl transferase.

9. The method of claim 2, wherein the selection marker is operably linked to a subgenomic promoter.

10. The method of claim 2, wherein the selection marker is operably linked to an RNA polymerase II promoter.

11. The method of claim 3, wherein the positive selection marker is co-transcribed with the coding region of the endogenous target gene as part of the same RNA molecule and is translated from an internal ribosome entry site.

12. The method of claim 1, wherein the genetic elements required for RNA replication are derived from a virus.

13. The method of claim 1, wherein the genetic elements required for RNA replication are derived from a Alphavirus.

14. The method of claim 13, wherein the endogenous target gene is operably linked to an Alphavirus subgenomic promoter.

15. The method of claim 1, wherein the eukaryotic cell is an animal cell.

16. The method of claim 15, wherein the animal cell is a vertebrate cell.

17. The method of claim 16, wherein the vertebrate cell is a mammalian cell.

18. The method of claim 17, wherein the mammalian cell is a human cell.

19. The method of claim 18, wherein the human cell is derived from an organ selected from the group consisting of:
   (a) kidney;
   (b) liver; and
   (c) testes.

20. The method of claim 19, wherein the human cell is Hep G2, Hep 3B, or a derivative thereof.

21. The method of claim 19, wherein the human cell is a 293 cell or a derivative thereof.

22. The method of claim 1, wherein the endogenous target gene encodes a ribozyme.

23. The method of claim 1, wherein the endogenous target gene encodes a polypeptide.

24. The method of claim 23, wherein said endogenous target gene encodes human erythropoietin.

25. The method of claim 23, wherein the polypeptide is selected from the group consisting of:
   (a) antithrombin III;
   (b) α-galactosidase;
   (c) granulocyte colony-stimulating factor;
   (d) granulocyte-macrophage colony-stimulating factor;
   (e) megakaryocyte-growth factor;
   (f) blood clotting factor VII;
   (g) blood clotting factor VIII;
   (h) blood clotting factor IX;
   (i) α-interferon ;
   (j) β-interferon;
   (k) γ-interferon;
   (l) interleukin-2;
   (m) tissue plasminogen activator;
   (n) thrombopoietin;
   (o) α I-antitrypsin;
   (p) LDL-receptor;
   (q) insulin; and
   (r) growth hormone.

26. A recombinant eukaryotic host cell produced by the method of claim 1.

27. A method for producing a polypeptide encoded by an endogenous target gene of a eukaryotic cell, said method comprising:
   (a) inserting exogenous polynucleotides by homologous recombination in the 5' and 3' regions flanking the endogenous target gene to produce a recombinant eukaryotic host cell; and
   (b) culturing the recombinant eukaryotic host cell under conditions which allow for transcription, replication, and translation of RNA corresponding to the endogenous target gene;
   wherein the exogenous polynucleotides encode genetic elements required for RNA replication which alter the expression characteristics of the endogenous target gene.

28. The method of claim 27, wherein at least one of the exogenous polynucleotides contains one or more selection markers.

29. The method of claim 28, wherein at least one of the exogenous polynucleotides contains a positive selection marker.

30. The method of claim 28, wherein at least one of the exogenous polynucleotides contains a negative selection marker,
   wherein the negative selection marker is excised from the exogenous polynucleotides when integration occurs by homologous recombination.

31. The method of claim 28, wherein at least one of the exogenous polynucleotides contains a positive selection marker and a negative selection marker,
   wherein the negative selection marker is excised from the exogenous polynucleotides when integration occurs by homologous recombination.

32. The method of claim 29, wherein the positive selection marker is selected from the group consisting of:
   (a) neomycin phosphotransferase;
   (b) metallothionein I;
   (c) metallothionein II;
   (d) dihydrofolate reductase;
   (e) hygromycin B phosphotransferase;
   (f) puromycin-N-acetyl-transferase;
   (g) xanthine/guanine phosphoribosyl transferase; and
   (h) histidinol dehydrogenase.

33. The method of claim 29, wherein the positive selection marker is tryptophan synthase.

34. The method of claim 30, wherein the negative selection marker is selected from the group consisting of:
   (a) *Herpes simplex* thymidine kinase;
   (b) cytosine deaminase;
   (c) Diptheria toxin;
   (d) xanthine/guanine phosphoribosyl transferase; and
   (e) hypoxanthine phosphoribosyl transferase.

35. The method of claim 28, wherein the selection marker is operably linked to a subgenomic promoter.

36. The method of claim 28, wherein the selection marker is operably linked to an RNA polymerase II promoter.

37. The method of claim 29, wherein the positive selection marker is co-transcribed with the coding region of the endogenous target gene as part of the same RNA molecule and is translated from an internal ribosome entry site.

38. The method of claim 27, wherein the genetic elements required for RNA replication are derived from a virus.

39. The method of claim 27, wherein the genetic elements required for RNA replication are derived from a Alphavirus.

40. The method of claim 39, wherein the endogenous target gene is operably linked to an Alphavirus subgenomic promoter.

41. The method of claim 27, wherein the eukaryotic cell is an animal cell.

42. The method of claim 41, wherein the animal cell is a vertebrate cell.

43. The method of claim 42, wherein the vertebrate cell is a mammalian cell.

44. The method of claim 43, wherein the mammalian cell is a human cell.

45. The method of claim 44, wherein the human cell is derived from an organ selected from the group consisting of:
   (a) kidney;
   (b) liver; and
   (c) testes.

46. The method of claim 45, wherein the human cell is Hep G2, Hep 3B, or a derivative thereof.

47. The method of claim 45, wherein the human cell is a 293 cell or a derivative thereof.

48. The method of claim 27, wherein the endogenous target gene encodes a ribozyme.

49. The method of claim 27, wherein the endogenous target gene encodes a polypeptide.

50. The method of claim 49, wherein said endogenous target gene encodes human erythropoietin.

51. The method of claim 49, wherein the polypeptide is selected from the group consisting of:
   (a) antithrombin III;
   (b) α-galactosidase;
   (c) granulocyte colony-stimulating factor;
   (d) granulocyte-macrophage colony-stimulating factor;
   (e) megakaryocyte-growth factor;
   (f) blood clotting factor VII;
   (g) blood clotting factor VIII;
   (h) blood clotting factor IX;
   (i) α-interferon;
   (j) β-interferon;
   (k) γ-interferon;
   (l) interleukin-2;
   (m) tissue plasminogen activator;
   (n) thrombopoietin;
   (o) α I-antitrypsin;
   (p) LDL-receptor;
   (q) insulin; and
   (r) growth hormone.

52. A method for modifying the expression characteristics of an endogenous target gene within the genome of a eukaryotic cell, said method comprising inserting exogenous nucleic acid into the 5' and 3' regions flanking the endogenous target gene by homologous recombination,
   wherein the exogenous nucleic acid encodes genetic elements required for RNA replication, and
   wherein RNA corresponding to the coding region of the endogenous target gene is amplified.

53. A DNA vector system for modifying the expression characteristics of an endogenous target gene within the genome of a eukaryotic cell comprising:
   (a) a 5' targeting construct; and
   (b) a 3' targeting construct;
   wherein the 5' and 3' targeting constructs encode genetic elements required for RNA replication.

54. The vector system of claim 53, wherein the genetic elements required for RNA replication are derived from a virus.

55. The vector system of claim 53, wherein the genetic elements required for RNA replication are derived from a Alphavirus.

56. The vector system of claim 55, wherein the Alphavirus is selected from the group consisting of:
   (a) Semliki Forest Virus;
   (b) Sindbis virus;
   (c) Venezuelan equine encephalomyelitis virus; and
   (d) Ross River Virus.

57. The vector system of claim 54, wherein at least one of the exogenous polynucleotides contains one or more selection markers.

58. The vector system of claim 57, wherein at least one of the exogenous polynucleotides contains a positive selection marker.

59. The vector system of claim 57, wherein at least one of the exogenous polynucleotides contains a negative selection marker,
   wherein the negative selection marker is excised from the exogenous polynucleotides when integration occurs by homologous recombination.

60. The vector system of claim 57, wherein at least one of the exogenous polynucleotides contains a positive selection marker and a negative selection marker, wherein the negative selection marker is excised from the exogenous polynucleotides when integration occurs by homologous recombination.

61. The vector system of claim 57, wherein the selection marker is operably linked to a subgenomic promoter.

62. The vector system of claim 57, wherein the selection marker is operably linked to an RNA polymerase II promoter.

63. The vector system of claim 58, wherein the positive selection marker is operably linked to an internal ribosome entry site.

64. The vector system of claim 58, wherein the positive selection marker is selected from the group consisting of:

(a) neomycin phosphotransferase;
(b) metallothionein I;
(c) metallothionein II;
(d) dihydrofolate reductase;
(e) hygromycin B phosphotransferase;
(f) puromycin-N-acetyl-transferase;
(g) xanthine/guanine phosphoribosyl transferase; and
(h) histidinol dehydrogenase.

65. The vector system of claim 58, wherein the positive selection marker is tryptophan synthase.

66. The vector system of claim 59, wherein the negative selection marker is selected from the group consisting of:

(a) *Herpes simplex* thymidine kinase;
(b) cytosine deaminase;
(c) Diptheria toxin;
(d) xanthine/guanine phosphoribosyl transferase; and
(e) hypoxanthine phosphoribosyl transferase.

67. The vector system of claim 66, wherein the endogenous target gene is operably linked to an Alpahvirus subgenomic promoter.

* * * * *